US012576041B1

(12) United States Patent
Nakamura

(10) Patent No.: US 12,576,041 B1
(45) Date of Patent: Mar. 17, 2026

(54) TRANSIENT EXPRESSION OF BIOLOGIC MATERIALS

(71) Applicant: Dean Nakamura, Montgomery Village, MD (US)

(72) Inventor: Dean Nakamura, Montgomery Village, MD (US)

(*) Notice: Subject to any disclaimer, the term of this patent is extended or adjusted under 35 U.S.C. 154(b) by 775 days.

(21) Appl. No.: 17/865,257

(22) Filed: Jul. 14, 2022

Related U.S. Application Data

(60) Provisional application No. 63/389,236, filed on Jul. 14, 2022, provisional application No. 63/221,909, filed on Jul. 14, 2021.

(51) Int. Cl.

| | |
|---|---|
| *A61K 39/12* | (2006.01) |
| *A61K 9/51* | (2006.01) |
| *A61K 39/02* | (2006.01) |
| *A61K 39/05* | (2006.01) |
| *A61K 39/08* | (2006.01) |
| *A61K 39/145* | (2006.01) |
| *A61K 39/165* | (2006.01) |
| *A61K 39/20* | (2006.01) |
| *A61K 39/215* | (2006.01) |
| *A61K 39/245* | (2006.01) |
| *A61K 39/29* | (2006.01) |
| *C12N 7/00* | (2006.01) |
| *A61K 39/00* | (2006.01) |

(52) U.S. Cl.
CPC ............ *A61K 9/5123* (2013.01); *A61K 39/05* (2013.01); *A61K 39/08* (2013.01); *A61K 39/099* (2013.01); *A61K 39/145* (2013.01); *A61K 39/165* (2013.01); *A61K 39/20* (2013.01); *A61K 39/215* (2013.01); *A61K 39/245* (2013.01); *A61K 39/29* (2013.01); *A61K 39/292* (2013.01); *C12N 7/00* (2013.01); *A61K 2039/55555* (2013.01); *C12N 2710/16134* (2013.01); *C12N 2760/16134* (2013.01); *C12N 2760/16234* (2013.01); *C12N 2760/18434* (2013.01); *C12N 2760/18534* (2013.01); *C12N 2760/18734* (2013.01); *C12N 2770/20034* (2013.01); *C12N 2770/24234* (2013.01)

(58) Field of Classification Search
None
See application file for complete search history.

(56) References Cited

FOREIGN PATENT DOCUMENTS

| | | | | |
|---|---|---|---|---|
| WO | WO-2018200975 A1 | * | 11/2018 | .............. A61P 31/14 |
| WO | WO-2021226664 A1 | * | 11/2021 | .............. A61P 31/14 |

OTHER PUBLICATIONS

Carlos et al., "Humoral immunity to immunodominant epitopes of Hepatitis C virus in individuals infected with genotypes 1a or 1b," Clinical Immunology, 111: 22-27 (Year: 2004).*

* cited by examiner

*Primary Examiner* — M Franco G Salvoza
(74) *Attorney, Agent, or Firm* — MDIP LLC

(57) ABSTRACT

Compositions containing two or more lipid nanoparticles, each containing a different mRNA, are described.

13 Claims, No Drawings

TRANSIENT EXPRESSION OF BIOLOGIC MATERIALS

FIELD OF THE INVENTION

The instant disclosure relates to expressing at least two polypeptides in a subject using at least two manufactured messenger RNA's.

BACKGROUND

Years of research in three areas, among others: (1) efficient in vivo translation of exogenous message; (2) ionizable cationic lipids for drug delivery vehicles; and (3) antigen presentation to a host immune system, resulted in recent realizing of mRNA prophylactics.

In vivo lability of message has been overcome sufficiently by, for example, reducing immunogenicity of an administered mRNA so a host immune response can be focused on a polypeptide expressed by an introduced mRNA. Incorporation of modified bases in place of one of the four bases commonly found in mRNA's, such as, pseudouridine for uridine, apparently extends message survival in vivo. Known ancillary sequences, such as, a 5' cap, 5' and/or 3' UTR's and a poly-A tail, enhance translation of manufactured message. Codons can be optimized for expression in human. Codons also can be optimized to minimize uracil content. On delivery, a message must survive in tissue or tissue space, must enter a cell, such as, an immune system cell, and then must be accessible to and functionally engage cellular translation machinery.

Efficient delivery of a message to cell translation machinery was obtained with creation of ionizable cationic lipids which, when combined with two structural lipids, a PEGylated lipid and an mRNA, using microfluidic methods and devices, form dense, nanometer-sized particles (LNP). An mRNA molecule essentially is encapsulated within a shell composed of lipid, however, an mRNA can be attached to a surface of a lipid particle, among other configurations. Two more important components of an LNP are an ionizable cationic lipid which attracts an anionic mRNA, may contribute to LNP formation and is involved in escape of message from an endosome in a cell; and PEGylated lipid which contributes to particle size, forms a steric barrier to minimize agglomeration of nanoparticles during manufacture and storage, and shields particles from in vivo environments, such as, opsonins, thereby avoiding rapid LNP inactivation and clearance. In vivo, PEGylated lipids rapidly transfer from an LNP to host serum lipoproteins thereby altering architecture of an LNP that enters a cell, for example, exposing ionizable cationic lipids.

A greater, accumulated knowledge of how a host raises an immune response governed, for example, directing, in part, design of two mRNA SARS-COV-2 vaccines granted emergency use authorization, both carry message that encodes a signal peptide and a modified spike protein where two Pro substitutions at juncture of HR1 and CH domains lock the expressed spike protein in the prefusion configuration.

SUMMARY

The instant invention is directed to transient expression of at least two polypeptides in a subject using individual populations of lipid nanoparticles (LNP), each population carrying a different mRNA.

In a first embodiment, at least two manufactured translatable messenger RNA's (mRNA) are introduced into a subject cell, and a first and a second mRNA, so long as functional, are translated enabling expression of encoded a first and a second polypeptide, respectively, in the subject cell, wherein said first polypeptide lacks an immunodominant epitope.

In a first feature of said first embodiment, said first or second polypeptide comprises a SARS-COV-2 prefusion spike protein.

In a second feature of said first embodiment, said first or second polypeptide comprises an S1 subunit of a SARS-COV-2 prefusion spike protein.

In a third feature of said first embodiment, said first or second polypeptide comprises a prefusion S2 subunit of a SARS-COV-2 prefusion spike protein.

In a fourth feature of said first embodiment, a composition comprises two formulations, a first formulation comprising a first LNP comprising said first mRNA encoding a SARS-COV-2 S1 subunit comprising N terminal domain (NTD) and a receptor binding domain (RBD); and a second formulation comprising a second LNP comprising said second mRNA encoding a SARS-COV-2 prefusion S2 subunit.

In a fifth feature of said first embodiment, a composition comprises two formulations, a first formulation comprising a first LNP comprising said second mRNA encoding a SARS-COV-2 S1 subunit comprising N terminal domain (NTD) and a receptor binding domain (RBD); and a second formulation comprising a second LNP comprising said first mRNA encoding a SARS-COV-2 prefusion S2 subunit.

In a sixth feature of said first embodiment, said first or second polypeptide comprises an antigenic polypeptide of hepatitis A.

In a seventh feature of said first embodiment, said first or second polypeptide comprises an antigenic polypeptide of hepatitis B.

In an eighth feature of said first embodiment, a composition comprises two formulations, a first formulation comprising a first LNP comprising said first mRNA encoding an antigenic polypeptide of hepatitis A; and a second formulation comprising a second LNP comprising said second mRNA encoding an antigenic polypeptide of hepatitis B.

In a ninth feature of said first embodiment, a composition comprises two formulations, a first formulation comprising a first LNP comprising said first mRNA encoding an antigenic polypeptide of hepatitis B; and a second formulation comprising a second LNP comprising said second mRNA encoding an antigenic polypeptide of hepatitis A.

In a tenth feature of said first embodiment, said first or second polypeptide comprises an antigenic polypeptide of *Corynebacterium diptheriae.*

In a first aspect of said tenth feature of said first embodiment, said antigenic polypeptide comprises a detoxified toxin.

In an eleventh feature of said first embodiment, said first or second polypeptide comprises an antigenic polypeptide of *Clostridium tetani.*

In a first aspect of said eleventh feature of said first embodiment, said antigenic polypeptide comprises a detoxified toxin.

In a twelvth feature of said first embodiment, a composition comprises two formulations, a first formulation comprising a first LNP comprising said first mRNA encoding an antigenic polypeptide of *Corynebacterium diptheriae;* and a second formulation comprising a second LNP comprising said second mRNA encoding an antigenic polypeptide of *Clostridium tetani.*

In a first aspect of said twelvth feature of said first embodiment, said antigenic polypeptide of *Corynebacte-*

*rium diptheriae*, said antigenic polypeptide of *Clostridium tetani* or both comprise a detoxified toxin.

In a thirteenth feature of said first embodiment, a composition comprises two formulations, a first formulation comprising a first LNP comprising said second mRNA encoding an antigenic polypeptide of *Corynebacterium diptheriae*; and a second formulation comprising a second LNP comprising said first mRNA encoding an antigenic polypeptide of *Clostridium tetani*.

In a first aspect of said thirteenth feature of said first embodiment, said antigenic polypeptide of *Corynebacterium diptheriae*, said antigenic polypeptide of *Clostridium tetani* or both comprise a detoxified toxin.

In a fourteenth feature of said first embodiment, said first or second polypeptide comprises an antigenic polypeptide of *Bordatella pertussis*.

In a first aspect of said fourteenth feature of said first embodiment, said antigenic polypeptide comprises a detoxified toxin.

In a fifteenth feature of said first embodiment, a composition comprises two formulations, a first formulation comprising a first LNP comprising said first mRNA encoding an antigenic polypeptide of *Corynebacterium diptheriae*; and a second formulation comprising a second LNP comprising said second mRNA encoding an antigenic polypeptide of *Bordatella pertussis*.

In a first aspect of said fifteenth feature of said first embodiment, said antigenic polypeptide of *Corynebacterium diptheriae*, said antigenic polypeptide of *Bordatella pertussis* or both comprise a detoxified toxin.

In a sixteenth feature of said first embodiment, a composition comprises two formulations, a first formulation comprising a first LNP comprising said first mRNA encoding an antigenic polypeptide of *Bordatella pertussis*; and a second formulation comprising a second LNP comprising said second mRNA encoding an antigenic polypeptide of *Corynebacterium diptheriae*.

In a first aspect of said sixteenth feature of said first embodiment, said antigenic polypeptide of *Corynebacterium diptheriae*, said antigenic polypeptide of *Bordatella pertussis* or both comprise a detoxified toxin.

In a seventeenth feature of said first embodiment, a composition comprises two formulations, a first formulation comprising a first LNP comprising said first mRNA encoding an antigenic polypeptide of *Clostridium tetani*; and a second formulation comprising a second LNP comprising said second mRNA encoding an antigenic polypeptide of *Bordatella pertussis*.

In a first aspect of said seventeenth feature of said first embodiment, said antigenic polypeptide of *Bordatella pertussis*, said antigenic polypeptide of *Clostridium tetani* or both comprise a detoxified toxin.

In an eighteenth feature of said first embodiment, a composition comprises two formulations, a first formulation comprising a first LNP comprising said first mRNA encoding an antigenic polypeptide of *Bordatella pertussis* and a second formulation comprising a second LNP comprising said second mRNA encoding an antigenic polypeptide of *Clostridium tetani*.

In a first aspect of said eighteenth feature of said first embodiment, said antigenic polypeptide of *Bordatella pertussis*, said antigenic polypeptide of *Clostridium tetani* or both comprise a detoxified toxin.

In a nineteenth feature of said first embodiment, a composition comprises three formulations, a first formulation comprising a first LNP comprising said first mRNA encoding an antigenic polypeptide of *Corynebacterium diptheriae*, a second formulation comprising a second LNP comprising said second mRNA encoding an antigenic polypeptide of *Clostridium tetani* and a third formulation comprising a third LNP comprising a third mRNA encoding an antigenic polypeptide of *Bordatella pertussis*.

In a first aspect of said nineteenth feature of said first embodiment, said antigenic polypeptide of *Corynebacterium diptheriae*, said antigenic polypeptide of *Clostridium tetani*, and/or said antigenic polypeptide of *Bordatella pertussis* comprises a detoxified toxin.

In a twentieth feature of said first embodiment, a composition comprises three formulations, a first formulation comprising a first LNP comprising said first mRNA encoding an antigenic polypeptide of *Clostridium tetani*, a second formulation comprising a second LNP comprising said second mRNA encoding an antigenic polypeptide of *Corynebacterium diptheriae* and a third formulation comprising a third LNP comprising a third mRNA encoding an antigenic polypeptide of *Bordatella pertussis*.

In a first aspect of said twentieth feature of said first embodiment, said antigenic polypeptide of *Corynebacterium diptheriae*, said antigenic polypeptide of *Clostridium tetani*, and/or said antigenic polypeptide of *Bordatella pertussis* comprises a detoxified toxin.

In a twenty-first feature of said first embodiment, a composition comprises three formulations, a first formulation comprising a first LNP comprising said first mRNA encoding an antigenic polypeptide of *Bordatella pertussis*, a second formulation comprising a second LNP comprising said second mRNA encoding an antigenic polypeptide of *Clostridium tetani* and a third formulation comprising a third LNP comprising a third mRNA encoding an antigenic polypeptide of *Corynebacterium diptheriae*.

In a first aspect of said twenty-first feature of said first embodiment, said antigenic polypeptide of *Corynebacterium diptheriae*, said antigenic polypeptide of *Clostridium tetani*, and/or said antigenic polypeptide of *Bordatella pertussis* comprises a detoxified toxin.

In a twenty-second feature of said first embodiment, said first or second polypeptide comprises an antigenic polypeptide of influenza A.

In a twenty-third feature of said first embodiment, said first or second polypeptide comprises an antigenic polypeptide of influenza B.

In a twenty-fourth feature of said first embodiment, said first or second polypeptide comprises an antigenic polypeptide of influenza hemagglutinin.

In a twenty-fifth feature of said first embodiment, said first or second polypeptide comprises an antigenic polypeptide of influenza neuraminidase.

In a twenty-sixth feature of said first embodiment, said first or second polypeptide comprises an antigenic polypeptide of influenza A subtype H1, H2 or H3.

In a twenty-seventh feature of said first embodiment, said first or second polypeptide comprises an antigenic polypeptide of influenza A subtype N1 or N2.

In a twenty-eighth feature of said first embodiment, a composition comprises two formulations, a first formulation comprising a first LNP comprising said first mRNA encoding an antigenic polypeptide of influenza A subtype H1, H2 or H3 and a second formulation comprising a second LNP comprising said second mRNA encoding an antigenic polypeptide of influenza A subtype N1 or N2.

In a twenty-ninth feature of said first embodiment, a composition comprises two formulations, a first formulation comprising a first LNP comprising said second mRNA encoding an antigenic polypeptide of influenza A subtype H1, H2 or H3 and a second formulation comprising a second LNP comprising said first mRNA encoding an antigenic polypeptide of influenza A subtype N1 or N2.

In a thirtieth feature of said embodiment, said first polypeptide comprises an antigen, an epitope or a determinant.

In a thirty-first feature of said first embodiment, said second polypeptide comprises an adjuvant.

In a first aspect of said thirtieth feature of said first embodiment, further comprising a second LNP comprising said second mRNA encoding an adjuvant.

In a thirty-second feature of said first embodiment, said first or second polypeptide comprises an antigenic polypeptide of measles virus.

In a first aspect of said thirty-second feature of said first embodiment, said antigenic polypeptide comprises H.

In a thirty-third feature of said first embodiment, said first or second polypeptide comprises an antigenic polypeptide of mumps virus.

In a first aspect of said thirty-third feature of said first embodiment, said antigenic polypeptide comprises HN.

In a thirty-fourth feature of said first embodiment, said first or second polypeptide comprises an antigenic polypeptide of rubella virus.

In a first aspect of said thirty-fourth feature of said first embodiment, said antigenic polypeptide comprises E1.

In a second aspect of said thirty-fourth feature of said first embodiment, said antigenic polypeptide comprises E2.

In a thirty-fifth feature of said first embodiment, a composition comprises two formulations, a first formulation comprising a first LNP comprising said first mRNA encoding an antigenic polypeptide of measles virus and a second formulation comprising a second LNP comprising said second mRNA encoding an antigenic polypeptide of mumps virus.

In a thirty-sixth feature of said first embodiment, a composition comprises two formulations, a first formulation comprising a second LNP comprising said second mRNA encoding an antigenic polypeptide of measles virus and a second formulation comprising a first LNP comprising said first mRNA encoding an antigenic polypeptide of mumps virus.

In a thirty-seventh feature of said first embodiment, a composition comprises three formulations, a first formulation comprising a first LNP comprising said first mRNA encoding an antigenic polypeptide of measles virus; a second formulation comprising a second LNP comprising a second mRNA encoding an antigenic polypeptide of mumps virus; and a third formulation comprising a third LNP comprising a third mRNA encoding an antigenic polypeptide of rubella virus.

In a thirty-eighth feature of said first embodiment, the composition comprises three formulations, a first formulation comprising a first LNP comprising said first mRNA encoding an antigenic polypeptide of mumps virus; a second formulation comprising a second LNP comprising a second mRNA encoding an antigenic polypeptide of measles virus; and a third formulation comprising a third LNP comprising a third mRNA encoding an antigenic polypeptide of rubella virus.

In a thirty-ninth feature of said first embodiment, a composition comprises three formulations, a first formulation comprising a first LNP comprising said first mRNA encoding an antigenic polypeptide of rubella virus; a second formulation comprising a second LNP comprising a second mRNA encoding an antigenic polypeptide of mumps virus;

and a third formulation comprising a third LNP comprising a third mRNA encoding an antigenic polypeptide of measles virus.

In a fortieth feature of said first embodiment, said first or second polypeptide comprises an antigenic polypeptide of hepatitis C.

In a first aspect of said fortieth feature of said first embodiment, said antigenic polypeptide comprises E2.

In a second aspect of said fortieth feature of said first embodiment, said antigenic polypeptide comprises E2 lacking HVR1.

In a third aspect of said fortieth feature of said first embodiment, said antigenic polypeptide comprises E1.

In a forty-first feature of said first embodiment, said first or second polypeptide comprises an antigenic polypeptide of respiratory syncytial virus (RSV).

In a first aspect of said forty-first feature of said first embodiment, said antigenic polypeptide comprises F1.

In a second aspect of said forty-first feature of said first embodiment, said antigenic polypeptide comprises F2.

In a third aspect of said forty-first feature of said first embodiment, said antigenic polypeptide comprises prefusion F1.

In a fourth aspect of said forty-first feature of said first embodiment, said antigenic polypeptide comprises postfusion F1.

In a forty-second feature of said first embodiment, said first or second polypeptide comprises an antigenic polypeptide of cytomegalovirus (CMV).

In a first aspect of said forty-second feature of said first embodiment, said antigenic polypeptide comprises gH, gL or gO.

In a second aspect of said forty-second feature of said first embodiment, said antigenic polypeptide comprises UL128, UL130 or UL131.

In a second embodiment, a composition comprises at least two lipid nanoparticles (LNP): a) a first LNP comprising a first mRNA encoding a polypeptide, said first mRNA comprising a sequence encoding an operable signal peptide, wherein said polypeptide expressed by said first mRNA is secreted from a cell comprising said first LNP; and b) a second LNP comprising a second mRNA encoding said polypeptide, said second mRNA comprising one or more sequences encoding a lysine domain, wherein said polypeptide expressed by said second mRNA is not secreted by a cell comprising said second LNP.

In a first feature of said second embodiment, said polypeptide comprises SARS-COV-2 prefusion spike protein.

In a second feature of said second embodiment, said polypeptide comprises an S1 subunit of a SARS-COV-2 prefusion spike protein.

In a third feature of said second embodiment, said polypeptide comprises a prefusion S2 subunit of a SARS-COV-2 prefusion spike protein.

In a fourth feature of said second embodiment, a composition comprises two formulations, a first formulation comprising said polypeptide comprising an antigenic polypeptide of a SARS-COV-2 S1 subunit comprising N terminal domain (NTD) and receptor binding domain (RBD); and a second formulation comprising said polypeptide comprising an antigenic polypeptide of a SARS-COV-2 prefusion S2 subunit.

In a fifth feature of said second embodiment, said polypeptide comprises an antigenic polypeptide of hepatitis A.

In a sixth feature of said second embodiment, said polypeptide comprises an antigenic polypeptide of hepatitis B.

In a seventh feature of said second embodiment, a composition comprises two formulations, a first formulation comprising said polypeptide comprising an antigenic polypeptide of hepatitis A and a second formulation comprising said polypeptide comprising an antigenic polypeptide of hepatitis B.

In an eighth feature of said second embodiment, said polypeptide comprises an antigenic polypeptide of *Corynebacterium diptheriae*.

In a first aspect of said eighth feature of said second embodiment, said antigenic polypeptide comprises a detoxified toxin.

In a ninth feature of said second embodiment, said polypeptide comprises an antigenic polypeptide of *Clostridium tetani*.

In a first aspect of said ninth feature of said second embodiment, said antigenic polypeptide comprises a detoxified toxin.

In a tenth feature of said second embodiment, a composition comprises two formulations, a first formulation comprising said polypeptide comprising an antigenic polypeptide of *Corynebacterium diptheriae* and a second formulation comprising said polypeptide comprising an antigenic polypeptide of *Clostridium tetani*.

In a first aspect of said tenth feature of said second embodiment, said antigenic polypeptide of *Corynebacterium diptheriae*, said antigenic polypeptide of *Clostridium tetani* or both comprise a detoxified toxin.

In an eleventh feature of said second embodiment, said polypeptide comprises an antigenic polypeptide of *Bordatella pertussis*.

In a first aspect of said eleventh feature of said second embodiment, said antigenic polypeptide comprises a detoxified toxin.

In a twelvth feature of said second embodiment, a composition comprises two formulations, a first formulation comprising said polypeptide comprising an antigenic polypeptide of *Corynebacterium diptheriae* and a second formulation comprising said polypeptide comprising an antigenic polypeptide of *Bordatella pertussis*.

In a first aspect of said twelvth feature of said second embodiment, said antigenic polypeptide of *Corynebacterium diptheriae*, said antigenic polypeptide of *Bordatella pertussis* or both comprise a detoxified toxin.

In a thirteenth feature of said second embodiment, a composition comprises two formulations, a first formulation comprising said polypeptide comprising an antigen polypeptide of *Clostridium tetani* and a second formulation comprising said polypeptide comprising an antigenic polypeptide of *Bordatella pertussis*.

In a first aspect of said thirteenth feature of said second embodiment, said antigenic polypeptide of *Bordatella pertussis*, said antigenic polypeptide of *Clostridium tetani* or both comprise a detoxified toxin.

In a fourteenth feature of said second embodiment, a composition comprises three formulations, a first formulation comprising said polypeptide comprising an antigenic polypeptide of *Corynebacterium diptheriae*; a second formulation comprising said polypeptide comprising an antigenic polypeptide of *Clostridium tetani*; and a third formulation comprising said polypeptide comprising an antigenic polypeptide of *Bordatella pertussis*.

In a first aspect of said fourteenth feature of said second embodiment, said antigenic polypeptide of *Corynebacterium diptheriae*, said antigenic polypeptide of *Clostridium tetani* and/or said antigenic polypeptide of *Bordatella pertussis* comprises a detoxified toxin.

In a fifteenth feature of said second embodiment, said polypeptide comprises an antigenic polypeptide of influenza A.

In a sixteenth feature of said second embodiment, said polypeptide comprises an antigenic polypeptide of influenza B.

In a seventeenth feature of said second embodiment, said polypeptide comprises an antigenic polypeptide of influenza hemagglutinin.

In an eighteenth feature of said second embodiment, said polypeptide comprises an antigenic polypeptide of influenza neuraminidase.

In a nineteenth feature of said second embodiment, said polypeptide comprises an antigenic polypeptide of influenza A subtype H1, H2 or H3.

In a twentieth feature of said second embodiment, said polypeptide comprises an antigenic polypeptide of influenza A subtype N1 or N2.

In a twenty-first feature of said second embodiment, a composition comprises two formulations, a first formulation comprising said polypeptide comprising an antigenic polypeptide of influenza A subtype H1, H2 or H3 and a second formulation comprising said polypeptide comprising an antigenic polypeptide of influenza A subtype N1 or N2.

In a twenty-second feature of said second embodiment, said polypeptide comprises an antigen, an epitope or a determinant.

In a first aspect of said twenty-second feature of said second embodiment, further comprising a third LNP comprising an mRNA encoding a polypeptide comprising an adjuvant.

In a twenty-third feature of said second embodiment, said polypeptide comprises an antigenic polypeptide of measles virus.

In a first aspect of said twenty-third feature of said second embodiment, said antigenic polypeptide comprises H.

In a twenty-fourth feature of said second embodiment, said polypeptide comprises an antigenic polypeptide of mumps virus.

In a first aspect of said twenty-fourth feature of said second embodiment, said antigenic polypeptide comprises HN.

In a twenty-fifth feature of said second embodiment, said polypeptide comprises an antigenic polypeptide of rubella virus.

In a first aspect of said twenty-fifth feature of said second embodiment, said antigenic polypeptide comprises E1.

In a second aspect of said twenty-fifth feature of said second embodiment, said antigenic polypeptide comprises E2.

In a twenty-sixth feature of said second embodiment, a composition comprises two formulations, a first formulation comprising said polypeptide comprises an antigenic polypeptide of measles virus and a second formulation comprising said polypeptide comprises an antigenic polypeptide of mumps virus.

In a twenty-seventh feature of said second embodiment, a composition comprises two formulations, a first formulation comprising said polypeptide comprising an antigenic polypeptide of measles virus and a second formulation comprising said polypeptide comprises an antigenic polypeptide of rubella virus.

In a twenty-eighth feature of said second embodiment, a composition comprises two formulations, a first formulation comprising said polypeptide comprising an antigenic polypeptide of rubella virus and a second formulation comprising said polypeptide comprising an antigenic polypeptide of mumps virus.

In a twenty-ninth feature of said second embodiment, a composition comprises three formulations, a first formulation comprising said polypeptide comprising an antigenic polypeptide of measles virus, a second formulation comprising said polypeptide comprising an antigenic polypeptide of mumps virus and a third formulation comprising said polypeptide comprising an antigenic polypeptide of rubella virus.

In a thirtieth feature of said second embodiment, said polypeptide comprises an antigenic polypeptide of hepatitis C.

In a first aspect of said thirtieth feature of said second embodiment, said antigenic polypeptide comprises E2.

In a second aspect of said thirtieth feature of said second embodiment, said antigenic polypeptide comprises E2 lacking HVR1.

In a third aspect of said thirtieth feature of said second embodiment, said antigenic polypeptide comprises E1

In a thirty-first feature of said second embodiment, said polypeptide comprises an antigenic polypeptide of respiratory syncytial virus (RSV).

In a first aspect of said thirty-first feature of said second embodiment, said antigenic polypeptide comprises F1.

In a second aspect of said thirty-first feature of said second embodiment, said antigenic polypeptide comprises F2.

In a third aspect of said thirty-first feature of said second embodiment, said antigenic polypeptide comprises prefusion F1.

In a fourth aspect of said thirty-first feature of said second embodiment, said antigenic polypeptide comprises postfusion F1.

In a thirty-second feature of said second embodiment, said polypeptide comprises an antigenic polypeptide of cytomegalovirus.

In a first aspect of said thirty-second feature of said second embodiment, said antigenic polypeptide comprises gH, gL or gO.

In a second aspect of said thirty-second feature of said second embodiment, said antigenic polypeptide comprises UL128, UL130 or UL131.

In a third embodiment, a composition comprises at least two populations of LNP's, a first population comprising an mRNA encoding an epitope; and a second LNP population comprising a second LNP carrying an mRNA encoding a cytotoxin and on a surface of said second LNP, a targeting moiety.

In a first aspect of said third embodiment, said epitope is expressed on a pathogen.

In a first item of said first aspect of said third embodiment, said pathogen is a hepatitis virus.

In a second item of said first aspect of said third embodiment, said pathogen is *Bordatella pertussis, Corynebacterium diptheriae* or *Clostridium tetani.*

In a third item of said first aspect of said third embodiment, said pathogen is an influenza A virus or an influenza B virus.

In a fourth item of said first aspect of said third embodiment, said pathogen is a measles virus, a mumps virus or a rubella virus.

In a fifth item of said first aspect of said third embodiment, said pathogen is a respiratory syncytial virus.

In a sixth item of said first aspect of said third embodiment, said pathogen is a cytomegalovirus.

In a seventh item of said first aspect of said third embodiment, said pathogen is a SARS-COV-2 virus.

In a second aspect of said third embodiment, said epitope is expressed on a cancer cell.

In a first item of said first second aspect of said third embodiment, said cancer cell comprises a lung cancer, a breast cancer, a prostate cancer, a colorectal cancer, a white blood cell cancer, a skin cancer or a bladder cancer.

In a third aspect of said third embodiment, said targeting moiety comprises one member of a binding pair.

In a first item of said third aspect of said third embodiment, said one member of a binding pair comprises an antibody or antigen-binding portion thereof.

In a fourth embodiment, a composition comprises at least two populations of LNP's, a first population comprising an mRNA encoding an epitope; and a second population comprising an mRNA encoding an adjuvant.

In a first aspect of said fourth embodiment, said epitope is expressed on a pathogen.

In a first item of said first aspect of said fourth embodiment, said pathogen is a hepatitis virus.

In a second item of said first aspect of said fourth embodiment, said pathogen is *Bordatella pertussis, Corynebacterium diptheriae* or *Clostridium tetani.*

In a third item of said first aspect of said fourth embodiment, said pathogen is an influenza A virus or an influenza B virus.

In a fourth item of said first aspect of said fourth embodiment, said pathogen is a measles virus, a mumps virus or a rubella virus.

In a fifth item of said first aspect of said fourth embodiment, said pathogen is a respiratory syncytial virus.

In a sixth item of said first aspect of said fourth embodiment, said pathogen is a cytomegalovirus.

In a seventh item of said first aspect of said fourth embodiment, said pathogen is a SARS-COV-2 virus.

In a second aspect of said fourth embodiment, said epitope is expressed on a cancer cell.

In a first item of said second aspect of said fourth embodiment, said cancer cell comprises a lung cancer, a breast cancer, a prostate cancer, a colorectal cancer, a white blood cell cancer, a skin cancer or a bladder cancer.

In a third aspect of said fourth embodiment, said adjuvant comprises a first member of a binding pair, wherein a second member of said binding pair comprises a cell surface molecule that activates an immune cell.

In a first item of said third aspect of said fourth embodiment, said immune cells comprises an antigen presenting cell.

In a second item of said third aspect of said fourth embodiment, said cell surface molecule comprises a pattern recognition receptor.

Additional features and advantages of the instant disclosure are described in, and will be apparent from, the following Detailed Description.

DETAILED DESCRIPTION

Features and advantages of the instant invention may be understood more readily, by those of ordinary skill in the art, from reading the following detailed description. It is to be appreciated that certain features of the invention, which are described above and below, in the context, at times, of separate embodiments, also encompass features, aspects, embodiments and so on in combination in a single embodiment. Conversely, various features of the invention that are, for brevity, described in the context of a single embodiment, encompass those features, aspects, descriptions and the like separately or may be provided in any combination or sub-combination.

Definitions

Terms used herein generally are known in the art, for example, as described in Leuenberger et al., eds., Helv Chim Acta, Basel, CH (1995). Terms used herein include grammatic forms and variants thereof.

Practice of the instant invention employs, unless otherwise indicated, conventional methods of chemistry, bio-chemistry, cell biology, immunology, molecular biology and so on, provided, for example, in, "Molecular Cloning: A Laboratory Manual," Sambrook et al., eds., Cold Spring Harbor Laboratory Press, Cold Spring Harbor, NY, 1989; "Selected Methods in Cellular Immunology, Mishell & Shiigi, WH Freeman, Oxford, UK; and "Immunological Methods," Lefkovits & Pernis, eds., Academic Press.

1. References in the singular also may include the plural (for example, "a" and "an" may refer to one, or one or more) unless the context specifically states otherwise.

2. Use of numerical values in ranges specified herein, unless expressly indicated otherwise, are stated as approximations as though minimum and maximum values of stated ranges may both be preceded by the word, "about." In that manner, slight variations above and below the stated ranges can be tolerated to achieve substantially the same results as for values within ranges in practice of the instant invention. Disclosure of ranges is intended as continuous with that disclosed range including every value (of the same degree of accuracy of the two range limit values) between the minimum and maximum values and including the cited minimum and maximum values. Hence, the range 1-3 includes, 1, 2 and 3; and the range 1.4-1.7 includes 1.4, 1.5, 1.6 and 1.7.

The term, "about," means greater or less than a value (includes all values within a range to the same degree of accuracy as of the range limit values) stated by 1/10 of the stated value, but is not intended to limit any value or range of values. For instance, a concentration value of about 30% means a concentration between 27% and 33%. Each value or range of values preceded by, "about," is intended to encompass an embodiment of a stated absolute value and a range of values.

3. The instant disclosure provides, in embodiments, compositions comprising, "RNA," (for example, mRNA) poly-nucleotides encoding an antigenic polypeptide, for example, a parainfluenza virus (HPIV) antigenic polypeptide, a respiratory syncytial virus (RSV) antigenic polypeptide, a measles virus (MeV) antigenic polypeptide, a β coronavirus (BCOV) antigenic polypeptide, for example, MERS-COV, SARS-COV and so on, a cytomegalovirus (CMV) antigenic polypeptide, a hepatitis C (HCV) antigenic polypeptide, a Dengue virus antigenic polypeptide and so on (see, for example, Esper et al., Emerg Infect Dis 12 (5), 2006; and Pyrc et al., J Virol 81 (7): 3051-57, 2007, the content of each of which is incorporated by reference herein in entirety).

The instant disclosure also provides, in embodiments, combination compositions comprising at least two RNA polynucleotides encoding at least two polypeptides, such as, antigenic polypeptides of influenza A and of influenza B, and so on, which are encoded by at least two separate mRNA polynucleotides.

In embodiments, a polypeptide of interest, such as, an antigenic polypeptide (of, for example, an HPIV, RSV, CMV, HCV, influenza, BCoV and so on) encoded by a polynucleotide of interest is longer than 25 amino acids and shorter than 50 amino acids; in embodiments, greater than 50 amino acids in length. "Polypeptides," include gene products, naturally occurring polypeptides, synthetic polypeptides, homologs, orthologs, paralogs, fragments, variants, analogs and the like thereof, and other equivalents that are amino acid polymers. A polypeptide may be a single molecule or may be a complex, such as, a dimer, a trimer, a tetramer and so on. Polypeptides also may comprise single chain polypeptides or multichain polypeptides, such as, antibodies or insulin, and may be associated with or linked to one another. Polypeptide also may apply to an amino acid polymer comprising at least one amino acid residue which is an artificial chemical analogue or derivative of a corresponding naturally-occurring amino acid; or is a modified form thereof.

4. "Polynucleotide," include, but are not limited to, one or more of deoxyribonucleic acid (DNA), ribonucleic acid (RNA), including messenger mRNA (mRNA), and hybrids thereof. "Messenger RNA," (mRNA) refers to any poly-nucleotide comprising ribonucleotides that encodes a poly-peptide and is translated to produce an encoded polypeptide in vitro, in vivo, in situ or ex vivo. A polynucleotide is a base or nucleotide polymer.

Any one region of a nucleic acid may include one or more, "alternative," components (for example, an alternative nucleoside and so on). For example, a coding region (open reading frame, ORF), 5' UTR, 3' UTR or cap of an mRNA may include an alternative nucleoside, such as, a 5-substi-tuted uridine (for example, 5-methoxyuridine and so on), a 1-substituted pseudouridine (for example, 1-methyl-pseudouridine, 1-ethyl-pseudouridine and so on), a 5-sub-stituted cytidine (for example, 5-methyl-cytidine and the like) and so on.

Use of an alternative, such as, pseudouridine and so on, is tested for any positive or negative impact, such as, impeding amino acid addition, tRNA activity during translation, Eyler et al., PNAS 116 (46) 23068-23074, 2019; and so on.

An alternative component may impart useful properties, including increased stability, lack of substantial induction of an innate immune response of a cell to a polymer, for example, to a polynucleotide into which an alternate nucleo-tide is introduced; and so on. For example, an alternative polynucleotide or nucleic acid (as used herein, an, "alterna-tive polymer," "alternate," or, "alternative," and grammatic forms thereof, relates to a polymer containing at least one alternative component, such as, an alternative monomer, such as, an alternative polynucleotide or nucleic acid, hence, can contain at least one alternative base, nucleotide or nucleoside, and exhibits, for example, reduced degradation in a cell into which an alternative polynucleotide or nucleic acid is introduced, relative to a corresponding unaltered (not containing an alternative component) polynucleotide or nucleic acid, and so on. An alternative species may enhance efficiency of protein production, may enhance intracellular retention of a polynucleotide, may enhance viability of contacted cells, may possess reduced immunogenicity and so on.

Generally, shortest length of a polynucleotide can be length sufficient to encode a dipeptide. Examples of dipep-tides include carnosine and anserine. A dipeptide also includes a two amino acid portion of a larger polypeptide.

But, an mRNA can be of any length, such as, greater than 30 nucleotides in length, greater than 35 nucleotides in length, at least 40 nucleotides in length, at least 45 nucleo-tides in length, at least 55 nucleotides in length, at least 50 nucleotides in length, at least 60 nucleotides in length, at least 80 nucleotides in length, at least 90 nucleotides in length, at least 100 nucleotides in length, at least 120 nucleotides in length, at least 140 nucleotides in length, at least 160 nucleotides in length, at least 180 nucleotides in length, at least 200 nucleotides in length, at least 250 nucleotides in length, at least 300 nucleotides in length, at least 350 nucleotides in length, at least 400 nucleotides in length, at least 450 nucleotides in length, at least 500 nucleotides in length, at least 600 nucleotides in length, at least 700 nucleotides in length, at least 800 nucleotides, at least 900 nucleotides, at least 1000 nucleotides, at least 1100 nucleotides, at least 1200 nucleotides, at least 1300 nucleotides, at least 1400 nucleotides, at least 1500 nucleotides, at least 1600 nucleotides, at least 1800 nucleotides, at least 2000 nucleotides, at least 2500 nucleotides, at least 3000 nucleotides, at least 4000 nucleotides, at least 5000 nucleotides in length, or greater than 5000 nucleotides in length.

5. "Domain," refers to a motif or portion of a polymer having one or more structural or functional characteristics or properties, for example, binding capacity and so on, serving as a site for protein-protein interaction, traverses cell membranes, is outside of a cell, a stem-loop structure and so on.

6. As to polypeptides, "site," is used synonymously with, "amino acid residue," or, "amino acid side chain." As to polynucleotides, "site," is used synonymously with, "base," or, "nucleotide." A site represents a position within a peptide or a polypeptide or within a polynucleotide, that may be modified, manipulated, altered, derivatized or varied.

7. "Termini," or, "terminus," refers to an end of a polymer, such as, a polypeptide or polynucleotide. Such end is not limited to a first or a final amino acid of a polypeptide or to a first or a last base of a polynucleotide, but may include additional amino acids or nucleotides in a terminal region. As known, polypeptides have both an N terminus (terminated by an amino acid with a free amino group ($NH_2$)) and a C terminus (terminated by an amino acid with a free carboxyl group (COOH)). Polynucleotides have a 5' terminus (commonly, with a phosphate group of the fifth carbon (using conventional numbering) of the sugar at an end of a nucleic acid) and a 3' terminus (commonly, with a hydroxyl of the third carbon of the sugar at the other end of the nucleic acid.)

8. A, "fragment," can include a polypeptide shortened by one or more amino acids at either or both N terminus and C terminus (truncated) as compared to amino acid sequence of an original (native) protein. A fragment may have a length of about 6 to about 20, or even more amino acids, for example, such as, fragments processed and presented with MHC class I molecules with a length of about 8 to about 10 amino acids, for example, 8, 9 or 10 (or 6, 7, 11 or 12 amino acids). Fragments processed and presented with MHC class II molecules can have a length of about 13 or more amino acids, for example, 13, 14, 15, 16, 17, 18, 19, 20 or even more amino acids.

Fragment includes a polypeptide missing one or more amino acids. A fragment may lack an amino and/or a carboxy terminal amino acid.

Fragment also applies to a nucleic acid with portions of a 5' and/or 3' terminus missing, or missing any intervening bases. A nucleic acid fragment is one missing one or more nucleotides as compared to a parent nucleic acid from which a fragment is obtained.

Protein and nucleic acid fragments, functional protein domains and homologous proteins and functional nucleic acids are within scope of biologic molecules of interest. For example, any protein fragment (a polypeptide one or more amino acid residues shorter than a reference polypeptide but otherwise identical) of a reference protein is included herein. Similarly, any nucleic acid fragment (a polynucleotide one or more bases shorter than a reference nucleic acid but otherwise identical) of a reference polynucleotide is included herein.

9. "Variants," of polypeptides are alternatives having an amino acid sequence that differs from an original sequence at one or more sites, such as, one or more substituted, inserted and/or deleted amino acid(s) and so on. Fragments and/or variants have same biologic function or specific activity as compared to a wild-type, original, parent full-length or native protein from which a fragment or variant is obtained; or a function or activity is increased or improved, such as, more specific, higher avidity, greater or broader cross reactivity and so on.

A variant of a protein or a peptide may have at least about 70%, 75%, 80%, 85%, 90%, 95%, 98% or about 99% amino acid identity over contiguous 10, 20, 30, 50, 75 or 100 amino acids of such protein or peptide. Generally, variants possess at least about 50% identity to a native sequence or a reference sequence, at least about 80% identity, at least about 90% identity, with or to a native sequence or a reference sequence, or greater percentage of identity.

For example, sequence tags, amino acids, such as, one or more lysines, and so on, can be are added to a polypeptide (for example, at N terminus and/or C terminus, or interstitially). Sequence tags can be used for polypeptide detection, purification, localization and so on. One or more lysine residues (whether alone or interspersed with another amino acid species, to create a Lys domain) can be used to increase peptide solubility, to allow for biotinylation, to enhance ubiquitinylation and so on.

Variant also applies to nucleic acids, having a base sequence differing from that of an original, founding sequence by at least one base.

10. "Derivative," is synonymous with variant or with alternate or alternative. Another synonym used herein is, "modified."

Nucleic acids and polynucleotides may include one or more alternative or modified components to yield a derivative or a variant, which can impart desired properties, such as, increased stability, reduced induction of an innate immune response and so on to a nucleic acid or polynucleotide of interest. An alternative species may enhance efficiency of protein production, enhance intracellular retention of polynucleotides, enhance viability of contacted cells, reduce immunogenicity and so on.

Polynucleotides and nucleic acids may include one or more modified (for example, altered or alternative) nucleobases, nucleosides, nucleotides or combinations thereof. Nucleic acids and polynucleotides can include any useful modification or alteration, such as, to a nucleobase, a sugar or an internucleoside linkage (for example, to a linking phosphate, to altering a phosphodiester linkage or linking to a phosphodiester backbone and so on). Alterations may be to RNA's or to DNA's, such as, substitution of a 2'-OH of a ribofuranosyl ring to 2'-H and so on.

A polynucleotide may contain from about 1% to about 100% alternative bases or nucleotides (either in relation to overall nucleotide content, or in relation or relative to one or more types of nucleobase, that is, any one or more of A, G, U or C), or any intervening percentage.

11. "Orthologs," refer to evolutional, "younger," genes evolved from a common ancestral gene by speciation. Orthologs generally retain same function over course of evolution.

12. "Analogs," include polypeptide variants that differ by one or more amino acid alterations, for example, substitutions, insertions, deletions and so on of amino acid residues, that retain or maintain one or more properties of or functions of a parent or starting polypeptide.

13. "Substitutional variants," when referring to polypeptides, are those that have at least one amino acid residue of a native or starting sequence replaced with a different amino acid at that same site or position. Substitutions may be single, where only one amino acid of a molecule is replaced, or may be multiple, where two or more (for example, 3, 4, 5 or more) amino acids of a molecule are replaced.

14. A, "conservative amino acid substitution," refers to substitution of an amino acid with a different amino acid of similar size, charge, polarity and so on. Examples of conservative substitutions include replacement of a non-polar residue, such as, isoleucine, valine, leucine and so on, for another non-polar residue; and so on. Substitution of a basic residue, such as, lysine, arginine histidine and so on, for another basic amino acid is another example. A goal is to have a substitution not alter substantially properties of a polypeptide.

15. A, "non-conservative substitution," includes, for example, substitution of a non-polar amino acid residue, such as, isoleucine, valine, leucine, alanine, methionine and so on, for a polar residue, such as, cysteine, glutamine, glutamic acid, lysine and so on; and the like. Such a change likely will alter a polypeptide.

16. "Identity," of sequences relates to percentage two sequences are identical or are same, actually or functionally, when aligned for maximal matching. If an insertion occurs in one sequence, gaps can be inserted in the other sequence to allow maximal alignment. If a deletion occurs in one sequence, gaps can be inserted to allow optimal alignment. Percentage of identity of two sequences is a function of number of identical positions divided by total number of matching positions including those positions which are only occupied in one sequence.

Percentage of which two sequences are identical can be determined using a mathematic algorithm, for example, algorithm of Karlin et al. (1993) PNAS, 90:5873-5877 or of Altschul et al. (1997) Nucleic Acids Res., 25:3389-3402.

Percent identity between two sequences can be determined using methods, such as, those described in, "Computational Molecular Biology," Lesk, ed., Oxford University Press, NY, 1988; "Biocomputing: Informatics and Genome Projects," Smith, ed., Academic Press, NY, 1993; "Sequence Analysis in Molecular Biology," von Heinje, Academic Press, 1987; "Computer Analysis of Data," Griffin & Griffin, eds., Humana Press, NJ, 1994; and "Sequence Analysis Primer," Gribskov & Devereux, eds., Stockton Press, NY, 1991; each of which is incorporated herein by reference in entirety.

Generally, variants of a particular polynucleotide or polypeptide have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to a particular reference polynucleotide or polypeptide as determined by a sequence alignment program and parameters described herein or as known to those skilled in the art. Additional such tools for alignment include those of the BLAST suite (Altschul et al. (1997) Nucl Acids Res 25:3389-3402) or the Smith-Waterman algorithm (Smith & Waterman (1981) J Mol Biol 147:195-197).

17. "Homology," refers to overall relatedness between nucleic acid molecules or between polypeptides. Molecules that share a threshold level of similarity or identity determined by alignment of matching residues are termed, "homologous." In embodiments, polymeric molecules are considered homologous if sequences thereof are at least about 25%, 30%, 35%, 40%, 45%, 50%, 55%, 60%, 65%, 70%, 75%, 80%, 85%, 90%, 95%, or 99% identical or similar. Two polynucleotide sequences are considered homologous if polypeptides encoded thereby are at least about 50%, 60%, 70%, 80%, 90%, 95%, or even 99% identical for at least one stretch of at least about 20 amino acids, or more. In embodiments, homologous nucleic acids are characterized by ability to encode a stretch of at least 4-5 uniquely specified amino acids. For polynucleotide sequences less than 60 nucleotides in length, homology is determined by ability to encode a stretch of at least 4-5 uniquely specified amino acids.

18. "Homologs," refer to a first amino acid sequence or nucleic acid sequence that is related to a second amino acid sequence or nucleic acid sequence, respectively. Homologs have a certain degree of similarity of structure or of function.

19. A, "pharmaceutically active RNA," is a RNA that encodes a pharmaceutically active peptide, polypeptide or protein (essentially, equivalent terms).

20. A, "pharmaceutically active peptide, polypeptide or protein," has a beneficial effect on or in a subject, such as, alleviating or mitigating an abnormal condition or a disease state when administered to a subject in a therapeutically effective amount and so on. Hence, a pharmaceutically active peptide, polypeptide or protein can have a curative or palliative property and may be administered to ameliorate, relieve, alleviate, reverse, delay onset of, lessen severity of one or more symptoms of a disease or disorder and so on. A pharmaceutically active peptide, polypeptide or protein may have prophylactic properties and may be used to delay onset of a disease or to lessen severity of such disease or pathologic condition. A pharmaceutically active peptide, polypeptide or protein may replace a deficient or absent polypeptide or protein, or may supplement a deficient polypeptide or protein, essentially providing a replacement therapy.

Pharmaceutically active peptides, polypeptides or proteins include pharmaceutically active fragments of a protein, peptide or polypeptide, as well as pharmaceutically active analogs of a peptide, polypeptide or protein of interest. Pharmaceutically active peptide, polypeptide or protein includes peptides, polypeptides and proteins that comprise an epitope.

Examples of pharmaceutically active proteins include, but are not limited to, cytokines, immune system proteins, such as, interleukins and so on; colony stimulating factors, erythropoietin, tumor necrosis factor (TNF), interferons, integrins, addressins, selectins, homing receptors, T cell receptors, immunoglobulins, soluble major histocompatibility complex antigens, single chain molecules that bind antigen derived from antibodies, immunologically active antigens, such as, bacterial antigens, parasitic antigens, viral antigens and so on; allergens, autoantigens, antibodies, hormones, growth factors, growth factor receptors, enzymes, cytochromes, receptors, binding proteins, transcription and translation factors; tumor growth suppressing proteins and the like.

21. "Subject," is an organism or entity that benefits from translating introduced messages of interest, transient expression thereof and polypeptides expressed thereby. Synonyms include, "recipient," "individual," "host," "patient," "person," and so on. Subject can be human.

22. "Transient," in terms of molecular biology, is known in transformation and molecular biology, and means is not stable or is not permanent. Stable usually means a nucleic acid (which may carry a transgene) incorporates into a host genome. Because the instant invention relates to use of mRNA which remains in cytoplasm, expression is of a measured and discrete period, so long as a message avoids inactivation or degradation by a cell.

As message is subject to degradation in a cell, polypeptide is produced only so long as a message evades host cell message degradation machinery. Longer mRNA molecules may have shorter functional half-lives, being susceptible to damage by mechanical manipulation and/or degradation by elements found in vivo and in cells.

23. "Exogenous," means not naturally occurring for or in that subject. A synonym may be, "manufactured." An exogenous molecule is one introduced into an organism.

24. "Alternative," or, "alternate," means a first entity is replaced by a second entity, such as, an amino acid substitution and so on. For example, an alternative includes an analog, a variant, a derivative, is modified and so on.

25. "Native," "naturally occurring," "wild type (or wild-type)," and so on, including other synonymous terms used herein, generally refer to a form, for example, a polynucleotide, a polypeptide and so on, found in nature. That form generally is not modified, altered or changed by human manipulation or intervention. In a population, naturally occurring polymorphism may exist by natural mutation and selection. Hence, there may be more than one wild-type form.

26. "Parent," "original," "founding," "starting," and, "reference," mean a form from which another is derived. A native, naturally occurring or wild type form ultimately is a parent, original or reference form. However, a parent, founding, original, starting or reference form is not always a native, naturally occurring or wildtype form.

27. "Does not contain," "absent from," "lacking," "missing," "lack of," "is free of," "not present," "not containing," "omitted," "absence of," "devoid," and grammatic forms thereof, as well as equivalent terms and phrases, describe a negative, that is, lack of or absence of an entity or item.

28. "Specific," when used in context of describing a term, such as, "strain-specific," "species-specific," disease-specific," "cancer-specific," "domain-specific," and so on, indicates a feature, property, characteristic and so on found, associated with or limited to, referring to the examples above, found only in a or that strain, only in a or that species, only in a or that disease, only in a or that cancer, and only in a or that domain, respectively. Specific is a term and concept recognized in Immunology. In embodiments, a synonym for specific is, "restricted." Restriction also is a term and concept recognized in Immunology, for example, the known concept of major histocompatibility complex (MHC), or molecule, restriction.

29. A, "binding pair," relates to two entities that bind one another. An example is antibody and cognate antigen. Another example is lectin and cognate carbohydrate or entity carrying a cognate carbohydrate. Another example is virus attachment molecule and cell surface molecule to which a virus attaches and gains entry into a cell, such as, in the case of SARS-COV-2, a binding pair would be spike protein receptor binding domain and ACE2; or put in another way, that binding pair is ACE2 and spike protein RBD or ACE2 and spike protein. Any one of the two members of a binding pair can be listed first, analogous to commutative property of addition. Put in another way, the pair is ACE2 and S1 subunit of a spike protein. Put in another way, the pair is ACE2 and spike protein. So ACE2 binds spike protein, spike protein S1 domain, spike protein RBD and so on. Thus, one member of a binding pair may be identified in plural ways, as an actual portion or domain binding the other member of a binding pair, may be carried in and by a variety of polypeptides, domains and the like, based on, for example, a secondary, a tertiary, a quaternary structure of a molecular entity; and so on. As another example, some lectins bind monosaccharides, disaccharides, trisaccharides and so on. A particular disaccharide that binds a particular lectin may be displayed on a plurality of molecules and cell types, such as, liver cells, adrenal gland cells, tumor cells and so on, all of which would bind that lectin.

30. "Antigenic polypeptide," is an amino acid polymer that carries, contains or comprises an epitope.

Background

1. Transient Expression

As mentioned above, suitable transient expression of a polypeptide in or by a host or host cell now is possible following introduction of a manufactured mRNA into that host or host cell, see, for example, U.S. Pat. Nos. 9,950,065 and 10,143,758, the content of each of which herein is incorporated by reference in entirety. Modifications of mRNA and new delivery vehicles enable mRNA to be used in prophylactic or therapeutic applications.

Expression of message is limited, so long as an mRNA is functional in cytoplasm, that can be about 2 days or less, about 1 day or less, about 23 hours or less, about 59 minutes or less, or fewer minutes.

mRNA's also are single stranded and more susceptible to damage, for example, by oxidation with a reactive oxygen; cleavage by a metal complex; cleavage or change by an enzyme; and so on. A single break or cleavage, for example, of a phosphodiester bond and so on, will render an mRNA ineffective for complete translation.

Because an mRNA of interest resides in cytoplasm, as with other message, an introduced mRNA is destined for degradation by exosomes, a decapping complex or other degradative pathway. Once decapped, or other signals for degradation are recognized, a message no longer is translated.

2. Immune System

An immune system comprises an innate immune system that provides an immediate but non-specific response, and an adaptive immune system where a more specific response is created to improve recognition of a particular epitope or an antigen.

Each of the two systems comprises humoral and cellular components.

An innate immune system may be activated by ligands of, for example, pathogen-associated molecular pattern (PAMP) receptors and so on, for example, toll-like receptors (TLR's) and so on; other auxiliary substances, such as, lipopolysaccharides, TNF-α, cytokines, monokines, lymphokines, interleukins, chemokines and so on; mRNA's, double stranded RNA, immunostimulatory nucleic acids, CpG DNA, antibacterial agents, anti-viral agents and so on. Products of cell death, cell stress or injury can activate damage-associated molecular pattern (DAMP) receptors triggering an innate response. An innate immune system response includes recruiting immune cells to sites of infection, for example, through production of chemical factors, including cytokines and so on; activation of complement; identification and removal of foreign substances present in organs and tissues; and so on. DAMPS's and PAMP's are pattern recognition receptors (PRR).

A first step of a specific adaptive immune response is activation of naive antigen-specific T cells or different immune cells able to induce an antigen-specific immune response following exposure to an antigen-presenting cell. That occurs generally in lymphoid tissue and organs through which, for example, naive T cells, course.

Antigen-presenting cells (APC) include dendritic cells, macrophages and B cells. Dendritic cells take up antigen by phagocytosis and micropinocytosis, and are stimulated by contact with, for example, a foreign antigen and so on, to migrate to local lymphoid tissue where dendritic cells differentiate into mature dendritic cells. Macrophages ingest particulate antigens, such as, bacteria, and are induced to express MHC molecules carrying epitopes. B cells bind and internalize soluble protein antigens.

T cells have different effector functions. Two classes of T cells are distinguished by expression of cell surface proteins, CD4 and CD8. Two types of T cells differ in class of MHC molecule recognized thereby. CD4$^+$ T cells bind MHC class II molecules and CD8$^+$ T cells bind MHC class I molecules. Epitope recognition occurs by expression of peptides comprising an epitope obtained from antigens of pathogens and so on with MHC antigens at cell surfaces of antigen presenting cells.

MHC class I molecules present peptides and epitopes of cytosolic and nuclear origin, for example, from ingested pathogens and so on, such as, viruses and so on, to CD8$^+$ T cells, which differentiate into cytotoxic T cells. MHC class I molecules bind peptides from proteins degraded in cytosol by a proteasome and transported in and by endoplasmic reticulum (ER).

CD4$^+$ T cells (CD4$^+$ helper T cells) recognize MHC class II molecules and activate other effector cells of an immune system. MHC class II molecules normally are found on B lymphocytes, dendritic cells and macrophages. Macrophages, for example, are activated to kill pathogens and B cells are activated to secrete immunoglobulin. MHC class II molecules bind peptides and epitopes of extracellular proteins that are ingested by a cell and are degraded in cytoplasmic endosomes or lysosomes.

However, other factors of generating an immune response must be considered outside of antigen processing and presentation of peptide by MHC antigens. Witness antibody that binds conformational epitopes. If not a random process arising from a non-specific activation of a full repertoire of antibody clones to identify those that fortuitously bind a conformational epitope, another activation process that enables a host immune system to recognize portions of a polypeptide that only when in a three dimensional configuration combine from disparate areas of a polypeptide to come together to form an epitope, must exist. Therefore, full length expression of a polypeptide that adopts a conformation found in nature is important for generating a thorough and robust immune response, such as, an antibody response, to a pathogen, diseased cell and so on.

Pathogens that accumulate in macrophage and dendritic cell vesicles stimulate differentiation of Th1 cells, whereas extracellular antigens tend to stimulate production of Th2 cells. Th1 cells activate microbicidal properties of macrophages and induce B cells to make IgG antibodies effective in opsonising extracellular pathogens for ingestion by phagocytic cells. Th2 cells initiate a humoral response by activating naive B cells to secrete IgM, and induce production of weakly opsonising antibodies, such as, IgG2 and IgG4, as well as IgA and IgE.

Activation of macrophages by T helper subset 1 (Th1) cells leads to removal of cells. Activation of B cells by both Th2 and Th1 cells results in antibody class switching driving immune response maturation.

As to viruses, a response favoring Th1 cells, characterized by Ig class switching and generation of cytotoxic and helper T cells can be desirable.

An, "adjuvant," is a pharmacologic or immunologic agent or composition that may enhance in a non-specific fashion immunogenicity of an antigen or suspected antigen. An adjuvant can be a carrier or auxiliary substance for agents, epitopes or immunogens and/or other pharmaceutically active compounds. Adjuvants generally non-specifically increase immunogenicity of antigens incorporated into or co-administered with an adjuvant. Adjuvants may be divided, for example, into immunopotentiators or antigenic delivery systems. Adjuvants enable an immune response or a more vigorous immune response to an antigen or suspected antigen.

An, "antigen," is a substance that is recognized by an immune system and triggers an immune response thereto, that is, for example, formation of antibodies or of antigen-specific T cells that recognize and bind antigen and so on. An antigen may be a protein, a polypeptide or a peptide.

An, "antigenic polypeptide," is a protein, a polypeptide or a peptide that comprises an antigen, an epitope or a determinant.

An, "epitope," is a portion of a protein, a polypeptide or a peptide that is bound by an antibody or a cell. A synonym is, "determinant." An antigen can comprise plural epitopes.

3. Endosomal Escape

Nanoparticles (as with naturally occurring particulates) usually (as compared to diffusion across a cell membrane) are endocytosed by cells ultimately to be contained within acidic lysosomal or other catabolic compartment for destruction. Thus, to engage a protein producing machinery of a cell, an mRNA cargo of an endocytosed LNP must escape unscathed from an acidic degradative environment of an entrapping lysosome into cytoplasm (Selby et al., infra) and from an LNP.

There is evidence cationic lipids or cationic polymers of an LNP have a role in endosomal escape. In an acidic environment within a lysosome, cationic lipids or cationic polymers have a positive charge. Such charge may drive ion flow across a lysosomal membrane leading to osmotic swelling ending with lysosomal or endosomal rupture. Alternatively, a cationic lipid or cationic polymer can interact with anionic lipids in lysosome or endosome membranes enabling an LNP to fuse to a lysosomal or an endosomal membrane resulting in discharge of LNP contents into cytoplasm, essentially an exocytosis-type event. Some cationic lipids can adopt conformations or configurations disruptive to membranes. Such cationic lipids and cationic polymers destabilize lysosomal or endosomal membranes. Deranged membranes lead to lysosomal or endosomal rupture.

Whatever the mechanism, an mRNA payload is discharged from a lysosome into cytoplasm of a cell thereby making that message cargo accessible to translation to produce a polypeptide of interest.

mRNA

A. Synthesis

1. Chemical

Solid phase methods and reagents for making mRNA are known and available commercially, for example, using a nucleic acid synthesizer (for example, Biolytic, Fremont, CA) (Wincott et al., NAR 23:2677-2684, 1998). Solid phase synthesis may yield oligonucleotides up to about 100 nucleotides (nt) in length. Fragments then can be ligated using known chemistries and reagents.

2. Enzymatic

Polynucleotides also can be synthesized using enzymes of nucleic acid synthesis known in the art, see, for example, Ausubel et al., "Current Protocols in Molecular Biology"

(Wiley Interscience, 1989); Maniatis et al., "Molecular Cloning: A Laboratory Manual" (Cold Spring Harbor Lab., NY, 1982); and U.S. Pat. No. 6,110,898, each of which herein is incorporated by reference in entirety.

An RNA may be generated, for example, by in vitro transcription and so on.

"Transcription," is a process wherein a DNA encoding an mRNA encoding a polypeptide of interest is transcribed by a cell or an in vitro reagent into RNA in presence of requisite reagents, such as, a DNA dependent RNA polymerase and ribonucleotides. Hence, "in vitro transcription," relates to a process where RNA is synthesized in vitro, for example, in a cell-free system, using appropriate cell extracts comprising necessary reagents and other requisite reagents, such as, a suitable buffer, ribonucleotides and the like, and so on.

Cloning vectors carrying and replicating a DNA of interest can be used for generating transcripts. A DNA template can include various control sequences to enable transcription, such as, a promoter, and so on. DNA template for in vitro transcription may be a cDNA obtained by reverse transcription of RNA.

In embodiments, in vitro transcription can utilize a T7 phage RNA polymerase, an SP6 phage RNA polymerase, a T3 phage RNA polymerase and so on, which are available commercially.

Methods for in vitro transcription are known in the art (see, for example, Geall et al. (2013) Semin Imm 25 (2): 152-159; and Brunelle et al. (2013) Meth Enz 530:101-14). Reagents used in such a method typically include: 1) a linearized DNA template with a promoter sequence that has binding affinity for a respective RNA polymerase; 2) ribonucleoside triphosphates (NTP's) of the four bases (adenine, cytosine, guanine and uracil) or any base analog or modified base; 3) optionally, a cap or cap analogue; 4) a DNA-dependent RNA polymerase that binds a promoter within a linearized DNA template; 5) optionally, a ribonuclease (RNase) inhibitor to inactivate any contaminating RNase; 6) optionally, a pyrophosphatase to degrade pyrophosphate, that may inhibit transcription; 7) $MgCl_2$, which supplies $Mg^{2+}$ ions as a co-factor for polymerase; and 8) a buffer to maintain a suitable pH. A reaction mixture also can contain an antioxidant (such as, dithiothreitol (DTT) and so on), a polyamine, such as, spermidine and so on, at optimal concentration.

3. Product Purification

It is believed to minimize activating a host immune system following administration of an LNP, that is, reduce immunogenicity of an mRNA, an encapsulated target message can be purified from reactants, incompletely transcribed message, improperly transcribed products, partly transcribed message, double stranded RNA, malformed mRNA molecules and the like of the in vitro transcription reaction. Hence, synthesized message can be exposed to a purification procedure, such as, chromatography, such as, gel filtration, high performance liquid chromatography and so on, see, for example, Kariko et al., NAR 39 (21) e142, 2011; dialysis and so on. Dialysis may remove only solvent and may not remove nucleic acids and reagents.

However, in embodiments, it may be desirable such, "contaminants," be retained in an mRNA preparation as non-specific activators, innate immune system inducers, adjuvants and so on of an immune system. Hence, for example, a double stranded RNA can bind to and activate a PAMP receptor, that enhances a host immune response, for example.

4. Size

In embodiments, mRNA's of interest are of a smaller, more manageable size, where transcription is rapid and a transcript is of size that does not expose an mRNA to potential fragmentation by shear or other manipulation encountered during a transcription exercise. A smaller transcript also minimizes fragmentation when a message is obtained from a transcription reaction and when packaged into an LNP. A smaller transcript ensures better or more efficient translation of an intact or complete polypeptide in vivo.

Hence, an mRNA of interest may not be more than about 1000 bases in length, no more than about 900 bases in length and so on.

Interest in working with a smaller message is balanced with a desired or needed polypeptide. Thus, in embodiments, multiple polypeptides can be expressed by a single message; a compound or conjugate comprising two or more different polypeptides for a desired purpose are encoded on a single message; a polypeptide comprising plural domains, such as, spike protein of SARS-COV-2, is expressed from a single message and so on. An mRNA of interest may, then, be greater than about 1000 nt in length, greater than 2000 bases, greater than 3000 bases, if not longer.

B. Components

1. Codon Optimization

One or more nucleotides of a codon can be changed to yield a more stable codon than a codon found in a wild-type version of a nucleic acid; to yield a codon favored in human and so on, for a desired purpose or function. For example, an inverse relationship between RNA stability and a higher number of cytidine (C) and/or uridine (U) residues is known. RNA devoid of C and U residues is stable to many RNases (Heidenreich et al., J Biol Chem 269, 2131-8 (1994)).

Generally, a higher GC content correlates with greater nucleic acid stability. Hence, codons carrying a greater number of G and/or C residues can be selected.

In embodiments, number of C and/or U residues in an mRNA is reduced. In embodiments, number of C and/or U residues is reduced by substitution of one codon (encoding a particular amino acid but with fewer or no C and/or U bases) for another codon encoding the same amino acid but containing one or more C and/or U bases; or replacing with a codon for substituting with a conservative amino acid (but containing fewer or no C and/or U bases and so on). Substitutions and modifications to a nucleic acid may be performed by methods known to one of ordinary skill in the art.

Constraints on reducing number of C and U residues in a sequence might be greater within a coding region of an mRNA as compared to in an untranslated region flanking an ORF.

Codon optimization, in embodiments, may be used to match codon frequencies in target and host organisms to ensure proper folding; bias GC content to increase mRNA stability or to reduce secondary structures; minimize tandem repeat codons or base runs that may impair gene construction or expression; customize transcriptional and translational control regions; insert or remove protein trafficking sequences; remove/add post translation modification sites in encoded protein (for example, glycosylation sites and so on); add, remove or shuffle protein domains; insert or delete restriction sites; modify ribosome binding sites and mRNA degradation sites; adjust translational rates to allow the various domains of the protein to fold properly; to reduce or to eliminate problem secondary structures within the polynucleotide and so on.

Codon optimization tools, algorithms and services are known in the art and include services, for example, from GeneArt (Thermo Fisher) or DNA2.0 (ATUM, Newark, CA).

In embodiments, a codon optimized sequence shares less than about 95% sequence identity, less than 90% sequence identity, less than 85% sequence identity, less than 80% sequence identity or less than about 75% sequence identity to a naturally-occurring or wild-type sequence.

In embodiments, a codon optimized sequence shares between about 65% and 85% (for example, between about 67% and about 85%, or between about 67% and about 80% and so on) sequence identity to a naturally-occurring sequence or a wild-type sequence. In embodiments, a codon-optimized sequence shares between about 65% and about 75%, or about 80% sequence identity to a naturally-occurring sequence or wild-type sequence.

Any portion of flanking regions, including none, may be codon optimized and any may independently contain one or more different structural or chemical alterations, before and/or after codon optimization.

2. Modified Bases mRNA's provided herein retain ability to be translated, thereby producing a functional protein or polypeptide within a target cell. But a message can be modified or stabilized for benefit (for example, mRNA stabilized against in vivo nuclease digestion or degradation and so on). Activity of a modified mRNA encoding a functional protein or enzyme can be prolonged. Similarly, a modified composition of the instant invention may have improved or enhanced translation of an mRNA.

Furthermore, quantity of functional protein translated by a target cell can be a function of quantity of nucleic acid delivered to a target cell and stability of such nucleic acid. To extent that stability of nucleic acids of the instant invention may be improved or enhanced, half-life, activity of a translated protein or polypeptide and dosing frequency of a composition may be extended.

Accordingly, nucleic acids provided herein can comprise at least one modification which confers increased or enhanced stability to a nucleic acid, including, for example, improved resistance to nuclease digestion in vivo and so on.

As used herein, the terms, "modification," "modified," and grammatic forms thereof relate to a nucleic acid provided herein, and include at least one alteration or modification that renders a nucleic acid, for example, more effective or more efficient, such as, more stable (for example, resistant to nuclease digestion and so on) than a wild-type or naturally occurring version of a nucleic acid, and so on.

As used herein, the terms, "stable," "stability," and grammatic forms thereof relate to nucleic acids of the instant invention, and refer to longer presence or incidence in a cell, such as, increased or enhanced resistance to degradation, for example, by nucleases and so on, for example, endonucleases or exonucleases which normally degrade such RNA in a cell and outside a cell, and so on; and the like. Increased stability can include, for example, less sensitivity to hydrolysis or other means of destruction, for example, by endogenous enzymes (for example, endonucleases, exonucleases and the like) and so on; or by conditions within a target cell or a tissue, and so on, and the like, thereby increasing or enhancing residence of such a nucleic acid in a target cell and in tissue space. A stabilized nucleic acid molecule provided herein demonstrates longer half-life relative to a naturally occurring, unmodified counterpart thereof (the wild-type version of a nucleic acid). Also contemplated by the terms, modification and modified are alterations or alternatives that improve or enhance translation of mRNA, including, for example, inclusion of sequences that function in initiation of translation. (Kozak, Nucl Acids Res 15(20) 8125-48, 1987); and so on.

Exemplary modifications to a nucleic acid include removal of a base (for example, by deletion of or by substitution of one nucleotide for another and so on) or modification of a base, for example, chemical modification of a base and so on. "Chemical modification," includes modifications that introduce chemistries that differ from those seen in naturally occurring nucleic acids, for example, covalent modifications, such as, introduction of modified nucleotides, (for example, nucleotide analogs, inclusion of pendant groups which are not naturally found in nucleic acids and the like) and so on.

Modification also includes, for example, incorporation of non-nucleotide linkages or modified nucleotides into nucleic acid sequences of the instant invention (for example, modifications to one or both 3' and 5' ends of an mRNA molecule encoding a functional protein or polypeptide and so on). Such modifications include addition of bases to a nucleic acid sequence (such as, inclusion of a poly A tail or a longer poly A tail), alteration of the 3' UTR and/or the 5' UTR, complexing a nucleic acid with an agent (for example, a protein, a complementary nucleic acid molecule and so on); inclusion of elements which change structure of a nucleic acid molecule (for example, which form secondary structures and the like); and so on.

"Pseudouridine," includes 3-methyl pseudouridine and 1-methylpseudouridine. The term also refers to a monophosphate, diphosphate or triphosphate carrying that base, or to any other pseudouridine known in the art. As provided herein, one or more uridine residues of an mRNA can be replaced by a pseudouridine residue. Various pseudouridine reagents are available commercially.

In embodiments, a modified nucleoside is a modified cytidine (C). In another embodiment, a modified nucleoside is a modified adenine (A). In another embodiment, a modified nucleoside is a modified guanine (G).

For purposes herein, nucleotide, nucleoside, base, nucleobase and so on are used interchangeably. Key for substantive or informational content is an actual particular nucleobase or a nitrogenous base at a site. Other names relate to forms and reagents carrying a particular nitrogenous base and differ at sugar and phosphate sites. Hence, a particular name and form for any particular use is known to an artisan. For example, a nucleoside of a nitrogenous base and sugar can be viewed as a monomer of a nucleic acid polymer and a nucleotide, a nucleoside carrying a phosphate group can be a reactant for making a nucleic acid polymer.

In embodiments, between about 0.1% and about 100% of residues in an RNA of the instant invention are modified, either by presence of pseudouridine or another modified base; or other modification. In embodiments, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 10%, at least about 20%, at least about 30%, at least about 40%, at least about 50%, at least about 60%, at least about 70%, at least about 80% or at least about 90% of residues in a parent mRNA are replaced by modified bases, such as, a pseudouridine. In an embodiment, fraction or percentage is 100%.

A polynucleotide may or may not be uniformly altered along the entire length of a molecule. For example, one or more or all types of nucleotide (for example, purine or pyrimidine, or any one or more, or all of A, G, U and C, and so on) may be altered in a polynucleotide or nucleic acid, or in a given predetermined region thereof.

Modified bases may include, for example, one or more modifications of a base including addition of an alkyl, aryl, halo, oxo, hydroxyl, alkyloxy group, thio group and so on to a base; or addition of one or more fused or open rings to a base. A base can be oxidized or reduced, see, for example, U.S. Pat. No. 10,918,740, herein incorporated by reference in entirety.

Thus, an alternative polynucleotide or nucleic acid can exhibit longer half-life when introduced in vivo. An alternative polypeptide or nucleic acid can exhibit reduced degradation in a cell into which a polynucleotide or nucleic acid is introduced, relative to a corresponding unaltered polynucleotide or nucleic acid. An alternative species may enhance efficiency of protein production, may enhance intracellular retention of a polynucleotide; may enhance viability of contacted cells; may possess reduced immunogenicity, for example, by not triggering an innate immune response and the like; and so on. An induced innate immune response can lead to increased expression of inflammatory cytokines and termination of or reduction of translation of a message.

Because it is known a modified base can have a deleterious or negative effect on cell metabolism, in embodiments, an mRNA of interest does not contain any modified bases and hence, contains only naturally occurring A, G, C and U (Kallen et al., Hum Vacc Immunotherap 9 (10) 2263-2276, 2013).

3. 5' Cap

A, "5' cap," or, "cap," is a modified nucleotide, such as, a guanine and so on, added to a 5' end of an mRNA. A 5' cap can be added using a 5'-5' triphosphate linkage. Other examples of caps are known.

A 5' cap structure may be formed in chemical RNA synthesis or formed in an in vitro transcription reaction. A cap structure may be formed in vitro using capping enzyme, for example, using a commercially available capping kit.

A, "cap analogue," refers to a non-polymerizable nucleotide that has cap functionality by facilitating translation or localization and/or preventing degradation of an RNA when incorporated at a 5' end of a molecule. "Non-polymerizable," means a cap analogue can be incorporated only at a 5' terminus and therefore cannot serve as a site of extension of a growing message by a template-dependent RNA polymerase.

Cap analogues include those having a chemical structure of, m7GpppG, m7GpppA and m7GpppC (Stepinski et al., 2001, RNA 7 (10): 1486-95), where m7 is 7-methyl.

A 5' cap is involved in increasing polynucleotide stability. A cap binds an mRNA cap binding protein (CBP) responsible for polynucleotide stability in a cell and translation competency through association of CBP with a poly-A binding protein to form a mature cyclic mRNA structure. A cap further assists in removal of 5' proximal introns during mRNA splicing, see, U.S. Pat. No. 8,519,110, the entire content of which herein is incorporated by reference in entirety.

Because polynucleotides may be capped post-transcriptionally, and because that process can be more efficient, nearly 100% of polynucleotides may be capped, post-translation capping may be useful. That is in contrast to about 80% efficiency when a cap analog is linked to a polynucleotide in an in vitro transcription reaction.

4. 5' Untranslated Region (UTR)

In embodiments, a nucleic acid encoding a protein can be modified by incorporation of 3' and/or 5' untranslated (UTR) sequences.

In embodiments, 3' and/or 5' flanking UTR's that naturally flank an mRNA encoding an unrelated protein can be incorporated into an mRNA of interest encoding a therapeutic or functional protein of interest. Also, a 3' or a 5' UTR of a stable mRNA encoding an unrelated protein, for example, globin, actin, tubulin, histone, a citric acid cycle enzyme and so on, can be incorporated into a 3' and/or 5' region of an mRNA of interest to increase stability of an mRNA of interest.

Multiple 5' UTR sequences may be included in an upstream region and may be the same UTR or different UTR's.

5. Poly-Lysine (Lys) Domain

In embodiments, when a signal peptide coding sequence (see 6. below) is not present, to facilitate expressed cytosolic polypeptide processing into a proteasome, one, two, three or four Lys residues (poly-Lys or lysine domain) are added just 5' to an ORF to provide sites for ubiquitinylation. Lys residues can be contiguous or any adjacent Lys residues can be separated by 1-6 other amino acids, so long as a Lys domain does not disrupt translation or alter a polypeptide product of interest.

Ubiquitinylation of a polypeptide can direct that intracellular polypeptide to a degradation pathway. A ubiquitinylated polypeptide can be channeled to a proteasome where that polypeptide is digested into smaller fragments, some of which can be directed to associating with an MHC I polypeptide, destined for expression at cell surface.

6. Signal Peptide (SP)

In embodiments, when expressed, polypeptide secretion is desired, expressed polypeptides of interest do not contain a poly-Lys domain, but instead, comprise a signal peptide for secretion from a cell. Signal peptides, generally comprising N-terminal 15-60 amino acids of a protein, typically are needed for translocation of a translated polypeptide to a secretory pathway across a cell membrane. Signal peptides control entry of most proteins to a secretory pathway.

Signal peptides generally include three regions: an N-terminal region of varying length, which usually comprises positively charged amino acids; a hydrophobic region; and a short carboxy terminal peptide region.

A signal peptide of a nascent precursor protein (pre-protein) directs a ribosome to rough endoplasmic reticulum (ER) membrane and initiates transport of a growing peptide chain for processing. ER processing produces mature protein wherein signal peptide is cleaved from a precursor protein, typically by an ER resident signal peptidase. A signal peptide may remain uncleaved and function as a membrane anchor of a polypeptide at surface of a cell. A signal peptide is not responsible for final destination of a mature protein.

Some polynucleotides may comprise an artificial signal peptide operably linked to and in frame with a coding sequence of a polypeptide.

In embodiments, a signal peptide is fused to an N-terminus of a polypeptide. In embodiments, a signal peptide is fused to a C-terminus of a polypeptide.

In embodiments, an SP is obtained from an immunoglobulin, such as, an IgE signal peptide; an IgG signal peptide; and so on. In embodiments, a signal peptide is an Ig heavy chain (HC) epsilon-1 signal peptide (IgE HC SP), an IgG light chain signal peptide (IgGκ SP); a signal peptide of Japanese encephalitis virus prM protein; and so on. 7. Open Reading Frame (OFR)

An mRNA of interest encodes a coding sequence of a polypeptide, an ORF. An mRNA of the instant disclosure, in embodiments, comprises 1-10 (for example, 1, 2, 3, 4, 5, 6, 7, 8, 9 or 10) or more OPR's, each of which encodes a different polypeptide.

An ORF is a continuous stretch of nucleotides beginning with a start codon (for example, methionine (ATG)) and ending with a stop codon (for example, TAA, TAG or TGA). An ORF encodes a functional polypeptide of interest.

A coding sequence of an ORF can be codon optimized, may contain a modification, may contain a modified base and so on.

8. Poly-Lys Domain

As noted in 5. above, in embodiments, to facilitate expressed cytosolic polypeptide processing into a proteasome, a lysine domain of one, two, three or four Lys residues is added just 3' of an ORF to provide sites for ubiquit-inylation. Lys residues can be contiguous or any adjacent Lys residues can be separated by 1-6 other amino acids, so long as a Lys domain does not disrupt translation or function of an expressed polypeptide of interest.

9. 3' UTR

As disclosed in 4. above, a coding sequence can comprise a, "3' untranslated region," (3' UTR) that is just 3' down-stream from a stop codon of an ORF (that is, a codon of an mRNA transcript that signals termination of translation).

A 3' UTR of a polynucleotide may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55 or more than 60 amino acids.

10. Poly (A) Tail

A poly A tail is thought to stabilize message. Therefore, a longer poly A tail may render an mRNA more stable.

A poly A tail can be added using a variety of art-recognized techniques. For example, longer poly A tails can be added to synthetic or in vitro transcribed RNA using poly A polymerase (Yokoe et al., Nat Biotech, 1996; 14:1252-1256.) A transcription vector can encode a longer poly A tail. A poly A tail can be added by transcription directly from PCR products. A poly A tail may be ligated to a 3' end of an RNA with RNA ligase (see, for example, Sambrook et al., supra).

In embodiments, a poly A tail can be at least about 90, 200, 300, 400 at least about 500 nucleotides in length, or longer. In embodiments, length of a poly A tail is adjusted to control stability of an mRNA of the invention and, thus, translation of protein. For example, length of a poly A tail can be adjusted to modify level of resistance of mRNA to nucleases and mRNA stability.

11. Other

Other modifications can be made to an mRNA, such as, to one or both 3' and 5' ends of an mRNA. For example, modification of a 5' end of an mRNA can include a partial sequence of a cytomegalovirus (CMV) immediate-early 1 (IE1) gene, or a fragment thereof, to improve nuclease resistance, to improve half-life of an mRNA and the like; and so on. A sequence encoding human growth hormone (hGH), or a fragment thereof, for example, can be added to one or both 3' and 5' ends of an mRNA to stabilize a nucleic acid; and so on.

In embodiments, an mRNA may have one or more AU-rich sequences removed. Such sequences, sometimes referred to as, "AURES," are destabilizing sequences found in a 3 'UTR, see, for example, U.S. Pat. No. 10,702,600, incorporated herein by reference in entirety.

An mRNA may contain an internal ribosome entry site (IRES). An IRES may act as a ribosome binding site or may serve as one of multiple ribosome binding sites of an mRNA. A polynucleotide containing more than one func-tional ribosome binding site may encode several peptides or polypeptides translated independently by ribosomes.

Examples of an IRES include those from a polio virus (PV), a foot and mouth disease virus (FMDV), a hepatitis C virus (HCV), a murine leukemia virus (MLV), a simian immune deficiency virus (SIV) and so on.

A 5' UTR of a polynucleotide may include at least one translation enhancer element (TEE). The term, "translational enhancer element," refers to a sequence that increases amount of polypeptide or protein produced from an mRNA. A TEE may be located between a transcription promoter and a start codon.

In an embodiment, TEE's in a UTR promote translational activity of a polynucleotide whether during cap-dependent translation or cap-independent translation, Panek et al. (Nucl Acids Res, 2013, 1-10) and U.S. Pat. No. 9,868,692, herein incorporated by reference in entirety.

Lipid Nanoparticles (LNP)

Absent limitations of working with RNA, lipid-based formulations are a promising delivery vehicle for RNA due, in part, to biocompatibility and potential ease of large scale production (Akinc et al., Nat Biotech 26 (5) 561-569, 2008).

Cationic lipids have long been studied as synthetic mate-rials for delivery of RNA (Riley et al., Sci Adv 7: eaba1028, 2021). After mixing together, nucleic acids are condensed by or complexed with cationic lipids to form lipid/nucleic acid complexes or vehicles, known as LNP's or lipoplexes, see, for example, Pardi et al., J Control Rel 217:345-351, 2015. (Structure is not always determined and can vary. For example, an RNA may be contained within, generally, a spherical lipid shell (Leung et al., J Phys Chem 116:18440-18450, 2012); mRNA can be on or at a surface of spherical lipids (Blakney et al., Gene Therap 26:363-372, 2019); an mRNA may merely be associated or complexed with lipids in any structure; and so on.)

Lipoplexes protect nucleic acids from nucleases and thus, aid in delivery of an mRNA to and into cells. There, cationic lipids interact with a negatively charged endosome mem-brane and allow an mRNA to escape from an endosome into cytoplasm to engage translation machinery.

Lipoplexes can be prepared by directly mixing ionizable positively charged lipids at acidic pH with negatively charged nucleic acids, see, for example, Kulkarni et al., Nucl Acid Therap 28 (3) 146-157, 2018.

"Lipid," refers to a fatty acid derivative or other amphi-philic lipoidal compound capable of forming a lipid vesicle or particle. Generally, hydrophobic parts of lipids come together, such as, alkyl chains and so on, as do hydrophilic parts of an amphiphilic lipid, such as, head groups of fatty acids. Lipids can be neutral, anionic or cationic.

A hydrophobic domain of a lipid can have at least one or two alkyl chains, or a cholesterol moiety. Alkyl chains are not limited to a specific length, degree of saturation or number of double and triple bonds, and can have a length of 10 to 30, 14 to 25 carbon atoms, or shorter, or longer, with any of a number of double or triple bonds. A lipid may comprise two different fatty acids.

A lipid also can contain a polar, hydrophilic head group. Characteristics of a head group dictate charge of a lipid, that is, whether a lipid is anionic, neutral or cationic. A head group can comprise an amine, such as, a tertiary amine, a quaternary amine, a piperazine (Ramishetti et al., Adv Mat 32 (12) 1906128, 2020) or other charge-bearing group.

Ionizable cationic lipids can be used for making particles of interest. Charge of a lipid enables associating with anionic molecules, such as, nucleic acids. Ionizable lipids have a different charge at different pH. Suitable ionizable cationic lipids are those with a pKa of about 7, in embodiments about 6, in embodiments, from about 6.0 to about 6.7, in embodiments, from about 6.1 to about 6.6, in embodiments, from about 6.2 to about 6.5, but can be of other values.

As used herein, the term, "lipid nanoparticle (LNP)," refers to a vehicle comprising one or more lipids (for example, cationic lipids, non-cationic lipids and so on) formulated to deliver one or more mRNA's to one or more target cells or tissues. LNP includes a lipoplex. Generally, an LNP comprises an ionizable cationic lipid, optionally, one or more structural lipids and optionally, a PEGylated lipid.

Examples of suitable lipids include, for example, phosphatidyl compounds, for example, phosphatidylglycerol (PG), phosphatidylcholine (PC), phosphatidylserine (PS), phosphatidylethanolamine (PE) and so on; a sphingolipid (SL), a cerebroside (CER or Cer), a ganglioside and so on.

Also contemplated herein is use of non-lipid polymers for making particles. Suitable polymers include, for example, polyacrylates, polyalkycyanoacrylates, polylactides, poly-caprolactones, polylactide-polyglycolide copolymers, dextrans, an albumin, a gelatin, an alginate, collagens, chitosans, cyclodextrins, polyethylenimine (PEI) and so on. Some of such non-lipid polymers can contribute to endosome escape. Some of such non-lipid polymers have a pKa as desired herein.

Also contemplated herein are anionic lipids and non-lipid polymers, as such molecules are known to disrupt membrane depending on pH. For example, poly(propylacrylic acid) disrupts membranes by transforming to a hydrophobic form at endosomal pH and in that form disrupts endosomal membranes releasing an mRNA payload (Jones et al., Biochem J 372 (Pt 1) 65-75, 2003). An anionic lipid associates with an anionic nucleic acid and protects that nucleic acid until endocytosis.

In embodiments, an LNP vehicle may be selected and/or prepared to optimize delivery of an mRNA payload to a target cell, tissue or organ. For example, if a target cell is a hepatocyte, properties of a vehicle (for example, size, charge, pH, composition and so on) may be optimized to deliver an LNP selectively to liver, to reduce immune clearance, to promote retention in liver and so on. Alternatively, if a target tissue is central nervous system (for example, mRNA administered for treatment of a neurodegenerative disease may specifically target brain or spinal tissue), selection and preparation of an LNP considers penetration of, and retention within the blood brain barrier.

Lipoplexes and LNP's have some advantages over current drug delivery vehicles. For example, an LNP need not require an adjuvant as does a protamine carrier. LNP's enable delivery of chemically modified mRNA. (Maurer & Kulkarni, Pharm Rev 27 Aug. 2019; and Cross, CEN 99 (8), 2021).

An LNP can comprise a cationic lipid, such as, N-[1-(2, 3-dioleyloxy) propyl]-N,N,N-trimethyammonium chloride (DOTMA) and so on, and two structural lipids comprising cholesterol (CHOL) and phosphatidyl choline (PC) having molar ratios, such as, for a formulation of DOTMA/CHOL/PC, in relative ratios of 10/50/40, 20/50/30, 30/50/20, 40/50/10 or 50/50/0.

An LNP carrying an siRNA is an approved drug. That LNP contains PEG. It might be expected those lipoplexes carrying an siRNA and comprised in part of PEG, can cause an inflammatory reaction associated with a transient IgM response (Kozma et al., ACS Nano 13:9315-9324, 2019 and de Oliveira Viana et al., Acta Pharm *Sinica* B 11 (4) 852-870, 2021), perhaps directed to PEG.

As used herein, "N/P ratio," is molar ratio at about physiologic pH of nitrogen atoms in a lipid to phosphate groups in an mRNA, for example, in a nanoparticle composition including lipids and an mRNA.

In general, a lower N/P ratio can be about 2:1 to about 30:1, such as, 2:1, 3:1, 4:1, 5:1, 6:1, 7:1, 8:1, 9:1, 10:1, 12:1, 14:1, 16:1, 18:1, 20:1, 22:1, 24:1, 26:1, 28:1 or 30:1. In embodiments, N/P ratio may be from about 2:1 to about 8:1, from about 5:1 to about 8:1, about 5.0:1, about 5.5:1, about 5.67:1, about 6.0:1, about 6.5:1, about 7.0:1 and so on. N/P ratio can be in the range of about 0.01-4, 0.01-2, 0.1-2, 0.1-1.5 and so on, about 0.1-1 and so on. For example, N/P ratio may be about 5.67:1, see U.S. Pat. No. 9,868,692.

N/P ratio of an at least one RNA and a cationic or polycationic compound may be calculated from N/P ratio of all those components, which, in general, is molar ratio of cationic to anionic material (Metwally et al., Pharmaceut 3:125-140, 2011). For example, 1 μg RNA typically contains about 3 nmol phosphate residues. There are a number of different ways to calculate N/P ratio.

Nanoparticle compositions may be characterized by any of a variety of methods. For example, microscopy (for example, transmission electron microscopy, scanning electron microscopy and so on) may be used to examine morphology and size distribution of a nanoparticle composition. Dynamic light scattering or potentiometry (for example, potentiometric titration and so on) may be used to measure ξ potential. Dynamic light scattering also may be used to determine particle size. Instruments, such as, Zetasizer Nano ZS (Malvern Instruments Inc., Westborough, MA), may be used to measure multiple characteristics of a nanoparticle composition, such as, particle size, polydispersity index, ξ potential and so on.

A nanoparticle composition may be relatively homogenous. A polydispersity index may be used to ascertain homogeneity of a nanoparticle composition, for example, size distribution of nanoparticles and so on. A small (for example, less than 0.3 and so on) polydispersity index generally indicates a narrow particle size distribution. A nanoparticle composition may have a polydispersity index from about 0 to about 0.25, such as, about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24 or 0.25. In embodiments, polydispersity index of a nanoparticle composition may be from about 0.10 to about 0.20.

ξ potential of a nanoparticle composition may be used to determine electrokinetic potential of a particle. For example, ξ potential may describe surface charge of a nanoparticle and so on. Nanoparticles with relatively low charge, positive or negative, generally are desirable, as more highly charged species may interact undesirably with cells, tissues and other elements in vivo. In embodiments, ξ potential of a nanoparticle may be from about −10 m V to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, from about +5 mV to about +10 mV and so on.

Efficiency of encapsulation of a therapeutic and/or pro-phylactic mRNA describes amount of mRNA encapsulated or otherwise associated with a nanoparticle after prepara-tion, relative to initial amount provided. Encapsulation effi-ciency is desirably high (for example, close to 100%). Encapsulation efficiency may be measured, for example, by comparing amount of mRNA in a solution containing a nanoparticle before and after dissociating that nanoparticle with one or more organic solvents or detergents. Fluores-cence may be used to measure amount of free mRNA in solution. For nanoparticles, encapsulation efficiency of an mRNA may be at least about 50%, for example, about 50%, 55%, 60%, 65%, 70%, 75%, 80%, 85%, 90%, 91%, 92%, 93%, 94%, 95%, 96%, 97%, 98%, 99%, or 100%. In embodiments, encapsulation efficiency may be at least about 80%. In embodiments, encapsulation efficiency may be at least about 90%.

Characteristics of a nanoparticle may depend on compo-nents thereof. For example, a nanoparticle including cho-lesterol may have different characteristics from a nanopar-ticle containing a different structural lipid. Similarly, characteristics of a nanoparticle may depend on absolute or relative amounts of components. For example, a nanopar-ticle including a higher molar fraction of a phospholipid may have different characteristics from a nanoparticle including a lower molar fraction of a phospholipid. Characteristics also may vary depending on method and conditions of nanoparticle preparation.

A nanoparticle optionally may comprise one or more coatings. For example, a nanoparticle may be formulated in a capsule, film or tablet having a coating. A capsule, film or tablet including an LNP described herein may have any useful size, tensile strength, hardness or density.

Another coating may be one of a targeting entity on a surface of an LNP, such as, a receptor or a receptor ligand, a lectin or a lectin receptor, a binding portion of an antibody, an aptamer, a Spiegelmer, a lectin and so on, see, for example, Rosenblum et al., Sci Adv 6: eabc9450, 2020, essentially, a surface coating can comprise a member of a binding pair.

A binding pair other than an antibody and antigen pair is a receptor and a ligand, such as, apolipoprotein E (ApoE) and a lipoprotein receptor, commonly found in liver; and so on. Hence, binding ApoE to a surface of an LNP provides a tool for delivery of an LNP to liver (Veiga et al., Nat Comm 9:4993, 2018).

In embodiments, targeting of antigen presenting cells (APC) is desired, which can be obtained by coating an LNP with an antigen binding polypeptide, such as, an scFv, and so on; where the antigen is specific for an APC, such as, a C-C chemokine receptor, CD80, CD205, CD370 and so on, for example. In embodiments, a coating on an LNP is a binding partner of a cell surface molecule specific for an APC, such as, one of CCL1-CCL28, CD28, a CpG oligo-nucleotide and so on.

A targeting moiety can be joined to a site on an LNP surface, such as, anchored to a lipid. For example, a C terminal Cys of a single chain antibody was attached to a lipoidal ethanolamine on an LNP surface using maleimide chemistry (Katakowski et al., Mol Therap 24 (1) 146-155, 2016). In embodiments, a targeting moiety can be joined to a surface amine group, such as, of a Lys and so on, of an LNP using N-hydroxysuccinimide (NHS) chemistry.

1. Structural Lipid

"Structural lipid," refers to a lipid for forming a lipid particle, such as, a cationic lipid nanoparticle. A structural lipid can be neutral, positively charged or negatively charged. Generally, structural lipid makes up bulk of an LNP. In embodiments, structural lipid(s) is (are) neutral or negatively charged.

When used in combination with a cationic lipid, structural lipid(s) may comprise a molar ratio of about 5% to about 90%, from about 10% to about 70% and so on, of total lipid present in an LNP.

More than one type of structural lipid may be found in an LNP.

A structural lipid may include a phospholipid or deriva-tives thereof, a sphingolipid or derivatives thereof, a gly-colipid or derivatives thereof, a cholesterol and so on.

"Anionic lipid," refers to a lipid carrying a net negative charge at a selected pH, such as, physiologic pH.

"Non-cationic lipids," include, but are not limited to, distearoylphosphatidylcholine (DSPC), dioleoylphosphati-dylcholine (DOPC), dipalmitoylphosphatidylcholine (DPPC), dioleoylphosphatidylglycerol (DOPG), dipalmi-toylphosphatidylglycerol (DPPG), dioleoylphosphatidyle-thanolamine (DOPE), palmitoyloleoylphosphatidylcholine (POPC), palmitoyloleoyl-phosphatidylethanolamine (POPE), dipalmitoyl phosphatidyl ethanolamine (DPPE), dimyristoylphosphoethanolamine (DMPE), distearoyl-phos-phatidyl-ethanolamine (DSPE), 1-stearoyl-2-oleoyl-phos-phatidyethanolamine (SOPE), cholesterol (CHOL or Chol) or a mixture thereof.

A structural lipid can comprise alkyl moieties from 14-18 carbon atoms, from 16-18 carbon atoms, from 10-14 carbons and so on. In embodiments, an alkyl chain is saturated.

Cholesterols (CHOL or Chol) can be used either alone, with another structural lipid or in combination with other cationic or non-cationic lipids. Suitable cholesterol-type cationic lipids include, for example, Chol, DC-Chol (N,N-dimethyl-N-ethylcarboxamidocholesterol) (Gao et al., Biochem Biophys Res Comm 179, 280 (1991); Wolf et al., BioTechniques 23, 139 (1997); and U.S. Pat. No. 5,744, 335); and so on.

Phospholipids may include a phospholipid moiety and one or more fatty acid moieties. A phospholipid moiety may be phosphatidyl choline (PC), phosphatidyl ethanolamine (PE), phosphatidyl glycerol (PG), phosphatidyl serine (PS), phosphatidic acid (PA), 2-lysophosphatidyl choline or a sphingomyelin (SM).

A fatty acid moiety may be lauric acid, myristic acid, myristoleic acid, palmitic acid, palmitoleic acid, stearic acid, oleic acid, linoleic acid, α-linolenic acid, erucic acid, phytanoic acid, arachidic acid, arachidonic acid, eicosapen-taenoic acid, behenic acid, docosapentaenoic acid, docosa-hexaenoic acid and so on.

A phospholipid may be a glycerophospholipid. Examples of a glycerophospholipid include phosphatidylglycerol (PG), including dimyristoyl phosphatidylglycerol (DMPG) and so on; phosphatidylcholine (PC), egg yolk PC and dimyristoyl PC (DMPC); phosphatidic acid (PA), phospha-tidylinositol (PI), phosphatidylserine (PS), phosphatidyle-thanolamine (PE), sphingomyelin (SM) and derivatives thereof and so on. PC does not destabilize endosomal membranes but stabilizes an LNP during formation (Semple et al., infra).

A phospholipid may be functionalized with or cross-linked with one or more alkynes (for example, an alkenyl group in which one or more double bonds are replaced with a triple bond). Under appropriate reaction conditions, an alkyne group may undergo a copper-catalyzed cycloaddition on exposure to azide. Such a reaction may be used to functionalize a phospholipid of a nanoparticle to facilitate membrane permeation, cellular recognition or in conjugating a targeting moiety or coating to or onto a nanoparticle.

Phospholipids include 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1-oleoyl-2-cholesterylhemisuccinoyl-sn-glycero-3-phosphocholine, 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG) and sphingomyelin.

2. Ionizable Cationic Lipid

Cationic lipids, such as, DOTAP (1,2-dioleoyl-3-trimethylammonium-propane), DOTMA (N-[1-(2,3-dioleoyloxy) propyl]-N,N,N-trimethyl-ammonium methyl sulfate) and so on can form particles or lipoplexes with mRNA by electrostatic interaction (Leung et al., supra). Cationic lipids protect RNA payloads from RNase degradation even when RNA is at a surface of an LNP (Blakney et al., supra).

Cationic or polycationic compounds include cationic polysaccharides, for example, chitosan and so on, polybrene, cationic polymers, for example, polyethyleneimine (PEI) and so on, cationic lipids, for example, DOTMA: [1-(2,3-sioleyloxy) propyl)]-N,N,N-trimethylammonium chloride, dioleyl phosphatidylethanolamine; DOGS: dioctadecylamidoglicylspermin, DIMRI: dimyristo-oxypropyl dimethyl hydroxyethyl ammonium bromide, DOTAP: dioleoyloxy-3-(trimethylammonio) propane or DC-6-14: O,O-ditetradecanoyl-N-(α-trimethylammonioacetyl) diethanolamine chloride and so on; cationic or polycationic polymers, for example, modified polyaminoacids and so on, such as, β-amino acid polymers and so on; modified polyethylenes, such as, polyvinyl pyrrolidone (PVP) and so on; modified acrylates, such as, PDMAEMA (poly(dimethylaminoethyl methylacrylate) and so on; modified amidoamines, such as, PAMAM (poly(amidoamine) and so on; a dendrimer, such as, a polypropylamine dendrimer, a PAMAM dendrimer and so on; a polyimine, such as, PEI and poly(propyleneimine) and so on; a polyallylamine; a sugar polymer, such as, a cyclodextrin, a dextran, a chitosan and the like; and so on.

The term, "cationic component," typically refers to a positively charged (cation) molecule at a pH value of typically about 1 to about 9, a pH value of or below about 9 (for example, 5 to 9), of or below about 8 (for example, 5 to 8), of or below about 7 (for example, 5 to 7), at physiologic pH values, for example, about 7.3 to 7.4.

A polar head group of a cationic lipid can comprise an amine, such as, a primary, a secondary, a tertiary amine, quaternary ammonium, various combinations of amines, amidinium salts, guanidine group, imidazole group, as well as pyridinium, piperazine and amino acid head groups, such as, lysine, arginine, ornithine, tryptophan and so on.

A head group of a cationic lipid may comprise multiple cationic charges.

Cationic lipids include 1,2-dimyristoyl-sn-glycero-3-ethylphosphocholine (DMEPC), 1,2-di-O-octadecenyl-3-trimethylammonium propane (DOTMA), 1,2-dioleoyl-3-trimethylammonium propane (DOTAP), 1,2-dimyristoyl-3-trimethylammonium propane (DMTAP), 2,3-di (tetradecoxy) propyl-(2-hydroxyethyl)-dimethylazanium bromide (DMRIE), didodecyl(dimethyl) azanium bromide (DDAB) or 1,2-dioleyloxypropyl-3-dimethyl-hydroxyethyl ammonium bromide (DORIE).

A cationic head group is charged at lower pH (when an LNP is constructed) but neutral at higher, physiologic pH, hence, is ionizable. pKa of a cationic lipid should be low enough to prevent an LNP from having a high positive charge at physiologic pH, and pKa should be high enough so a lipid has a positive charge form in an acidic, endosomal environment of a lower pH value.

A cationic lipid can interact with anionic lipids in an endosome and can destabilize an endosome membrane to permit LNP payload or cargo escape or release from an endosome into cytoplasm. Structural lipids which can enhance entry of LNP's into cells also may destabilize an endosomal membrane (Hafez et al., Gene Therap 8:1188-1196, 2001).

Semple et al. constructed a combinatorial library of cationic lipids for RNA delivery by LNP's (Nat Biotech 28 (2) 172-178, 2010). Hypothesizing head groups of cationic lipids interact with endosomal anionic lipids to form membrane disrupting structures, Semple et al. found acyl groups with two double bonds were beneficial. A linker between a head group and acyl chains increased molecular flexibility and ability to disrupt membranes. Rats injected at 5 mg/kg expressed payload in liver and spleen after 30 minutes. In non-human primates, a dose of 0.1 mg/kg was effective.

Independently, it was observed hydrophobic chains of a cationic lipid can be relatively unsaturated to promote lipid bilayer destabilization. Kulkarni et al., Nucl Acid Therap (28) 146-157, 2018; and Heyes et al., J Control Rel 107 (2) 276-287, 2005.

A portion of the at least one cationic lipid in an LNP amounts to at least about 10%, at least about 20%, at least about 30%, at least about 40%, at least about 50%, at least about 60%, at least about 70%, at least about 80%, at least about 90%, or 100% of lipids in an LNP.

Cationic lipids are described in the scientific and patent literature, many of which are commercially available, such as, DOTMA (Feigner et al., PNAS, 84, 7413 (1987) and U.S. Pat. No. 4,897,355) and so on. DOTMA can be formulated with DOPE.

Other suitable cationic lipids include, for example, 5-carboxyspermylglycinedioctadecylamide (DOGS), 2,3-dioleyloxy-N-[2 (spermine-carboxamido) ethyl]-N,N-dimethyl-1-propanaminium (DOSPA) (Behr et al., PNAS, 86, 6982 (1989); U.S. Pat. Nos. 5,171,678; and 5,334,761), 1,2-dioleoyl-3-dimethylammonium-propane (DODAP), DOTAP, 1,2-distearyloxy-N,N-dimethyl-3-aminopropane (DSDMA), 1,2-dioleyloxy-N,N-dimethyl-3-aminopropane (DODMA), N-dioleyl-N,N-dimethylammonium chloride (DODAC), N,N-distearyl-N,N-dimethylammonium bromide (DDAB) and so on (Heyes et al., J Cont Rel 107:276-287 (2005); Morrissey et al., Nat Biotechnol 23 (8): 1003-1007 (2005).

Also contemplated are cationic lipids such as, dialkylamino lipids, imidazole lipids, guanidinium lipids and so on.

3. Lipid with Polyethylene Glycol (PEG)

Polyethylene glycol (PEG)-modified phospholipids and derivatized lipids (PEGylated), such as, PEG derivatized ceramides (PEG-CER) and so on, can be incorporated into LNP's of interest. A PEG chain can be up to 5 kDa in length covalently attached to a lipid with alkyl chain(s) of $C_6$-$C_{20}$ length.

Carbon chain length of a PEG lipid may be from $C_{14}$ to $C_{18}$, but may be shorter to alter pharmacokinetics of an LNP. In embodiments, a shorter chain length acyl chain is used.

A PEG lipid may be selected from PEG-modified phosphatidylethanolamines, PEG-modified phosphatidic acids, PEG-modified ceramides (CER or Cer), PEG-modified dialkylamines, PEG-modified diacylglycerols, PEG-modified dialkylglycerols and mixtures thereof. (Zukancic et al., Pharm 12:1068, 2020)

Example of PEGylated lipids include PEG-c-DOMG (R-3-[(ω-methoxy-poly(ethyleneglycol) 2000) carbamoyl)]-1,2-dimyristy-loxypropyl-3-amine), PEG-DSG (1,2-distearoyl-sn-glycerol, methoxypolyethylene glycol), PEG-DMG (1,2-dimyristoyl-sn-glycerol), PEG-DPG (1,2-dipalmitoyl-sn-glycerol, methoxypolyethylene glycol) and so on.

Addition of PEGylated components may prevent particle aggregation during LNP preparation and during LNP storage, (Klibanov et al. (1990) FEBS Lett, 268 (1): 235-237). PEGylated lipid may assist in controlling particle size during formation.

PEGylated components rapidly exchange out of an LNP in vivo (see U.S. Pat. No. 5,885,613). Exchangeable lipids include PEG-ceramides having shorter acyl chains (for example, $C_{14}$ to $C_{18}$), that may be beneficial (Suzuki et al., Int J Pharmaceut 588:119792, 2020.)

PEG-modified phospholipid and derivatized lipids of the instant invention may comprise a molar ratio from about 0% to about 20%, about 0.5% to about 20%, about 1% to about 15%, about 4% to about 10%, about 2% of the total lipid present in an LNP, or a lesser amount. (Mui et al., Mol Therap-Nucl Acids 2, e139, 2013; and Kumar et al., Mol Therap-Nucl Acids 3: e210, 2014). LNP formulations may contain 0.5% to 3.0%, 1.0% to 3.5%, 1.5% to 4.0%, 2.0% to 4.5%, 2.5% to 5.0%, 3.0% to 6.0% and so on of PEGylated lipid.

As known in the art, PEG is not entirely non-immunogenic. Prevalent use of same in drugs revealed individuals can raise an immune response to PEG (Moghimi, Mol Therap 29 (3) 898-891, 2021). Thus, use of PEG in an LNP and possibility of an immune response thereto must be weighed against beneficial use and properties of PEG in LNP's. Rapid removal of PEG from an LNP (over 50% loss of PEGylated lipid from the LNP's within first hour of administration) might minimize likelihood of rapid clearance of PEG-depleted LNP's from a host. However, as mentioned above, it is believed PEGylated lipid may remain in circulation after leaving an LNP.

Although PEG leaches rapidly from an LNP in vivo, anti-PEG antibodies might jeopardize success of subsequent administrations of PEGylated LNP's.

Opsonization of LNP's may facilitate phagocytosis of LNP's thereby inducing MHC-associated presentation on APC's of LNP components and products, inducing or enhancing an immune response to an expressed polypeptide of interest.

4. Size

In embodiments, particles of the instant invention have an average diameter in the range of from about 50 nm to about 1000 nm, for example, from about 100 nm to about 900 nm, from about 200 nm to about 800 nm, from about 200 to about 700 nm, from about 300 to about 600 nm, from about 300 nm to about 500 nm, from about 300 nm to about 400 nm, from about 70 nm to about 210 nm, from about 80 nm to about 200 nm; and so on.

LNP's generally can be greater than about 10 nm in diameter (size) to avoid rapid clearance by kidneys and smaller than about 200 nm to enable passage through minicapillaries (Selby et al., Rev Nanomed Nanobiotech 9 (5), 2017).

In embodiments, particles of the instant invention have an average diameter of at least about 50 nm, at least about 60 nm, at least about 70 nm, at least about 80 nm, at least about 90 nm, at least about 100 nm, at least about 150 nm, at least about 200 nm, at least about 250 nm, at least about 300 nm, at least about 400 nm, at least about 500 nm, at least about 600 nm, at least about 700 nm, at least about 800 nm, at least about 900 nm, and/or the particles of the instant invention have an average diameter of no more than about 1000 nm, no more than about 900 nm, no more than about 800 nm, no more than about 700 nm, no more than about 600 nm, no more than about 500 nm, no more than about 400 nm, no more than about 300 nm, no more than about 250 nm, no more than about 200 nm, no more than about 150 nm, no more than about 100 nm, no more than about 90 nm, no more than about 80 nm, no more than about 70 nm, no more than about 60 nm.

In embodiments, particles of the instant invention have an average diameter in the range of from about 50 nm to about 400 nm, from about 50 nm to about 200 nm, in the range of from about 200 nm to about 1000 nm, from about 200 nm to about 800 nm, from about 300 nm to about 600 nm, from about 10 nm to about 100 nm, and so on.

Use of particles greater than about 100 nm may enhance rapid removal from a host and enhance uptake by cells. Particles having diameters between about 300 nm and about 600 nm may be useful for targeting antigen presenting cells, such as, dendritic cells or macrophages.

The term, "average diameter," refers to mean diameter of particles and may be calculated by dividing sum of diameters of each particle by total number of particles. Although the term, "diameter," is used normally to refer to length of a line segment passing through the center and connecting two points on periphery of a spherical object, diameter also is used herein to refer to length of a line segment passing through the center and connecting two widest points on periphery of particles having other shapes.

LNP's can be spherical depending on materials and methods used. However, an LNP need not be spherical to be effective, and lipoplexes can assume a variety of different configurations and shapes.

A variety of alternative methods known in the art are available for sizing a population of LNP's. One such sizing method is described in U.S. Pat. No. 4,737,323, incorporated herein by reference in entirety. Size of particles may be determined by quasi-electric light scattering (QELS) as described in Bloomfield, Ann Rev Biophys Bioeng, 10:421-450 (1981), incorporated herein by reference in entirety.

Selection of appropriate size of an LNP can take into consideration site of a target cell or tissue and to some extent, application for which an LNP is made. For example, to target hepatocytes, an LNP may be sized with dimensions smaller than fenestrations of endothelium lining hepatic sinusoids.

5. Ratios

An LNP is prepared by combining multiple lipid and/or polymer components with an mRNA, as known in the art. For example, an LNP may be prepared using a formulation of DSPC/CHOL/DODAP/C8-PEG-5000 ceramide in a relative molar ratio of about 1 to about 50/about 5 to about 65/about 5 to about 90/about 1 to about 25, respectively, such as, about 33/40/25/2, about 31/40/25/4 and so on; for a formulation of POPC/DODAP/C8-PEG-2000-Cer, at a molar ratio of about 75 to about 87/about 3 to about 14/about 10 to about 11; or a formulation of lipids, DSPC/CHOL/DOTAP/C8 PEG-2000-Cer, at a molar ratio of about 31/about 40/about 25/about 4.

Selection of cationic lipids, structural lipids and/or PEG-modified lipid as well as relative molar ratio of such lipids to one another can be governed by characteristics of selected lipid(s), nature of an intended target cell or tissue and characteristics of mRNA's to be delivered. Additional considerations include, for example, saturation of an alkyl chain, as well as size, charge, pH, pKa, fusogenicity, toxicity of selected lipid(s) and so on.

Other features include nature of PEGylation, ratio of all components and biophysical parameters such as, size.

An LNP of Semple et al. (Nature Biotech 2010 28:172-176), was composed of 57.1% cationic lipid, 7.1% dipalmitoylphosphatidylcholine, 34.3% cholesterol and 1.4% PEGylated lipid. Changing composition and amount of cationic lipid could impact delivery of siRNA to various antigen presenting cells (Basha et al. Mol Ther 2011 19:2186-2200).

In embodiments, an LNP may comprise about 35 to about 45% cationic lipid, about 40% to about 50% cationic lipid, about 50% to about 60% cationic lipid, about 55% to about 65% cationic lipid and so on. In embodiments, a ratio of lipid to mRNA may be about 5:1 to about 20:1, about 10:1 to about 25:1, about 15:1 to about 30:1, at least about 30:1 and so on, see, for example, U.S. Pat. No. 10,702,600, at least about 3:1, at least about 5:1, at least about 7:1, at least about 9:1, at least about 11:1, at least about 13:1 and so on.

6. Microfluidics

Methods for nanoparticle packaging or manufacturing are known in the art, for example, see Bose et al., J Virol 78:8146, 2004; Dong et al., Biomat 26:6068, 2005; Lobenberg et al., J Drug Targ 5:171, 1998; Sakuma et al., Int J Pharm 177:161, 1999; Virovic L et al., Exp Opin Drug Deliv 2:707, 2005; and Zimmermann et al., Eur J Pharm Biopharm 52:203, 2001.

Many current methods for making LNP's rely on microfluidic materials and methods, for example, Kimura et al., RSC Adv v. 3, 2021 and Belliveau et al., Mol Therap-Nucl Acids 1: e37, 2012; and the Microfluidics device (Westwood, MA) and the NanoAssemblr device (Precision Nanosystems, San Francisco, CA).

The term, "ethanol injection technique," refers to a process where an ethanol solution comprising lipid is dropped through a needle into an aqueous solution containing mRNA. That disperses lipid throughout the solution and promotes LNP formation. The mixing can be done with agitation.

The term, "reverse phase evaporation technique," refers to a process where an organic solution comprising lipid is introduced into an aqueous solution containing mRNA such that a water/oil (w/o) emulsion is created. Thus, organic solution and aqueous solution should be immiscible. Organic solution then is removed from a water/oil emulsion, for example, by evaporation and so on. That process leads to LNP formation. Resulting solution can be diluted further with an aqueous solution to promote LNP formation.

7. Other

Stabilization of an LNP may be improved with a moiety that inhibits opsonization, which typically are large hydrophilic polymers chemically or physically bound to an LNP, for example, by intercalation of a lipid-soluble anchor into or onto a surface; by binding directly to active groups of a surface lipid; and so on. An opsonization-inhibiting hydrophilic polymer forms a protective surface layer which significantly decreases uptake of LNP's by macrophage-monocyte and reticulo-endothelial systems (for example, as described in U.S. Pat. No. 4,920,016, the entire disclosure of which herein is incorporated by reference in entirety). LNP's modified with opsonization-inhibition moieties thus remain in circulation longer than unmodified counterparts thereof.

Therapeutic Targets

Combination of elements taught herein enables therapeutic use of translatable mRNA's to address disease or abnormal state. (Sahin et al., Nat Rev 13:759-780, 2014). In treatments requiring transient expression of therapeutic polypeptides, translatable mRNA's taught herein now provide a new treatment opportunity and regimen. mRNA therapeutics or pharmaceutics can find use in plural treatment areas.

An area of therapeutic interest is developing an immune response.

The term, "immune response," relates to reaction of an immune system, such as, to an immunogenic organism, such as, a bacterium or a virus; to an immunogenic cell; or to an immunogenic substance. Immune response includes an innate immune response and an adaptive immune response. Immune response is related to activation of immune cells, induction of cytokine biosynthesis, antibody production and so on.

The term, "immunologically active compound," relates to a compound altering an immune response by inducing and/or suppressing maturation of immune cells; inducing and/or suppressing cytokine biosynthesis; altering humoral immunity by stimulating antibody production by B cells; and so on. Immunologically active compounds can possess immunostimulating activity including antiviral and antitumor activity; and can down regulate aspects of an immune response, for example, shifting an immune response away from a Th2 immune response.

The term, "immune cells," refers to cells of an immune system involved in defending a body of an individual from entered assault of a pathogen or from derangement of a normal, healthy state. Immune cells encompass specific types of cells and precursors thereof including leucocytes comprising macrophages, monocytes (precursors of macrophages), granulocytes, such as, neutrophils, eosinophils and basophils, dendritic cells, mast cells and lymphocytes, such as, B cells, T cells and natural killer (NK) cells; and so on. Macrophages, monocytes, neutrophils, dendritic cells and mast cells are phagocytic cells.

Cells most identified with antigen presentation (antigen presenting cells or APC's) for activating T cells are macrophages, dendritic cells and B cells. Those three cells types are known as professional antigen presenting cells. Extracellular antigen is presented on professional cells to CD4 cells as endosome processed peptides associated with MHC class II molecules.

Non-professional antigen presenting cells present intracellular antigen peptides digested in proteasomes in association with MHC I molecules to CD8 cells.

The term, "therapeutic treatment," relates to a regimen that improves health status and/or prolongs (increases) lifespan of an individual. Said treatment may eliminate disease in an individual, arrest or slow development of a disease in an individual, inhibit or slow development of disease in an individual, decrease frequency or severity of symptoms in an individual decrease recurrence in an individual who currently has or who previously had a disease; removes or diminishes a disease symptom; and so on.

The terms, "prophylactic treatment," or, "preventive treatment," relates to any treatment intended to prevent a disease from occurring in an individual. Prophylactic treatment and preventive treatment are used herein interchangeably.

The terms, "protect," "prevent," "prophylactic," "preventive," "protective," and grammatic forms thereof relate to prevention of occurrence and/or propagation of a disease, for example, a tumor, an infectious disease and so on in an individual.

The term, "disease," refers to an abnormal condition that negatively impacts an individual. A disease often is construed as a medical condition associated with specific symptoms and signs. A disease may be caused by factors originally from an external source, such as, infectious disease and so on, or may be caused by internal dysfunction, such as, autoimmune disease, cancer and so on.

The term, "disease involving an antigen," refers to a disease or abnormal state characterized by cells expressing an antigen specific for that disease or abnormal state. A disease involving an antigen can be an infectious disease, an autoimmune disease, a cancer and so on. An antigen may be a disease-associated antigen (synonymous with disease-specific), such as, a tumor-associated antigen, a viral antigen, a bacterial antigen, an antigen of a parasite and so on.

The term, "infectious disease," refers to a disease transmitted from individual to individual or from organism to organism, and is caused by an agent (for example, a bacterium, a virus, a parasite and so on, such as, a rhinovirus or a β coronavirus causing the common cold). Infectious diseases are known in the art and include, for example, a viral disease, a bacterial disease, a parasitic disease and so on. Infectious disease can be a sexually transmitted disease (for example, *chlamydia*, gonorrhea and so on), tuberculosis, HIV/acquired immune deficiency syndrome (AIDS), diphtheria, hepatitis B, hepatitis C, cholera; a disease cause by an alphavirus, a *Streptococcus*, a *Staphylococcus* and so on; an organism that causes pneumonia; a fungal disease or disorder, severe acute respiratory syndrome (SARS), a disease caused by respiratory syncytial virus, cytomegalovirus, influenza and the like; and so on.

Generally, an etiologic pathogen of a disease is target of an immune system response of interest.

The term, "autoimmune disease," refers to a disorder or a disease in which a body produces a response to some constituent of the body. Hence, an immune system loses ability to recognize self from non-self and targets and attacks a self molecule as if foreign or non-self. Autoimmune disease can be classified into those impacting predominantly one organ (for example, hemolytic anemia, anti-immune thyroiditis and so on) and those where an autoimmune disease is diffused through many tissues (for example, systemic lupus erythematosus and so on). For example, multiple sclerosis is thought to be caused by T cells attacking myelin sheaths of nerve fibers in brain and spinal cord. Other examples of autoimmune disease include Grave's disease, rheumatic arthritis, celiac disease, Crohn's disease, colitis, diabetes, scleroderma, psoriasis and so on.

The terms, "cancer disease," or, "cancer," refers to or describes a condition typically characterized by unregulated cell growth in a tissue, organ or by cells. Examples of cancers include a carcinoma, a lymphoma, a blastoma, a sarcoma and a leukemia. Other examples include bone cancer, a blood cancer (such as, a white blood cell cancer and so on; lung cancer, liver cancer, pancreatic cancer, a skin cancer, cancer of the head or neck, cutaneous or intraocular melanoma, colorectal cancer, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, pituitary adenoma and so on.

To be treatable using an immune system, a cancer must express an antigen, such as, a cancer-specific antigen and so on, such as, an antigen specific for a particular cancer.

1. Transmitted Disease

The term, "viral antigen," refers to a viral component comprising an antigen. A viral antigen may be a viral ribonucleoprotein or a structural protein, such as, an envelope protein, for example. Viral antigen is synonymous with virus.

The term, "bacterial antigen," refers to a bacterial component comprising an antigen. A bacterial antigen may be derived, for example, from a cell wall, a cytoplasmic membrane and so on, of a bacterium. Bacterial is synonymous with bacterium.

The term, "antigen of a parasite," refers to a component of a parasite comprising an antigen. An antigen of a parasite may be derived, for example, from a flagellum, a cytoplasmic membrane and so on, of a parasite. Parasitic is synonymous with parasite.

The term, "disease-associated antigen," or, "disease-specific antigen," is used in a broad sense to refer to an antigen associated with a disease. A disease-associated antigen is a molecule which contains epitopes to which a host immune system recognizes and responds, at times, to make a cellular antigen-specific immune response and/or a humoral antibody response. A disease-associated antigen thus can be used for therapeutic purposes. A synonym is disease-specific.

Examples of transmitted diseases that can be treated with an LNP composition of interest include those caused by an alphavirus, such as, Dengue virus, West Nile virus, Zika virus and so on; disease caused by a β coronavirus, such as SARS, MERS, SARS-COV-2 and so on; influenza; disease caused by a *Streptococcus*, a *Staphylococcus* and so on; hepatitis C virus; a disease caused by a respiratory syncytial virus, cytomegalovirus and so on; a microbe causing pneumonia, such as, *Pneumocystis* pneumonia, Hemophilus influenza and so on; a fungal disorder, such as, Candidiasis, Valley Fever, Histoplasmosis and so on; a disease caused by a *Mycobacterium*; a parasitic disease, such as, malaria, and those caused by a Giardia, a *Cryptosporidium*, a *Leishmania*, a *Toxoplasma*, a *Trypanosoma*, a *Schistosoma* and so on; a sexually transmitted disease; and so on.

a. Influenza

A composition can comprise plural LNP's, each comprising a unique mRNA encoding different influenza polypeptides. (For all purposes herein, a first mRNA ORF containing a portion of a second mRNA ORF are considered different mRNA's. Hence, nested mRNA's, that is comprise a series of RNA's with increasing amounts of deleted bases, each is a different mRNA although all mRNA's share a portion of overall sequence, that is, each is contained within another or others that are longer in length.)

Thus, one mRNA encodes an antigenic polypeptide specific for influenza type A and a second mRNA encodes an antigenic polypeptide specific for influenza type B.

An antigenic polypeptide can comprise an influenza hemagglutinin (H) or an antigenic polypeptide can comprise an influenza neuraminidase (N).

In embodiments, the mRNA's encode antigenic polypeptides specific for different subtypes, such as, H1, H2 or H3; or N1 or N2.

b. SARS-COV-2

Studies on SARS-COV revealed that antibodies to spike protein were protective in animals (Bisht et al., PNAS 101 (17) 6641-6646, 2004). A further study revealed that antibodies raised to spike receptor binding domain (RBD) alone generated neutralizing antibody (He et al., Biochem Biopyh Res Comm 324:773-781, 2004). Although spike protein of SARS-COV-2 comprises glycans, the RBD is void of glycans making the RBD freely accessible to a host immune system (Grant et al., Sci Rep 10:14991, 2020).

SARS-COV-2 has about 80% homology to SARS-COV, and the RBD's of the two viruses are similar in structure and function (Wang et al., Med Sci Monit 26: e924700, 2020; and Brouwer et al., Sci 369:643-630, 2020). Based thereon, studies on SARS-COV were used as a basis for developing vaccines for SARS-COV-2.

Because spike protein undergoes conformation change on binding receptor in both viruses, spike protein was manipulated to yield a polypeptide that retained conformation before binding receptor (prefusion) in both viruses. That construct was used to develop a vaccine (Hsieh et al., Sci 369:1501-1505, 2020; Corbett et al., Nat 586:567-571, 2020; Xia, Viruses 13, 109, 2021; Dai & Gao, Nat Rev Imm 21:73-82, 2021; and Zost et al., Nat Med 36:1422-1427, 2020).

A commonly used modification to maintain prefusion configuration of spike protein is substitution of two amino acid sites with Pro residues near juncture of heptad repeat 1 (HR1) and central helix (CH) domains in S2. Thus, on separation of S1 and S2 in that mutant (or modified polypeptide) by receptor binding or enzymic digestion, S2 remains in prefusion configuration.

In embodiments, an mRNA encodes RBD of spike protein.

In embodiments, an mRNA encodes: envelope (E) protein, if not the entire coding sequence, at least the N terminal, extracellular domain; membrane (M) protein, if not the entire coding sequence, at least the N terminal, extracellular domain; or nucleocapsid (N) protein (Bianchi et al., Hindawi, 2020, 4389089, 6 pages).

M is the most abundant virus capsid protein. The N terminus is exposed at the virus surface (Thomas, Path Imm 5:1342-361, 2020; and Mahtarin et al., J Biomol Struct Des DOI: 10.10801.07391102.2020.1861983).

E is the smallest structural protein and can be poorly represented at the virus capsid. However, N terminus of E is extracellular. (Schoeman & Fielding, Virol J 16:69, 2019).

c. Hepatitis A and B

Many current vaccines are subunit vaccines where subunit polypeptides can be produced recombinantly.

Thus, mRNA's encoding those subunit polypeptides can be carried by LNP's of interest.

Hepatitis A (HepA) comprises viral proteins, such as, VP1 (Craff et al., J Virol 73 (7), 1999) and VP4 (Shukla et al., J Virol 88 (21), 2014), and nucleic acids encoding same can be carried by an LNP.

Hepatitis B (HepB) is associated with hepatitis B antigen.

Accordingly, mRNA's encoding a HepA antigenic polypeptide and encoding a HepB antigenic polypeptide can be packaged in separate LNP particles to provide a combination HepA/HepB LNP vaccine.

d. DPT

Many DPT (diphtheria, pertussis and tetanus) vaccines are acellular and employ subunits, which may be made recombinantly. Thus, pertussis antigen is used in some formulations. Other formulations use tetanus and/or diphtheria toxoid, a modified and detoxified form of a toxin.

Accordingly, nucleic acids encoding a toxin are modified to produce a modified toxin, a toxoid, without deleterious activity but remaining immunogenic. For example, such modification may be amino acid substitutions to render a domain impotent, a deletion to remove a domain and so on to yield a toxoid, as known in the art. Then, mRNA's encoding those toxoids are packaged in or with an LNP.

In embodiments, a formulation includes an LNP encoding a pertussis antigenic subunit or polypeptide, one LNP encoding a diphtheria antigenic subunit or polypeptide and a third LNP encoding a tetanus antigenic subunit or polypeptide, or subcombinations or combination thereof.

2. Cancer

The term, "tumor antigen," or, "cancer antigen," refers to a constituent of cancer cells which may be derived from cytoplasm, cell surface or cell nucleus that elicits an immune response. Cancer antigens are produced intracellularly or as surface antigens on tumor cells. Examples of tumor antigens include HER2, EGFR, VEGF, CA-125, MUC1 and so on.

Tumor antigens, as with any antigen, can comprise plural epitopes.

Hence, a first mRNA encoding one or a portion of a tumor antigen and a second mRNA encodes another portion of the tumor antigen; or one mRNA encodes one or more epitopes of a tumor antigen and a second mRNA encodes one or more different epitopes of the tumor antigen, and, in each embodiment, both mRNA's are packaged in separate LNP's.

In embodiments, two populations of LNP's are produced. A first population comprises LNP's comprising an mRNA encoding a cancer-specific antigen, such as, MUC1 and so on. A second population comprises LNP's comprising an mRNA encoding a polypeptide cytotoxin, such as, melittin, a magainin and so on (Xie et al., Open Biol 10 (7), 2020; and Margus et al., J Biomed Sci 24 (21), 2017). The second population of LNP's also carries a targeting coating thereon comprising a binding pair for a cancer antigen, such as, MUC1, said coating comprising, for example, a polypeptide obtained from an antibody comprising an antigen binding domain and that polypeptide binds MUC1.

Therefore, such a formulation elicits an immune response to a tumor antigen (in the example above, the first LNP population) and separately is cytotoxic to tumor cells expressing that tumor antigen (in the example above, the second LNP population). (Such a formulation can be used for any disease expressing a specific antigen, such as, an infectious disease and so on. Hence, a first LNP carries an mRNA encoding an antigen of interest and a second LNP carries an mRNA encoding a cytotoxin, wherein said second LNP comprises a first member of a binding pair as a coating or a targeting agent on a surface of said second LNP, wherein a second member of said binding pair can comprise said antigen.)

3. Allergy

One way to achieve tolerance is to expose a susceptible host to a low dose of allergen (that does not elicit a strong or deleterious immune response), which treatment may comprise repeated exposure to a low dose of allergen over a defined period with a goal of tolerizing a host to that allergen.

Some allergies comprise more than one allergen or an allergen comprises more than one epitope. In embodiments, several allergens or several epitopes are produced using several LNP's, each encoding one allergen or one or a few epitopes.

In embodiments, an allergen comprises plural epitopes. In embodiments, mRNA's encoding the domains or portions of allergen encoding different epitopes are carried by separate LNP's using different mRNA's that encode each domain or each portion comprising a separate epitope.

The amounts of LNP's administered are metered to provide low levels of allergen or epitope expression to simulate a regimen of low dosing to achieve tolerance.

Plural mRNA's

In embodiments, an article of manufacture of interest comprises plural types of LNP's with each type of LNP carrying a different mRNA.

Plural messages are used rather than a single message encoding two or more different polypeptides. Using separate LNP's enables obtaining varying amounts of each polypeptide as compared to equivalent amounts of each polypeptide when ORF's are contained on a single message. Plural messages avoid any need to make a conjugate protein. Plural messages avoid any possible interference of expression of one polypeptide by another, for example, encoding ORF or flanking sequences of one polypeptide may interfere with translation of another downstream encoded polypeptide; an expressed polypeptide may interfere with translation of another downstream ORF; and so on.

Plural messages enable creation of a library of reagents encoding individual polypeptides that can be combined as a design choice.

Plural messages separate antigens or epitopes, which in a naturally occurring state may interact so one antigen or epitopes dominates another so an immune response is biased only to a dominant antigen or epitope.

Mechanisms for domination may not be understood, but may be related to steric or spatial issues, some interaction at antigen presentation and so on.

Irrespective of mechanism, immunodominance is known and often results in a strain-specific, species-specific, line-specific, organism-specific, serotype-specific and so on immune response to a particular pathogen or disease and disease antigen. Such a response, thus, is limited and there is no cross reactivity to other pathogens related to a disease pathogen, such as, a different or related species, a different or related strain, a different or related subtype, a different or related serotype and so on.

For example, for influenza and rhinovirus, an immune response can be restricted to only the infecting strain, subtype, serotype and so on, and the immune response does not react to or with related influenza or rhinovirus of a different strain, subtype, serotype, line and so on. Hence, an immune response to influenza H1N1 subtype, may not provide any protection of a subsequent infection by influenza H2N1; and a response to rhinovirus A may not protect a subsequent infection by rhinovirus B and a response to rhinovirus A1 may not protect a subsequent infection by rhinovirus A15; and so on. That might explain why individuals contract repeated infection year in and year out by a particular pathogen, such as, influenza, rhinovirus and so on.

Hence, separating antigens and epitopes on separate polypeptides enables previous cryptic or silent antigens or epitopes, for whatever reason or mechanism, to be exposed to a host immune system and possibly enabling those cryptic or silent antigens or epitopes to be functionally immunogenic so a host immune system now can generate an immune response to those previous cryptic or silent antigens and epitopes.

A corollary of immunodominance is an immune response that can be specific only to an infecting organism, with no cross reactivity with other subtypes, serotypes, strains, lines and so on. Hence, a non-immunodominant epitope may not generate such a specific immune response, but one which may cross react with other strains, subtypes, serotypes, lines and so on.

Thus, a benefit of such an exercise is those cryptic or silent antigens or epitopes may generate a more robust and cross reactive response that is not strain-specific, subtype-specific, serotype-specific and so on (which may be a function of and a necessary feature of an immunodominant antigen or epitope), thereby providing a means for developing a vaccine with a wider range of effectiveness and offering a broader range of immunoprotection beyond just to a particular strain, subtype, serotype, line and so on.

Plural messages also enable use of smaller mRNA's rather than larger, lengthy molecules that may be susceptible to breakage during synthesis and further manipulation in making a pharmaceutic composition of interest and use thereof.

a. Mutants/Variants

Microbes undergo mutation, which may seem rapid because of short generation time and large populations. Hence, pathogens often yield mutants over time, which may, for example, be more infectious, may be transmitted by a different route, may be less infectious, may be resistant to current treatments and so on.

In embodiments, multiple LNP's are used to carry messages encoding not only a pathogen wildtype polypeptide but also encoding one or more variants thereof.

Variants are identified in a population, are isolated and examined. If a variant exhibits properties which may threaten a population, such as, resistance to existing treatment, more infectious and so on, an mRNA vaccine can be developed to address such a variant.

In embodiments, a vaccine can comprise plural LNP populations, a first carrying an mRNA encoding a wild-type antigenic polypeptide, a second carrying an mRNA encoding a first variant of said wild-type antigenic polypeptide and so on.

Genomic sequencing of a pathogen may reveal sites or domains carrying higher levels of mutation, a, "hot spot." That information may reveal what sites are impacted or are susceptible, what amino acids at those sites are impacted, the sort of amino acid changes observed in a population and so on. Hence, such a site may be in a functional domain, such as, a receptor binding domain, may comprise an epitope of a neutralizing antibody; and so on.

That information enables prediction of possible changes at that site which may arise in a pathogen population. Those changes can be configured into mRNA's encoding those suspected variant polypeptides for packaging in or placed in association with LNP's for use in a vaccine generating a cross reactive response.

Computational methods for analyzing and predicting structure of folded proteins, protein domains and subdomains are available (for example, UCSF Chimera) and for computational protein design and modeling (for example, Rosetta). Those methods may be adapted and used to computationally analyze and predict domains within proteins of a pathogen which are associated with, for example, enhanced pathogenicity, enhanced virulence, enhanced immune escape, enhanced infectivity, enhanced transmissibility, enhanced tropism and so on.

Immunogenic epitopes associated with such n mutations can be predicted using computational methods and algorithms, such as, those developed and commercialized by Epivax Inc. (Providence, RI).

In embodiments, such and other methods known to those skilled in the art are used to design two or more mRNA sequences that encode immunogenic domains or epitopes spanning and employed as vaccines to elicit immune responses.

b. Infectious Disease

In embodiments, a vaccine strategy can benefit from having a host react to different forms of an antigen or a complete, native antigen, or separate parts of an antigen as that may enable a host to generate a more robust polyclonal or cross reactive response to a disease. That strategy enables a host to react to plural epitopes or epitopes in isolation, to generate both cell-mediated and humoral responses and so on.

A first LNP comprises an mRNA encoding a secreted antigen. A second LNP comprises an mRNA encoding that same polypeptide but which is not secreted, and likely maintained intracellularly. Hence a first mRNA comprises a sequence encoding a signal peptide and a second mRNA does not. The two expressed polypeptides are indistinguishable aside from, perhaps a signal peptide and other one or a few amino acids, such as, Lys residues at amino terminus, carboxy terminus or both. Nevertheless, the two polypeptides, secreted or not, have same functions, and for all intents and purposes, are identical.

For example, in embodiments, two LNP's are formulated for spike protein of SARS-COV-2, an LNP carrying an mRNA encoding S1 subunit (the N terminal domain (NTD) and RBD) and other LNP carrying an mRNA encoding S2 subunit in prefusion configuration, which can be obtained, as known in the art, by strategic replacement by two Pro residues.

In embodiments, two LNP's are formulated for Covid spike protein, one mRNA encodes full length spike protein with S2 subunit locked in the prefusion configuration containing a signal peptide for secretion from a transformed cell. The other LNP contains an mRNA encoding that same full length spike protein but containing either or both 5' and 3' poly-Lys domains and not containing a signal peptide.

In embodiments, two LNP's are formulated for Covid spike protein S1 domain, an mRNA encodes S1 containing a signal peptide for secretion from a transformed cell. The other LNP contains an mRNA encoding that same spike protein S1 domain but containing either or both 5' and 3' poly-Lys domains and not containing a signal peptide.

Such a strategy ensures the same polypeptide is expressed as an intracellular protein and as a secreted, extracellular protein, thereby providing a robust antigen presentation to a host. That can balance an immune response between a cellular response and a humoral response, as many vaccines are known to generate little or no cellular response.

For purposes herein, and for an embodiment where two LNP's express two polypeptides, one where a polypeptide is configured for secretion and the other where the same polypeptide is configured for residence in a cell, that is, is not secreted, "same polypeptide," is meant identity between two polypeptides, one expressed as a secreted polypeptide and the other as an intracellular polypeptide. Thus, the ORF's are substantially the same and the expressed polypeptides essentially are the same (and resemble or are identical to the original or founding mRNA and polypeptide), though the secreted polypeptide may have a signal peptide attached thereto and the other non-secreted or intracellular polypeptide may have one or two lysine domains at the amino terminus and/or carboxy terminus. Aside for those two small changes, the two expressed polypeptides have substantially the same primary sequence and functions. Hence, any differences generally are to flanking regions that control different intracellular fate of an expressed polypeptide.

In embodiments, an antigen is dissected to domains or portions carrying epitopes. An antigen is fragmented to yield portions carrying one or more determinants or epitopes. mRNA's encoding those portions are manufactured as taught herein and then are associated with lipids to form LNP's. Those plurality of LNP's are used as a, "deconstructed," antigen and introduced into a host, deconstructing meant to indicate a full length antigen is fragmented to plural polypeptides each carrying one or more epitopes of the original antigen.

Such a strategy might not, "catch," or present conformational epitopes to a host immune system, but exposes a host to epitopes which may not be readily accessible to a host in wildtype form, for example, by steric entanglements, biologic entanglements and so on, that might minimize immunogenicity of a determinant of wildtype antigen. Hence, cryptic or partially silent epitopes now will be exposed fully to a host immune system.

Accordingly, employing a plurality of LNP's enables, in part, expression of a full length antigen to ensure conformational epitopes are exposed to a host immune system as well as expression of fragments, subunits and so on to expose cryptic or silent epitopes.

c. Antigen/Adjuvant

Some antigens benefit from use of an adjuvant to stimulate an immune response or a more vigorous immune response thereto. Adjuvants generally are considered non-specific activators of immune systems. Some adjuvants can be carriers of a determinant or an antigen, others are administered separately but usually coincidently with antigen. Adjuvants can be used to stimulate a cellular response.

Some adjuvants are polypeptides, such as, pertussis toxoid, albumins, cholera toxoid, keyhole limpet hemocyanin and so on.

Other adjuvants include, for example, a heat shock protein, a colony stimulating factor, an interferon and so on.

Other polypeptide adjuvants include ligands of PRR's, such as, cytokines, toxins and so on. Examples include Toll-like receptor (TLR) ligands, such as, flagellin, fibrinogen and so on (Ishii et al., J Clin Imm 27:363-371, 2007; and Kumar et al., Front Imm 10:1144, 2019) and fibrillizing polypeptides, see, for example, Rudra et al., PNAS 107 (2) 622, 2010.

An adjuvant can be a polypeptide comprising CpG (Coffman et al., Imm 33 (4) 492-503, 2010).

Polypeptides (for example, 5-20 residues in length or more) comprised of hydrophobic amino acids (for example, Val, Ile, Leu, Phe and so on), which can be homopolymers or heteropolymers, can be used (Skwarczynski et al., Sci Adv 6: eaax2285, 2020) as adjuvants.

Dendritic cells and macrophages patrol mucosa for foreign bodies. Dendritic cells express C-type lectin receptors, such as, DEC-205 (also known as CD205 or Ly75) which when activated, may induce an immune response; and so on. Hence, activating Ly75 can provide an adjuvant effect. An antibody or a polypeptide with Ly75 binding activity can serve as a means of stimulating Ly75, inducing dendritic cell maturation. Macri et al., Clin Trans Imm 5: e66, 2016.

Hence, included under the umbrella of what is an adjuvant for use herein are polypeptides that are not natural ligands of a receptor known to induce an aspect of an immune response (such as, APC activation and/or maturation, and so on) that nevertheless cause or result in an observable immune response. Examples of adjuvants as used herein include one member of a binding pair, wherein the other member of that binding pair is a molecule known to induce an aspect of an immune response, and the one member of interest produced by an LNP of interest binds to that molecule, such as, an antibody or antigen-binding portion thereof that binds and activates an immune cell activating receptor or molecule, such as, Ly 75 and so on, and the like.

Thus, two populations of LNP's are constructed, one carrying an mRNA encoding an antigen of interest and a second carrying an mRNA encoding an adjuvant.

d. Adjunct Therapy

Often, a treatment yields undesirable or unpleasant side effects. For example, some cancer treatments can yield, for example, immune suppression, anemia and so on.

A primary therapy is one involving a therapeutic polypeptide, such as, an expressed antigen-binding polypeptide, generally derived from an antibody, and can be, for example, an scAb, an scF., a diabody and so on which self assembles an antigen-binding site once expressed. Such a molecule is used for treatment of a disease. Hence, a first LNP population carries an mRNA encoding a polypeptide of a primary therapy.

A second LNP population carries an mRNA encoding a polypeptide for an adjunct therapy directed to treating a disorder or anomalous state arising secondary to a first disease treatment. An example of a secondary treatment would be addressing anemia by expressing an EPO and so on.

In embodiments, two LNP's are designed for a therapeutic use, for example, one LNP can carry an mRNA encoding a therapeutic polypeptide directed to a disease antigen, such as, a cancer antigen and so on; and a second LNP carries an mRNA encoding a polypeptide that is directed to alleviating a side effect from that therapeutic drug, such as, an mRNA encoding a colony stimulating factor (CSF), such as, a granulocyte CSF G-CSF); erythropoietin; a cytokine; and so on.

In embodiments, some disease occurs secondary to a primary disease or disorder. For example, it is not uncommon for a person infected with HIV to present other disorders, such as, pneumocystic pneumonia, candidiasis, tuberculosis, a disease cause by cytomegalovirus, cryptococcal meningitis, toxoplasmosis and so on.

Hence, such circumstances can be treated with a combination of interest, where a first LNP carries a first mRNA encoding a treatment for a primary disease and a second LNP comprises a second mRNA encoding a treatment for a secondary disease. Those LNP's can carry a message encoding an antigen specific to a primary disease and a message encoding an antigen specific to a secondary disease, such as, CMV.

e. Vaccines

As disclosed above, some current vaccines are acellular. Such vaccines using subunits of a pathogen or a toxoid can be replicated using mRNA and LNP's by having the two or more LNP's carry mRNA's encoding different antigenic polypeptides or subunits; or a detoxified toxoid. Different mRNA's can encode polypeptides originating or expressed by a single pathogen or organism, or can encode polypeptides arising from plural pathogens or organisms.

For example, a first LNP carries an mRNA that encodes an antigenic polypeptide of a measles virus and a second LNP carries an mRNA that encodes an antigenic polypeptide of a mumps virus. In embodiments, that combination formulation can include a third LNP which carries an mRNA that encodes an antigenic polypeptide of a rubella virus.

Hence, multiple mRNA's can be used to produce vaccines for, for example, influenza, hepatitis A and hepatitis B, a diphtheria/pertussis/tetanus vaccine (or subcombinations thereof) and so on.

Different mRNA's are manufactured, each encoding a separate antigenic polypeptide or toxoid.

Hence, a composition comprises one LNP comprising an mRNA encoding, for example, a hepatitis A antigenic polypeptide and a second LNP comprising an mRNA encoding a hepatitis B antigenic polypeptide, thereby producing a single vaccine for hepatitis A and hepatitis B.

In embodiments, for SARS-COV-2, a first manufactured mRNA encodes RBD of spike protein.

In embodiments, a first mRNA encodes a SARS-COV-2 M polypeptide. In embodiments, that mRNA encodes at least the N terminal region of M.

In embodiments, a first mRNA encodes a SARS-COV-2 E polypeptide. In embodiments, that mRNA encodes at least the N terminal region of E.

In such exercises, when seeking responses to epitopes which may be cryptic, functionally immunologically silent in presence of an immunodominant epitope, unexposed or only partially exposed in secondary, tertiary and quaternary structures and so on, but may yield an immune response that is broader, is cross-reactive across strains, species, types, lines and so on, it can be beneficial to ascertain whether any such immune response not previously or naturally occurring does not elicit antibody dependent enhancement (ADE), such as, possibly observed with SARS-COV nucleoprotein (N) (Yasui et al., J Imm 181 (9) 6368-6337, 2008).

f. Antivenin

Venom, such as those of reptiles, amphibians, arthropods, such as, insects and crustaceans and so on; other invertebrates, such as, snails and the like; and so on, often are cocktails of toxic proteins, which may be hemolytic, neurotoxic, cytotoxic and so on, and combinations thereof. Some species of snakes, jellyfish, frogs, bees, spiders, snails, fish and the like are known as poisonous because of toxic venom.

In embodiments, a first LNP carries an mRNA encoding a detoxified first venom component, a second LNP carries an mRNA encoding a detoxified second venom component and so on.

Such a composition can be used to tolerize or immunize a person partially or fully to a venom.

While likely used as a prophylactic, an antivenin formulation of interest can be administered to an envenomated individual because expressed polypeptides are detoxified.

Many venoms comprise toxic peptides which can be used for therapeutic benefit, such as, as a cytotoxin for a tumor cell and so on. For example, spider venom, snake venom, scorpion venom, bee venom, jumper ant venom, wolf spider venom and so on are known to contain cytotoxic polypeptides, such as, melittin, a magainin and so on.

Such cytotoxic polypeptide can be used herein for targeted delivery of such a cytotoxic compound to a specific diseased or deranged cell, s provided hereinabove.

Pharmaceutic Uses

Nanoparticle compositions may be formulated in whole or in part as pharmaceutic compositions, whether prophylactic or therapeutic. Pharmaceutic compositions include two or more nanoparticle compositions. For example, a pharmaceutic composition may include two or more nanoparticle compositions including two or more different therapeutic and/or prophylactic mRNA's. Pharmaceutic compositions may include one or more pharmaceutically acceptable excipients or accessory ingredients, such as, those known or described herein. General guidelines for formulation and manufacture of pharmaceutic compositions and agents are available and are known. Conventional excipients and accessory ingredients may be used in a pharmaceutical composition, except insofar as any conventional excipient or accessory ingredient may be incompatible with one or more components and/or functions of a nanoparticle composition.

In embodiments, one or more accessory ingredients may make up greater than about 50% of total mass or volume of a pharmaceutic composition. For example, one or more accessory ingredients may make up 50%, 60%, 70%, 80%, 90% or more of a pharmaceutical composition.

In embodiments, a, "pharmaceutically acceptable," accessory ingredient is at least about 95%, at least 96%, at least 97%, at least 98%, at least 99% or 100% pure. In embodiments, a, "pharmaceutically acceptable accessory ingredient," is approved for use in human and perhaps also for veterinary use. In embodiments, a pharmaceutically accessory ingredient is approved by the United States Food and Drug Administration (FDA).

An, "accessory ingredient," is a compound that can be included in a pharmaceutic composition as an additive for a particular purpose, such as, a buffer, a flavorant, a glidant and so on. An accessory ingredient can be a diluent, an excipient or a carrier.

A pharmaceutic composition of the instant disclosure is formulated to be compatible with an intended route of administration. Examples of routes of administration include subcutaneous, oral (for example, inhalation and so on), intramuscular, subcutaneous, nasal, buccal, vaginal, transmucosal, rectal and so on.

The term, "systemic administration," refers to administration of a therapeutically effective agent for distribution in much of the body of an individual in effective amounts and develops a biological effect. For example, an agent may develop a desired effect by delivery in blood and/or reaches a desired site of action via the vascular system. Typical systemic routes of administration include administration into the vascular system, or oral, pulmonary or intramuscular administration wherein an agent is adsorbed, enters the vascular system and is carried to one or more desired site(s) of action in a body via blood and the circulatory system.

A pharmaceutical composition is generally applied in a, "pharmaceutically effective amount," and, "pharmaceutically," refers to non-toxicity of a material which does not interact with function or action of an active component of a pharmaceutical composition and comprises various additives with generally no adverse impact on or in a recipient. In context of the US and EU, an entity that is pharmaceutically acceptable is one approved for use in drug preparations by the FDA and European Medicines Agency (EMA), respectively.

A pharmaceutically effective amount is one that yields a desired biologic endpoint or effect.

In embodiments, a compositions comprises one or more detergents (for example, Tween 20, Tween 80, Pluronic F68, bile acid salts and so on), protease inhibitors, surfactants (for example, sodium lauryl sulfate and so on), permeation enhancers, solubilizing agents (for example, glycerol, polyethylene glycerol and so on), stabilizers (for example, hydroxypropyl cellulose, hyroxypropylmethyl cellulose and so on), viscosity increasing agents (for example, carbomer, colloidal silicon dioxide, ethyl cellulose, guar gum and so on), sweeteners (for example, aspartame, citric acid and so on), flow aids (for example, colloidal silicon dioxide and so on), plasticizers (for example, diethyl phthalate, triethyl citrate and so on), emulsifiers (for example, carbomer, hydroxypropyl cellulose, sodium lauryl sulfate and so on), polymer coatings (for example, poloxamers, poloxamines and so on), coating and film forming agents (for example, ethyl cellulose, acrylates, polymethacrylates and so on) and so on.

A pharmaceutic composition of interest may contain salts, buffers, preserving agents, carriers, optionally, other therapeutic agents, and so on. A pharmaceutical composition of the instant invention can comprise one or more pharmaceutically acceptable carriers, diluents, excipients and so on.

The term, "excipient," can indicate substances, such as, binders, lubricants, thickeners, surface active agents, preservatives, emulsifiers, buffers, flavoring agents, colorants and so on.

The term, "diluent," relates to a diluting, a thinning agent and so on. Diluent includes any one or more of fluid, liquid or solid, a mixing medium and so on. Examples of suitable diluents include ethanol, glycerol, water and so on.

Other examples of diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar and so on, and/or combinations thereof in solid or liquid form, such as, dissolved or suspended in a fluid, such as, a saline, a buffer, a water and so on. The term, "carrier," relates to one or more compatible solid or liquid fillers or diluents, which are suitable for administration to a human. Carrier relates to a natural or synthetic organic or inorganic component which is combined with an active component to facilitate application or administration of an active component. Carriers can be sterile liquids, such as, a water, an oil, including those which are derived from mineral oil, animals or plants, such as, peanut oil, soy bean oil, sesame oil, sunflower oil and so on; and other natural or synthetic transporting materials. Salt solutions and aqueous dextrose and glycerin solutions also may be used as aqueous carriers. Other examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter and the like, in solid or liquid form, for example, suspended or dissolved in an aqueous, organic or oleaginous fluid.

Pharmaceutically acceptable carriers, excipients or diluents for therapeutic use are known in the pharmaceutic art, and are described in, for example, Remington's Pharmaceutical Sciences.

Antibacterial agents include benzyl alcohol, a paraben, chlorobutanol, phenol, ascorbic acid and the like. Examples of antimicrobial preservatives include benzalkonium chloride, benzethonium chloride, bronopol, cetrimide, cetylpyridinium chloride, chlorhexidine, chlorocresol, chloroxylenol, cresol, ethyl alcohol, glycerin, hexetidine, imidurea, phenoxyethanol, phenylethyl alcohol, phenylmercuric nitrate, propylene glycol and so on. Examples of antifungal preservatives include butyl paraben, methyl paraben, ethyl paraben, propyl paraben, benzoic acid, hydroxybenzoic acid, potassium benzoate, potassium sorbate, sodium benzoate, sodium propionate, sorbic acid and so on. Examples of alcohol preservatives include ethanol, polyethylene glycol, a phenolic compound, bisphenol, hydroxybenzoate, phenylethyl alcohol and so on. Examples of acidic preservatives include vitamin A, vitamin E, β-carotene, citric acid, acetic acid, dehydroascorbic acid, sorbic acid, phytic acid and so on. Other preservatives include tocopherol, tocopherol acetate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite and so on.

Antioxidants, such as, ascorbic acid, sodium bisulfite, sodium metabisulfite, butylated hydroxyanisole and so on, can be included. Examples of antioxidants include α-tocopherol, ascorbyl palmitate, butylated hydroxyanisole, butylated hydroxytoluene, monothioglycerol, potassium metabisulfite, propionic acid, propyl gallate, sodium sulfite and so on.

Granulating and dispersing agents include potato starch, corn starch, tapioca starch, sodium starch glycolate, a clay, alginic acid, guar gum, citrus pulp, agar, bentonite, cellulose, a wood product, natural sponge, a cation exchange resin, calcium carbonate, a silicate, sodium carbonate, polyvinyl pyrrolidone (PVP) (which may be crosslinked,) sodium carboxymethyl starch, carboxymethyl cellulose, methylcellulose, microcrystalline starch, water insoluble starch, calcium carboxymethyl cellulose, magnesium aluminum silicate, sodium lauryl sulfate, quaternary ammonium compounds and so on, and combinations thereof.

Examples of suitable binders include starch, gelatin, a natural sugar, such as, glucose and so on; anhydrous lactose, β-lactose, a corn sweetener, a natural gum, a synthetic gum, such as, acacia, tragacanth, sodium alginate and so on; carboxymethyl cellulose, polyethylene glycol, gelatin, carbomer, ethyl cellulose, guar gum, hydroxypropyl cellulose, hydroxypropyl methyl cellulose, PVP and so on.

Disintegrants include cornstarch, potato starch, alginic acid, silicon dioxide, guar gum and so on.

Surface active agents and/or emulsifiers include a natural emulsifier (for example, acacia, agar, alginic acid, sodium alginate, xanthan, pectin, gelatin, egg yolk, casein, wool fat, cholesterol, wax, lecithin and so on), a colloidal clay (for example, bentonite [aluminum silicate], magnesium aluminum silicate and so on), a long chain amino acid derivative, a sorbitan fatty acid ester, a sucrose fatty acid ester, a polyethylene glycol fatty acid ester, a polyoxyethylene ether, PVP, diethylene glycol monolaurate, triethanolamine oleate, sodium oleate, potassium oleate, ethyl oleate, oleic acid, ethyl laurate, sodium lauryl sulfate, cetrimonium bromide, cetylpyridinium chloride, benzalkonium chloride, docusate sodium and so on, and combinations thereof.

Examples of suitable lubricants include sodium oleate, sodium stearate, magnesium stearate, calcium stearate, stearic acid, silica, talc, malt, glyceryl behenate, a hydrogenated vegetable oil, polyethylene glycol (PEG) and so on, and combinations thereof.

Examples of chelating agents include ethylenediaminetetraacetic acid (EDTA), citric acid monohydrate, disodium edetate, dipotassium edetate, edetic acid, fumaric acid, malic acid, phosphoric acid, tartaric acid and so on.

Buffers include acetates, citrates, phosphates; an aminoethane buffer, a Good buffer, ammonium chloride, calcium carbonate, calcium chloride, calcium citrate, calcium gluconate, gluconic acid, calcium glycerophosphate, calcium lactate, calcium lactobionate, propanoic acid, dibasic calcium phosphate, phosphoric acid, tribasic calcium phosphate, calcium hydroxide phosphate, potassium acetate, potassium chloride, potassium gluconate, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, an aminosulfonate buffer, magnesium hydroxide, aluminum hydroxide, alginic acid, pyrogen-free water, isotonic saline, Ringer's solution, ethyl alcohol and so on, and combinations thereof, including solutions of any of the above.

Isotonicfiers and agents for adjustment of tonicity, such as, sodium chloride; dextrose; a sugar; a polyalcohol, such as, mannitol, sorbitol and so on; and the like, can be included in the composition.

pH can be adjusted with an acid or a base, such as, HCl, NaOH and so on.

Controlled or delayed release can be brought about by including in a composition, an agent that delays absorption, for example, a coating of aluminum monostearate, a gelatin and so on.

In embodiments, an LNP is prepared with carriers that protect a compound against rapid elimination from a body, such as, implants, depots and so on. Biodegradable, biocompatible polymers can be used, such as, ethylene vinyl acetate, a polyanhydride, polyglycolic acid, collagen, a polyorthoester, polylactic acid and so on.

Liquid dosage forms for oral and parenteral administration include pharmaceutically acceptable emulsions, solutions, suspensions, syrups, elixirs and so on. In addition to active ingredients, liquid dosage forms may comprise inert diluents commonly used in the art, such as, water, other solvents and so on; solubilizing agents and emulsifiers, such as, ethyl alcohol, isopropyl alcohol, ethyl carbonate, ethyl acetate, benzyl alcohol, benzyl benzoate, propylene glycol, 1,3-butylene glycol, dimethylformamide, oils (such as, cottonseed, groundnut, corn, germ, olive, castor oil, sesame oil and so on), glycerol, tetrahydrofurfuryl alcohol, a polyethylene glycol, a fatty acid ester of sorbitan and so on; and mixtures thereof.

Oral compositions can include additional agents, such as, wetting agents, emulsifying and suspending agents, sweeteners, flavorants, odorants and so on. In embodiments for parenteral administration, compositions can be mixed with solubilizing agents, alcohols, oils, modified oils, glycols, polysorbates, cyclodextrins, polymers and so on; and combinations thereof.

The term, "parenteral administration," refers to administration of a therapeutically effective agent such that an agent does not pass the intestine. Parenteral administration includes intravenous administration, subcutaneous administration, intradermal administration and so on.

Solutions or suspensions used for parenteral, such as, intramuscular application, can include a sterile diluent, such as, water for injection, a saline, an oil, a polyethylene glycol, ethanol, glycerine, a polyol, such as, propylene glycol and so on; other solvent and so on. A parenteral preparation can be enclosed in ampoules, disposable syringes or multiple dose vials made of glass or plastic as an article of manufacture.

A composition generally is sterile and is fluid to the extent that syringability or delivery success exists. Proper fluidity can be maintained, for example, by use of a coating, such as, a lecithin and so on; by maintenance of required particle size in the case of a dispersion, use of a thickener and so on; by use of surfactants and so on.

Sterile injectable solutions can be prepared by incorporating LNP's in a required amount of an appropriate solvent with one or a combination of accessory ingredients enumerated herein, as required, followed by filter sterilization. Generally, dispersions are prepared by incorporating LNP's in a sterile vehicle that contains a basic dispersion medium and required other ingredients, as known in the art.

In the case of a sterile powder for preparation of a sterile injectable solution, a solution of LNP's can he treated by, for example, lyophilization, vacuum drying, freeze drying and so on, to yield a dry powder of finely divided LNP's plus any additional accessory ingredients from the previously sterile-filtered solution. A preparation of interest can be stored and reconstituted with a suitable liquid for use.

An injectable formulation can be sterilized, for example, by filtration through a filter and/or by incorporating sterilizing agents in the form of sterile solid compositions which are dissolved or dispersed in sterile water or other sterile injectable medium prior to use.

Oral compositions generally include an inert diluent, flavorant, odorant, an edible carrier and so on. A composition can be enclosed in gelatin capsules or compressed into tablets or troches.

Tablets, pills, troches and the like can contain a binder, such as, microcrystalline cellulose, gum tragacanth, gelatin and so on; an excipient, such as, starch, lactose and so on; a disintegrating agent, such as, alginic acid, corn starch and so on; a lubricant, such as, magnesium stearate and so on; a glidant, such as, colloidal silicon dioxide and so on; a sweetening agent, such as, sucrose, saccharin and so on; a flavoring agent, such as, peppermint, methyl salicylate, a flavoring; and so on.

Oral compositions also can be prepared using a fluid carrier to yield a syrup or liquid formulation for injection, or for use as a mouthwash, wherein a solution comprising LNP's in a fluid carrier is applied orally, swished and expectorated or swallowed.

A pharmaceutical composition may be suitable for buccal administration. Such formulations may, for example, be in the form of tablets and/or lozenges made using conventional methods, and may include, for example, 0.1% to 20% (wt/wt) active ingredient and so on, the balance comprising an orally dissolvable and/or degradable composition and, optionally, one or more of the accessory ingredients described herein. Alternatively, formulations suitable for buccal administration may comprise a powder and/or an aerosolized and/or atomized solution and/or suspension comprising active ingredient. Such formulations, when dispersed, may have an average particle and/or droplet size in the range from about 0.1 nm to about 200 nm, and may further comprise one or more of any accessory ingredients described herein.

A buccal preparation can include a flavorant, an odorant and so on.

For administration by inhalation, a compound is delivered in the form of, for example, a wet or dry aerosol spray, for example, from a pressurized container or dispenser that can contain a suitable propellant, for example, a gas, such as, carbon dioxide and so on; a nebulizer; a mister; and so on.

In general, inhalation is meant to encompass delivery of a substance to blood via a respiratory system, such as, lungs and so on; wherein delivery takes place across a respiratory tract, such as, pulmonary epithelium and so on. Inhalation can be via mouth, nose or intratracheal. Absorption can occur in any part of a respiratory system, including, mouth, throat and so on.

Delivery by inhalation can be by, for example, an inhaler, a nebulizer and so on, see, for example, U.S. Pat. No. 6,595,202, the content of which is incorporated by reference herein in entirety.

A variety of aerosolization systems have been proposed to disperse pharmaceutical formulations. For example, U.S. Pat. Nos. 5,785,049 and 5,740,794 (the disclosure of each of which herein is incorporated by reference in entirety) describe exemplary powder dispersion devices that utilize a compressed gas to aerosolize a powder.

Other types of aerosolization systems include those which typically have a drug that is stored in a propellant, nebulizers which aerosolize liquids using a compressed gas and the like.

Pharmaceutical compositions formulated for pulmonary delivery may provide an active ingredient in the form of droplets of a solution and/or a suspension. Such formulations may be an aqueous and/or a dilute alcoholic solution and/or a suspension, optionally sterile, comprising an LNP composition, and may be administered using any nebulization and/or atomization device. Such formulations may comprise one or more accessory ingredients including a flavoring agent, such as, saccharin sodium and so on; a volatile oil, a buffering agent, a surface active agent; a preservative, such as, methylhydroxybenzoate and so on; and the like. Droplets provided by that route of administration may have an average diameter in the range from about 1 nm to about 200 nm.

A liquid inhaler may deliver about 50 µl/puff (at 20 mg/ml). Generally, about 65% of an inhaled composition arrives at lungs, which can be about 650 µg. A dry inhaler may deliver up to 25-30 mg/puff. Generally, about 50% of an inhaled composition gets to lungs, which can be about 15 mg.

Formulations described herein as useful for pulmonary delivery also may be used for intranasal delivery.

A formulation for intranasal administration may be a coarse powder comprising active ingredients and having an average particle size of from about 0.2 µm to about 500 µm. Such a formulation is administered in a manner in which snuff is taken, that is, by rapid inhalation through a nasal passage from a container of powder held close to a nostril.

Formulations suitable for nasal administration, including a nasal spray and so on, may, for example, comprise from about as little as about 0.1% (wt/wt) to as much as about 100% (wt/wt) of active ingredient and so on, and may comprise one or more of additional ingredients described herein. A fine mist is generated by a handheld device and a user inhales by nose as a spray is generated.

A pharmaceutic composition may be prepared for ophthalmic administration. Such a formulation may, for example, be in a form of eye drops including, for example, an about 0.1/1.0% (wt/wt) solution and/or suspension of active ingredient and so on in an aqueous or oily liquid excipient. Such drops may comprise buffering agents, salts, one or more other accessory ingredients and so on, as described herein or as known in the art. Other ophthalmically-administrable formulations which are useful include those which comprise active ingredient in microcrystalline form and/or in an ointment.

For mucosal exposure in a digestive or reproductive tract, for example, LNP's of interest can be delivered as suppositories, a foam, a fluid, such as, an enema and so on; and the like.

A liquid can be prepared as described herein for other liquid formulations. A liquid can be applied rectally using a reservoir, and a liquid carrying LNP's of interest can be retained or discharged after a certain period.

A foam may be used for delivery. A foam can contain water and/or an oleaginous base, a polymer, a surfactant, a gelling agent or a foam stabilizing agent and so on, along with, when used with a canister for foam production, a liquid or compressed gas propellant, see, for example, U.S. Pat. Nos. 6,818,204 and 9,539,208. LNP's are mixed with liquid ingredients, mixed with propellant and encased in a pressurized container. Alternatively, a foam may be produced by a manually operated device, such as one finger actuated, without need for a propellant.

A therapeutic foam is generated for application to an appropriate mucosal site, such as, rectum, vagina and so on.

LNP's also can be prepared as suppositories (for example, with conventional suppository bases, such as, cocoa butter, glycerides and so on). Compositions for rectal or vaginal administration typically are suppositories which can be prepared by mixing compositions with suitable non-irritating excipients, such as, polyethylene glycol, a suppository wax and so on which are solid at ambient temperature but liquid at body temperature and therefore melt in rectum or vagina and release active ingredient therein. Suppositories can be administered manually or with a dedicated device, see, for example, U.S. Pat. No. 10,653,623.

In embodiments, a formulation comprises a pharmaceutically acceptable oleaginous base or substance. An oleaginous base can be naturally occurring, semi-synthetic or synthetic. In embodiments, an oleaginous base includes glycerides (for example, monoglycerides, diglycerides, triglycerides and so on); and so on. For example, an oleaginous base can include a mixture of monoglycerides, diglycerides triglycerides and so on, in a variety of ratios. In embodiments, an oleaginous base includes triglycerides (for example, more than about 50% of glyceride content can be triglycerides and so on).

Other suitable oleaginous bases include, for example, *theobroma* oil/cocoa butter, triglycerides from vegetable oils, hydrogenated coco-glycerides, trilaurin triglycerides (for example, glyceryl tridodecanoate, glycerin trilaurate and so on), lecithin and hydrogenated lecithin, synthetic or semi-synthetic triglycerides and so on; and mixtures thereof. In embodiments, a formulation includes triglycerides from a hydrogenated vegetable oil. The vegetable oil can be, for example, a palm oil, a palm kernel oil, a cottonseed oil, a soybean oil, a rapeseed oil, a coconut oil, a peanut oil, a sunflower seed oil, an olive oil and so on. In embodiments, an oleaginous base is a semi-synthetic glyceride base comprising saturated $C_8$-$C_{18}$ triglyceride fatty acids, lecithin and so on.

In embodiments, LNP's of interest can be coated with a hydrophilic and degradable layer or shell. Such a configuration confers stability to LNP's when carried and stored in oleaginous carriers and diluents, such as those used in suppositories. On melting, LNP's of interest are exposed to an in vivo aqueous environment where that hydrophilic layer or shell dissolves exposing an LNP of interest to tissues and cells of mucosa.

In embodiments, a formulation comprises a water soluble, water miscible base. Examples of water-soluble miscible bases include glycerinated gelatins, polyethylene glycol (PEG) polymers (for example, PEG 300, PEG 1450, PEG 3350, PEG 6000, PEG 8000 and the like); and so on.

In embodiments, a formulation further comprises an accessory ingredient including adsorbents, surface acting agents (for example, mucosal adhesives, such as, xanthan gum, lisinopril, hydroxypropyl methylcellulose, carboxy methylcellulose, chitosan among others; and so on), viscosity-influencing agents, suspending/dispersing agents, plasticizers (for example, diethylhexyl phthalate and so on), melting point-adjusting agents (for example, white wax and so on), antimicrobial agents, antioxidants and so on.

Suppository formulations are solid or semi-solid. In embodiments, a formulation has a melting temperature in a range of about 35° C. to about 41° C., of about 37° C. to about 39° C.; and so on.

Other polymers, such as, gelatin and so on, may be incorporated to make a suppository more rigid to enable insertion digitally or with an applicator without breaking or fracturing.

In embodiments, a suppository can have a weight of about 2 grams (g), although weight can range from about 500 mg to about 5 g.

In embodiments, a suppository can have an oblong shape. In embodiments, an oblong shape further comprises a cylindrical shape. In embodiments, a suppository has a shape that allows contact between an outer surface of a suppository and rectal mucosal membrane when a suppository is situated in a rectum.

Such a formulation can be used as a vaginal suppository.

Alternatively, a rectal delivery vehicle or a vaginal delivery vehicle can be a foam, can be a lyophilized foam, see, for example, U.S. Pat. No. 5,863,553.

Thus, an aqueous dispersion is made comprising at least one or several, water-soluble polymers, and LNP's of interest. The term, "aqueous dispersion," is meant to include dispersions (including solutions) in which a solvent is water or a water miscible liquid.

Cellulose, cellulose ethers, derivatives thereof, polymers of the type disclosed in U.S. Pat. No. 4,615,697 and so on can be used. Other suitable polymers include polycarboxylated vinyl polymers, polyacrylic acid polymers, polysaccharide gums (such as, natural plant exudates including karaya gum, ghatti gum and the like), seed gums (including, for example, guar gum, locust bean gum, psigllium seed gum and the like); and so on can be used.

Other suitable polymers include polyurethanes, gelatins, celluloses and cellulose ethers, including hydroxypropylmethylcellulose, sodium carboxymethylcellulose, methylcellulose, hydroxyethylcellulose, hydroxypropylcellulose, hydroxyethylmethylcellulose, hydroxyethylethylcellulose, hydroxypropylethylcellulose and so on; carbopol, polyvinyl alcohol and derivatives thereof, dextran, chitosan and derivatives thereof, starch and derivatives thereof, polyacrylamides, polyacrylates, agar, collagen, fibronectin, alginic acid, pectin, hyaluronic acid and so on, or mixtures thereof.

Cellulose ethers and hydroxypropylmethylcellulose can provide liquid foams that are stable with structural integrity, and dry foams with desirable softness.

Polymer is added to a dispersion at a concentration of about 1% to about 20% (by weight of total dispersion). At lower concentrations, there may be insufficient polymer to prepare a sturdy foam, whereas at higher concentrations, a dispersion may be too viscous to foam under normal conditions.

To ensure an aqueous dispersion will foam, viscosity of a dispersion can be maintained at about 4500 to 7000 cps, as measured on a Brookfield viscometer at 32° C. using a number 4 spindle at 20 rpm. It may be necessary to cool a dispersion to about 32 to 35° C. by mixing to maintain desired viscosity.

After all materials are blended into an aqueous dispersion having adequate viscosity for foaming, that dispersion then is transferred to a continuous, enclosed mixer known as an, "Oakes," foamer used to manufacture, for example, creamy, smooth food products, such as, ice cream and marshmallows, see, for example, U.S. Pat. Nos. 2,572,049, 2,600,569, 2,679,866, and 3,081,069.

An Oakes foamer is comprised of an electrical system, an air system and a product section. Generally, a device comprises a pump; a mixing chamber; a head assembly having a rotor; a gas inlet; an outlet for a foamed dispersion; means to measure pump speed, rotor speed, flow rate and pressure of an incoming gas; and means to measure back pressure of a foamed dispersion.

A product section consists of a positive displacement pump; speed reducer; inlet piping; a back pressure gauge to monitor back pressure; and a mixing chamber. A gauge is isolated from product by a diaphragm seal assembly.

A liquid dispersion is fed to a pump, transmitted through a line to a mixing chamber wherein a liquid is combined with air, under pressure, and mixed by a head assembly with a rotor. In a mixing chamber, a dispersion is foamed, and air and dispersion are blended into a substantially uniform, homogeneous mixture. From a mixing chamber, a foamed dispersion then is sent to an outlet pipe.

Increasing pressure and/or air flow rate into a fixed volume of dispersion can produce a more flexible, faster dissolving suppository. Changing pump speed or rotor speed also changes liquid density of a foamed liquid dispersion.

Foams of varying liquid density can be produced by varying flow rate of incoming gas.

Density of a liquid foamed dispersion can range from about 0.1 to about 1.0 gm/cc.

A foamed dispersion can be lyophilized to yield a foamed suppository of interest carrying LNP's of interest.

Suppositories can have a (dry) density of about 0.001 to about 0.1 gm/cc, as such suppositories have good dissolution time while being sturdy, yet soft and flexible. That provides a suppository that is comfortable to a user and yet does not readily break or fracture on insertion.

To obtain shaped dry foams, a foamed liquid dispersion is placed into a receptacle having a known volume ("unit dosage"). Since liquid density of a foam and volume of a receptacle are known, foam weight of each unit dosage can be determined. Liquid can be extruded through a tubing into a mold. Various aluminum, plastic and release liner covered molds can be employed.

Foam is extruded into compartmentalized trays whereby volume of one compartmental unit equals volume of a resulting suppository. The mold may be constructed in size and shape of a suppository.

LNP's can be used in topical form, such as, gels, creams, ointments, lotions, unguents, other cosmetics and the like. LNP's can be carried in a formulation comprising emollients, bleaching agents, antiperspirants, moisturizers, scents, colorants, pigments, dyes, antioxidants, oils, fatty acids, lipids, inorganic salts, organic molecules, opacifiers, vitamins, pharmaceuticals, keratolytic agents, UV blocking agents, tanning accelerators, depigmenting agents, deodorants, perfumes, insect repellants and the like.

Other formulations include liquid and/or semi liquid preparations, such as, liniments, lotions, oil in water emulsions, water in oil emulsions, such as, pastes and like; and so on. Topically-administrable formulations may, for example, comprise from about 1% to about 10% (wt/wt) LNP's, although concentration of active ingredient may be as high as solubility limit of LNP's in a solvent.

Another method of administration comprises addition of a compound of interest into or with a food or drink, such as, a food supplement, an additive and so on. LNP's can be encapsulated into forms that survive passage through a gastric environment. Such forms are commonly known, for example, as enteric formulations.

An immune system can be divided into two functionally independent compartments: the systemic compartment represented by bone marrow, spleen, blood and lymph nodes; and the mucosal compartment represented by lymphoid tissue in mucosae and external secretory glands. A consequence of such compartmentalization is systemic routes of drug delivery can be of limited value for prevention of disease arising from interaction with mucosa. Level of protection against diseases of respiratory, genital or intestinal tract correlates better with levels of antibodies in local external secretions than in serum.

In general, drug administration strategies focus on ease of delivery or stimulation of systemic humoral and/or cellular immune responses to specific antigens. But a majority of infectious disease is acquired via mucosal surfaces. Systemic treatment strategies typically do not elicit mucosal immune responses. For instance, a common route for acquisition of HIV involves passage of virus across a mucosal surface. Disruption of mucosa allows virus to reach underlying lamina propria lymphoid cells. Secretory immunoglobulin A (IgA) may function as a first line of defense against such infections, preventing attachment and transmission of virus through mucosa. In addition, IgA could inhibit viral replication within infected epithelial cells.

A mucosal immune system requires mechanisms for selective switching between expansion of effector cells and induction of tolerance. Inappropriate induction of mucosal immune responses can result in clinical syndromes, including food and respiratory allergies (Holt & McMenamin, Clin Exp All 19 (3): 255-62, 1989; Brandtzaeg et al. (1993) "Immunophysiology of the Gut," Bristol-Meyers Squibb/Mead Johnson Nutrition Symposia, Walker et al., eds., London., Academic Press, pp. 295-333); Brandtzaeg et al., Gastroent 97 (6): 1562-84, 1989) and Kalb et al., Am J Respir Cell Mol Biol 4 (4): 320-9, 1991). Selection of mucosal tissue for drug delivery may result in differences in an immune response.

Mucosal immunity typically involves both cellular as well as antibody responses. Production of secreted IgA is a widely accepted surrogate marker for a mucosal immune response.

Intranasal and intratracheal immunization of viral vectors carrying SARS components generated a systemic immune response.

Bukreyev et al. (Lancet 363:2122-2127, 2004) used an attenuated parainfluenza virus introduced intranasally and intratracheally to African green monkeys to express SARS-COV spike protein. Animals challenged with SARS did not shed virus a day after challenge and expressed serum antibody for up to 28 days post challenge.

Hassan et al. (Cell 183:169-184, 2020) exposed mice intranasally to a chimpanzee adenoviral vector carrying stabilized SARS-COV-2 spike protein. Specific IgG and IgA antibodies were elicited. Mice exposed to vector were protected in lung and respiratory tract from subsequent virus challenge.

Kozlowski et al. (Inf Imm 65 (4) 1387-1394, 1997) found rectal and vaginal immunization with inactivate *V. cholera* generated serum IgG ad saliva IgA. Rectal vaccination also generated a moderate antibody response in vaginal secretions.

Jertborn et al. (Inf Imm 69 (6) 4125-4128, 2001) observed essentially similar results, rectal immunization with inactive *V. cholera* carrying recombinantly produced B subunit of cholera toxin yielded serum α-toxin antibody.

Rotavirus (RT) virus-like particles administered rectally along with an adjuvant to mice generated α-RT IgA in serum and in feces; and α-RT IgG in serum. Immunized mice were protected from RV challenge (Parez et al. J Virol 80 (4) 1752, 2006).

Mice rectally immunized with just a single dose of *E. coli* ghosts were protected fully from a 50% lethal challenge with an enterohemorrhagic *E. coli* strain. (Mice exposed to *E. coli* ghosts administered orally, intraocularly or intranasally required two doses to achieve comparable protection.) (Mayr et al., Microb Biotech 5 (2) 283-294, 2012).

*V. cholerae* ghosts carrying porin protein and N terminal portion of polymorphic membrane protein D of *Chlamydia trachomatis* were administered rectally to mice. *Chlamydia*-specific CD4 cells and specific serum antibody were observed. Following intravaginal challenge of live *C. trachomatis*, vaccinated mice had less virus shedding and fewer anatomic complications observed in *chlamydia* infection (Pais et al., PLOS ONE 12 (6) e0178537, 2017).

Mucosal inductor sites adjacent to or containing, "mucosal-associated lymphoid tissue," (MALT) in mucosal tissue can elicit immune responses, including secretion of IgA. Such mucosal inductor sites are found, for example, in tonsils and nasal lymphoid tissue, (Waldeyer's ring of oropharyngeal lymphoid tissue in nasal, palatinal and lingual tonsils), in bronchus-associated lymphoid tissue (BALT), gut-associated lymphoid tissue (GALT, for example, Peyer's patches and the like) and so on. Effector sites from which IgA is secreted may be located in anatomically remote glands, such as, lacrimal, salivary and mammary glands, as well as in nasal mucosa, upper respiratory tract, small intestine, large intestine, genital tract and so on.

"Mucosa," refers to mucosal tissue of a host including respiratory passages (including bronchial passages, lung epithelium, nasal epithelium and so on), genital passages (including vaginal mucosa, penile mucosa, anal mucosa and so on), urinary passages (for example, urethra, bladder and so on), mouth, eyes, vocal cords and so on. Those tissues can be points of entry of LNP's of interest to obtain a mucosal response.

"Point of Entry," refers to site of introduction of an LNP into a host, including immediately adjacent tissue.

"Mucosal Inductor Site," refers to a site on or in mucosa where uptake of an LNP is desired, including, but not limited to, Waldeyer's ring, Peyer's patches, GALT, BALT, nasal-associated lymphoid tissues, genital-associated lymphoid tissues, tonsils and so on. At such a site, an LNP is placed in proximity to lymphoid tissue.

Mucosal administration can be accomplished, for example, through use of nasal sprays, eye drops, nebulizers, inhalers, atomizers, suppositories and so on. Administration can be to nose, trachea, lung and so on.

In embodiments, a mucolytic agent can be administered together with an LNP composition of interest or at about the same time an LNP composition is administered to thin a mucus. For example, a mucolytic can be administered before an LNP composition is administered. Examples of a mucolytic includes acetyl cysteine, ammonium chloride, ammonium carbonate, DNase I and so on. An mRNA encoding a DNase I can be included in an LNP population of interest, see section in adjunct therapy, supra.

The term, "pharmaceutically effective amount," refers to an amount which achieves a desired reaction or a desired effect in vivo alone or with further doses. In the case of treatment of a particular disease, a desired reaction relates to inhibition of a symptom or course of a disease. That can comprise slowing down progress of disease and/or interrupting or reversing progress of disease. A desired reaction in treatment of disease also may be delay of onset or prevention of onset of said disease or said condition.

An effective amount of LNP's described herein will depend on condition to be treated, severity of disease, individual parameters of a patient, including age, physiologic condition, size and weight; duration of treatment, type of an accompanying therapy (if present), specific route of administration and similar factors. Efficacy can manifest at different levels. For example, one level can be degree, percentage or number of cells containing an LNP or an mRNA of interest; amount of expressed polypeptide in vivo; degree of host reaction to an expressed polypeptide, for example, serum antibody thereto and so on; reduction of a symptom, improvement of a disease, condition of a host, prevention of disease and so on.

Effective expression of polypeptides of interest depends on a number of factors, including LNP survival in vivo after administration, LNP entry into cell, LNP escape from an endosome, translation of message and desired fate of a produced polypeptide. Success may be low, for example, it was estimated only about 1% of LNP's escape from endosomes (Gilleron et al., Nat Biotech, doi: 10.1038/nbt.2612), which may be sufficient as vigorous immune responses have been obtained, such as, for the two SARS-COV-2 vaccines currently in use.

In the case that a reaction in a patient is insufficient with an initial dose, follow on doses, higher doses (or effectively higher doses achieved by a different, more localized route of administration), repeated doses and so on may be used.

It can be advantageous to formulate oral or parenteral compositions in dosage unit form for ease of administration and uniformity of dosage. "Dosage unit form," as used herein refers to physically discrete units suited as unitary dosages for a subject to be treated; each unit containing a predetermined quantity of active compound calculated to produce a desired therapeutic endpoint.

Dosages, for example, preferred routes of administration and amounts are obtainable based on empirical data obtained from preclinical and clinical studies, practicing methods known in the art. Dosage and delivery form can be dictated by and can be dependent on characteristics of LNP's, polymers, particular therapeutic effect to be achieved, characteristics and condition of a recipient and so on. For repeated administration over several days or longer, depending on condition, treatment can be sustained until a desired endpoint is attained.

Relative amounts of the two or more nanoparticle compositions, one or more pharmaceutically acceptable accessory ingredients, and/or any additional ingredients in a pharmaceutical composition in accordance with the instant disclosure will vary, depending on identity, size, and/or condition of a subject treated and further depending on route by which a composition is administered. By way of example, a pharmaceutical composition may comprise between about 0.1% and about 100% (wt/wt) of two or more nanoparticle compositions, each LNP in a defined relative ratio, such as, 1:1 and so on.

In embodiments, compositions of interest are administered at dosage levels sufficient to deliver from about 0.0001 mg/kg to about 10 mg/kg from about 0.0001 mg/kg to about 5 mg/kg, from about 0.0001 mg/kg to about 2.5 mg/kg, from about 0.0001 mg/kg to about 1 mg/kg, from about 0.0001 mg/kg to about 0.25 mg/kg or greater amount of a therapeutic and/or prophylactic mRNA in a given dose of each LNP. A dose may be administered one or more times per day, in same or a different amount, to obtain a desired level of mRNA expression and/or therapeutic or prophylactic effect.

In embodiments, a unit dose or a single dose of a composition of interest can comprise, for each LNP, from about 1 μg to about 500 μg of each LNP, from about 1 μg to about 400 μg of each LNP, from about 1 μg to about 300 μg of each LNP, from about 1 μg to about 200 μg of each LNP, from about 1 μg to about 100 μg of each LNP, from about 3 μg to about 500 μg of each LNP, from about 3 μg to about 400 μg of each LNP, from about 3 μg to about 300 μg of each LNP, from about 3 μg to about 200 μg of each LNP, from about 3 μg to about 100 μg of each LNP, from about 5 μg to about 500 μg of each LNP, from about 5 μg to about 400 μg of each LNP, from about 5 μg to about 300 μg of each LNP, from about 5 μg to about 200 μg of each LNP, from about 5 μg to about 100 μg of each LNP, from about 7 μg to about 500 μg of each LNP, from about 7 μg to about 400 μg of each LNP, from about 7 μg to about 300 μg of each LNP, from about 7 μg to about 200 μg of each LNP, from about 7 μg to about 100 μg of each LNP, from about 10 μg to about 500 μg of each LNP, from about 10 μg to about 400 μg of each LNP, from about 10 μg to about 300 μg of each LNP, from about 10 μg to about 200 μg of each LNP, from about 10 μg to about 100 μg of each LNP, or in an amount outside of those ranges as needed to attain a desired expression level of each polypeptide, to attain a desired pharmacologic endpoint or other desired result.

In embodiments, formulations also may be constructed to locate passively or actively to different cell types in vivo, including, but not limited to hepatocytes, immune cells, tumor cells, endothelial cells, antigen presenting cells and leukocytes (Akinc et al., Mol Ther 2010, 18:1357-1364; Song et al., Nat Biotechnol 2005, 23:709-717; Judge et al., J Clin Invest 2009, 119:661-673; Kaufmann et al., Microvasc Res 2010, 80:286-293; Santel et al., Gene Ther 2006, 13:1222-1234; Santel et al., Gene Ther 2006, 13:1360-1370; Gutbier et al., Pulm Pharmacol Ther 2010, 23:334-344; Basha et al., Mol Ther 2011, 19:2186-2200; Fenske & Cullis, Expert Opin Drug Deliv 2008, 5:25-44; Peer et al., Sci 2008, 319:627-630; and Peer & Lieberman, Gene Ther 2011, 18:1127-1133, the content of each of which is incorporated herein by reference in entirety).

An example of passive targeting of a formulation to liver cells relies on LNP with lipid thereof bound to apolipoprotein E, which is bound by receptors on hepatocytes (Akinc et al., Mol Ther 2010, 18:1357-1364, the content of which is incorporated herein by reference in entirety). Formulations also can be selectively targeted through expression of different ligands or one of a binding pair on a surface of an LNP as exemplified by, for example, folate, transferrin, N-acetylgalactosamine (GalNAc), antibody targeted approaches (Kolhatkar et al., Curr Drug Discov Technol 2011, 8:197-206; Musacchio & Torchilin, Front Biosci 2011, 16:1388-1412; Yu et al., Mol Membr Biol 2010, 27:286-298; Patil et al., Crit Rev Ther Drug Carrier Syst 2008, 25:1-61; Benoit et al., Biomacromol 2011, 12:2708-2714; Zhao et al., Expert Opin Drug Deliv 2008, 5:309-319; Akinc et al., Mol Ther 2010, 18:1357-1364; Srinivasan et al., Methods Mol Biol 2012, 820:105-116; Ben-Arie et al., Meth Mol Biol 2012, 757:497-507; Peer, 2010 J Cont Rel 20:63-68; Peer et al., PNAS 2007, 104:4095-4100; Kim et al., Meth Mol Biol 2011, 721:339-353; Subramanya et al., Mol Ther 2010, 18:2028-2037; Song et al., Nat Biotechnol 2005, 23:709-717; Peer et al., Sci 2008, 319:627-630; and Peer & Lieberman, Gene Ther 2011, 18:1127-1133, the content of each of which is incorporated herein by reference in entirety); and so on.

The terms, "therapeutic," and, "prophylactic," can be used interchangeably herein with respect to features and embodiments of the instant disclosure.

Nanoparticle compositions may be useful for treating a disease, disorder or condition, such as, one missing, or has a deficient or aberrant protein or polypeptide activity. For example, a nanoparticle composition comprising an mRNA encoding a missing or aberrant polypeptide may be administered or delivered to a cell. Subsequent translation of that mRNA may produce that polypeptide, thereby reducing or eliminating an issue caused by absence of or aberrant activity caused by a polypeptide in vivo. Because translation may occur rapidly, methods and compositions of interest may be useful in treating acute diseases, disorders or conditions, such as, sepsis, stroke and myocardial infarction. A therapeutic and/or prophylactic mRNA included in a nanoparticle may be capable of altering rate of transcription of a given species, thereby affecting gene expression, such as using gene editing materials and methods, such as a CAS enzyme.

Diseases, disorders, and/or conditions characterized by dysfunctional or aberrant protein or polypeptide activity for which a composition may be administered include, but are not limited to, rare diseases, infectious diseases (vaccines, therapeutics and so on), cancer and proliferation diseases, genetic diseases (for example, cystic fibrosis and so on), autoimmune diseases, diabetes, neurodegenerative diseases, cardiovascular diseases, renovascular diseases, a metabolic disease; and so on. Diseases, disorders and/or conditions may be characterized by missing (or substantially diminished such that proper protein function does not occur) protein activity. Such proteins may not be present, or essentially may be non-functional. An example of a dysfunctional protein is a missense mutation variant of cystic fibrosis transmembrane conductance regulator (CFTR) gene, which produces a dysfunctional protein variant of CFTR protein, which causes cystic fibrosis. The instant disclosure provides a method for treating such diseases, disorders and/or conditions in a subject by administering a nanoparticle composition including a first or second LNP, an RNA encoding CFTR. Progress of therapy can be monitored by conventional techniques and assays, as well as patient input.

Nanoparticle compositions including two or more therapeutic and/or prophylactic mRNA's may be used in combination with one or more other therapeutic or prophylactic agents. By, "in combination with," is not intended to imply agents must be administered at the same time and/or formulated for delivery together, although methods of such delivery are within the scope of the instant disclosure. For example, two or more nanoparticle compositions including two or more different therapeutic and/or prophylactic polypeptides may be administered in combination. Compositions can be administered concurrently with, prior to, or subsequent to one or more other desired therapeutics or medical procedures.

Such an other agent may be, for example, an anti-inflammatory compound, a steroid (for example, a corticosteroid and so on), a statin, a hormone, a cytokine inhibitor, a glucocorticoid receptor modulator, an antihistamine and so on.

A pharmaceutic composition can be included in a container, pack or dispenser together with instructions for administration, forming a kit, an article of manufacture. A kit can comprise a unit dosage form, a multiple unit dosage form, a bulk container for dispensing unit doses and so on. A kit can include a device for delivering a dose, such as, a syringe, a suppository applicator or insertion device; and so on. A kit can include a liquid diluent.

A pharmaceutical composition including two or more nanoparticle compositions may be prepared by any method known in the art of pharmacology. In general, such preparatory methods include bringing an active ingredient into association with one or more other accessory ingredients, and then, if desirable or necessary, dividing, shaping, packaging and so on a product into a desired single-dose or multi-dose unit as an article of manufacture.

As used herein, a, "unit dose," is a discrete amount of a pharmaceutic composition comprising a predetermined amount of each LNP. Amount of active ingredient generally is equal to dosage of an active ingredient which would be administered to a subject; a convenient fraction of such a dosage, such as, for example, one-half, one-third and so on of such a dosage; and so on is administered to a subject.

Pharmaceutic compositions may be prepared in a variety of forms suitable for a variety of routes and methods of administration. For example, pharmaceutical compositions may be prepared in liquid dosage forms (for example, emulsions, microemulsions, nanoemulsions, solutions, suspensions, syrups, elixirs and so on), injectable forms, solid dosage forms (for example, capsules, tablets, pills, powders granules and so on), dosage forms for topical and/or transdermal administration (for example, ointments, pastes, creams, lotions, gels, powders, solutions, sprays, inhalants, patches, microneedles (Waghule et al., Biomed Pharmacotherap 109:1249-1258, 2019) and so on), suspensions, powders; and other forms.

In embodiments, nanoparticle compositions and/or pharmaceutical compositions of the disclosure are refrigerated or frozen for storage and/or shipment (for example, stored at a temperature of about 4° C. or lower, such as, a temperature between about-150° C. and about 0° C. In embodiments, an LNP formulation can be stored at normal room temperatures of about 20-22° C. For example, nanoparticle compositions and/or pharmaceutic compositions disclosed herein are stable for about at least 1 week, about at least 2 weeks, about at least 3 weeks, about at least 4 weeks, about at least 5 weeks, about at least 6 weeks, about at least 1 month or longer, for example, at a temperature of about 4° C. or lower.

In embodiments, an LCP formulation of interest is desiccated to a dry powder, for example, by freeze drying, lyophilization and so on, practicing methods and material known in the art.

Depending on diluent or carrier of a final formulation, surface of an LNP can be modified using known chemistries and methods to provide, for example, a hydrophilic coating for stability in an oleaginous base or medium, which is removable when exposed to an aqueous or hydrophilic environment.

In embodiments, a pharmaceutic composition of the disclosure has a pH value between about 7 and 8 (for example, 6.8 6.9, 7.0, 7.1, 7.2, 7.3, 7.4, 7.5, 7.6, 7.7, 7.8, 7.9 or 8.0, between 7.5 and 8 or between 7 and 7.8).

"Stability," "stabilized," "stable," and grammatic forms thereof refer to resistance of nanoparticle compositions and/or pharmaceutical compositions disclosed herein to chemical or physical change (for example, degradation, particle size change, aggregation and so on) under given manufacturing, preparation, transportation, storage and/or in use conditions.

Nanoparticle compositions are suitable for administration to any other animal, such as, a mammal. Modification of compositions suitable for administration to various animals is understood by a veterinarian or veterinary pharmacologist using ordinary and routine measures.

The instant disclosure now will be exemplified in the following non-limiting examples.

The instant invention is further defined in the following Examples. It should be understood that the Examples, while indicating embodiments of the invention, are given by way of illustration only. From the above discussion and the Examples, one skilled in the art can ascertain the essential characteristics of the invention, and without departing from the spirit and scope thereof, can make various changes and modifications of the invention to adapt to various uses and conditions.

EXAMPLES

Example 1

Hepatitis C (HepC) infects more than 70 million people worldwide. HepC is a leading cause of hepatocellular carcinoma and of liver transplants. Often, infections are asymptomatic. Nevertheless, the rate of persistence is high. That can lead to chronic liver disease, cirrhosis, carcinoma and so on.

Hence, chronically ill people often carry neutralizing antibody, and one form of treatment is gamma globulin from patients. (Yu et al., PNAS 101 (20) 7705-7710, 2004).

HepC virus (HCV) is diverse, HCV can comprise six genetically distinct genotypes and at least 70 subtypes (Owisianka et al., J Virol 79 (17) 11095-11104, 2005). Envelope proteins, E1 and E2, are pertinent to cell binding by virus and entry of virus into cells (Takamizawa et al., J Virol 67 (3) 1105, 1991).

Historically, majority of neutralizing antibodies were found to bind conformational epitopes of E2. A linear epitope in E2 was located and found not be to strain-specific (Owisianka et al., supra). E1, E2 and the E1E2 complex have been mapped for neutralizing or conserved determinants. Antigenic region 4 (AR4) is present on E1E2. The neutralizing face of E2 overlaps with a CD81 receptor binding site.

The N terminal hypervariable region (HVR1) of E2 is believed to be home to an immunodominant epitope. (Aleman et al., PNAS 115 (29) 7569-7574, 2018; and Colberta et al., Path Imm 93 (14) e02070-18, 2019).

In embodiments, a first mRNA encodes E2 but lacking HVR1 (Charloteaux et al., J Virol 76:194, 2002; Urbanowicz et al., Meth Mol Biol 1911:275-294, 2019; Dobuisson et al., J Virol 68:6147, 1994; Duvet et al., Glycobiol 12:95, 2002; Kong et al., Sci 342:1090, 2013; Slater-Handslig et al., Virol 319:36, 2004; Helle et al., Viruses 3:1909, 2011; and Prentoe et al., Hepat 64:1881, 2016).

A second mRNA encodes E1 or E1E2 complex.

The two mRNA's are loaded into different populations of LNP's. A solution of DOTMA/phosphatidyl choline/cholesterol/1,2-dimyristoyl-sn-glycero-3-phosphoethanolamine-N-[methoxy (polyethylene glycol)] (PEG-DMG) in a molar ratio of 50/10/38.5/1.5 in ethanol is mixed with a 50 mM sodium citrate buffer (pH 4.0) containing an mRNA at a volume ratio of 3:1 in a microfluidic mixer (Precision Nanosystems, Vancouver, CA). (Maeki et al., Ad Drug Deliv Rev 128:84-100, 2018). The N/P is 5.6. The formed LNP's are dialyzed against pH 7 PBS, are passed through a 0.22 μm filter and are stored.

The two LNP's are combined 1:1 to provide an HCV vaccine.

Chimpanzees (Folgori et al., Nat Med 12 (2) 190-197, 2006) are housed under approved conditions.

Chimpanzees are injected IM in deltoid muscle with 100 µg of an LNP formulation comprising a first LNP population carrying an E1 encoding mRNA and a second population carrying an E1E2 encoding mRNA with E2 lacking HVR1. Control animals are injected with an LNP carrying an mRNA encoding an influenza hemagglutinin.

A month after immunization, presence of serum α-HCV antibody is detected by ELISA (Creative Diagnostics, Shirley, NY; TK Biotech, Poway, CA).

Five weeks post immunization, control and experimental animals are challenged with an IV bolus of 100 CID50 (50% tissue culture infective dose) of prototype strain H77.

Control chimpanzees present with viremia 1-2 weeks after challenge as detected by ELISA and by a PCR genomic assay. On the other hand, vaccinated animals present with a delayed and reduced level of viremia.

Example 2

Respiratory syncytial virus is a highly infectious pathogen that infects almost all children under the age of 3. In terms of global mortality, it is believed RSV is responsible for almost 7% of all deaths of children between 1 month of age and 1 year of age, second only to malaria. Immunity wanes and reinfection is common.

There are two subtypes, A and B. RSV infects primarily and perhaps exclusively a respiratory tract. (Hashimoto & Hosoya, Fuku J Med Sci 63 (3) 127-133, 2017)

Of three proteins on a capsid surface (SH is an ion channel and G is suspected as an attachment protein), fusion (F) protein is indispensable for infection and F is a primary target of neutralizing antibodies.

F requires proteolytic cleavage for activation. Hence, there is a prefusion form and a postfusion form. Mature F is a trimer of two polypeptides, F1 and F2.

Mclellan (Curr Opn Virol 11:70-75, 2015) manipulated F to obtain a locked, soluble prefusion form. Neutralizing epitopes are found on postfusion and on prefusion forms.

An immune response favoring a more significant cellular immune response may be desirable.

In embodiments, a first mRNA encodes a full length F1 polypeptide. Mclellan et al., Curr Top Microbiol Imm 372: 83, 2013; Swanson et al., PNAS 108:9619, 2011; Mclellan et al., Sci 340:1113, 2013)

A second mRNA encodes a full length F2 polypeptide.

In embodiments, an mRNA includes sequences encoding one or two Lys domains upstream and/or downstream of an ORF.

In embodiments, a first mRNA encodes a prefusion F. (McLellan et al., 2013, supra; Gilman et al., Nat Comm 10:2105, 2019). A second mRNA encodes a full length postfusion F (Mclellan et al., J Virol 85:7788, 2011).

In embodiments, another mRNA encodes G. In embodiments, the another mRNA encodes a portion of G comprising a central, conserved domain of G, avoiding 5' and 3' portions of G ORF which present with greater variability. (Mclellan et al., Curr Top Microbiol Imm 372:83-104, 2013, Jones et al., PLOS Path 14 (3) e1006935, 2018).

In embodiments, an mRNA encodes at least N terminal, extracellular domain of SH.

Two or more of any of the above mRNA's are loaded into individual LNP's as provided in Example 1 and are combined in equal amounts to provide an RSV vaccine, which can be formulated for delivery to a respiratory system.

Six-eight week female BALB/c mice are housed under approved conditions.

A 50 µl inoculum containing 50 µg of an LNP formulation comprising a first LNP population carrying an F1 encoding mRNA and a second population carrying an F2 encoding mRNA is administered intranasally under anesthesia. Control animals are exposed to an LNP carrying an mRNA encoding an influenza hemagglutinin.

A month after immunization, presence of serum α-RSV antibody in blood collected from retroorbital plexus is detected by ELISA (abcam, Cambridge, MA).

Five weeks post immunization, control and experimental animals are challenged with an IP bolus of 106 PFU of Long strain (subgroup A) RSV propagated in HEp-2 cells (ATCC) (Connors et al., J Virol 66 (12) 7444-7451, 1992).

After one month, blood is collected for determining level of viremia and animals are sacrificed for lung biopsy.

Control mice present with viremia 1-2 weeks after challenge as detected by ELISA and by a PCR genomic assay. Lung histology reveals lymphocyte infiltration. On the other hand, vaccinated animals present with little or no viremia, and lung biopsies reveal little or no lymphocyte infiltration.

Example 3

Cytomegalovirus (CMV) is a significant contributor to birth defects. Congenital CMV infection can result in hearing loss and other neurodevelopment disabilities. Up to 15% of congenitally infected children develop long term sequelae.

CMV infection also is an issue with patients having another disorder or disease, such as, a transplant recipient, an immunocompromised individual, such as, a patient inflicted with HIV, and so on.

CMV seems to infect two types of cells, fibroblasts and epithelial/endothelial cells, although there may be a distinction between infecting epithelial cells and endothelial cells (Qi et al., Virol J 17:50, 10.1186/s12985-020-01320-2, 2020).

Two different complexes of virus molecules are employed to infect those two populations of cells. Fibroblast entry requires at least gB and gH/gL/gO; whereas endothelial/ epithelial cell entry requires an additional pentameric complex of gH/gL/UL128/UL130/UL131. The pentameric complex also is needed for virus entry into immune cells.

Natural immunization elicits a vigorous antibody response (Wang et al., Vacc 29:9075-9080, 2011).

Spindler et al. (J Virol 87 (16) 8927-8939, 2013) discovered a conformational, neutralizing epitope in gB, which is conserved amongst Herpesviruses. Five antigen domains (AD-1 to AD-5) are found in gB. Most neutralizing antibodies bind to AD-4 or AD-5 of gB. AD-4 is formed from discontinuous portions of gB. gB may comprise an immunodominant epitope (Choi et al., infra).

Chiuppesi et al. (J Virol 91 (6) e01857-16, 2017) discovered a linear, neutralizing epitope in UL128.

Ha et al. (J Virol 91 (7) e02033-16, 2017) uncovered eight antigen sites on pentameric complex.

In embodiments, a first mRNA encodes gH, gL or gO (Zhou et al., J Virol 89:8999, 2015; Wang et al., Front Microbiol doi: 10.3389/fmich.2020.01511). A second mRNA encodes UL128, UL130 or UL131 (Ryckman et al., J Virol 82:60, 2008; Ciferi et al, PNAS 112:1767, 2015; Loughney et al., JBC 290:15985, 2015).

The two mRNA's are loaded into LNP's as provided in Example 1, and those two LNP populations are combined 1:1 to form a formulation that can serve as a CMV vaccine.

Seronegative guinea pigs (Choi et al., J Virol 90 (17) 7902-7919, 2016) are housed under approved conditions. Guinea pigs are a suitable model for congenital CMV infection.

A 100 μl inoculum containing 50 μg of an LNP formulation comprising a first LNP population carrying guinea pig equivalent of gH/gL encoding mRNA and a second population carrying guinea pig equivalent of UL128-131 encoding mRNA is administered SC to female animals (Choi et al., supra). Control animals are exposed to an LNP carrying an mRNA encoding an influenza hemagglutinin.

A month after immunization, presence of serum α-CMV antibody is detected by ELISA (abcam, Cambridge, MA).

Seroconverted animals are paired with male guinea pigs. Pregnant dams are challenged with an SC immunization of 105 PFU of guinea pig CMV (Choi et al., supra) and animals allowed to go to term.

Viral load of liver, lung, and brain in live and stillborn pups are assessed by PCR.

Vaccine reduces pup mortality and treated pups have lower levels of tissue CMV than do control pups.

Example 4

Measles virus (MeV) hemagglutinin (H) attaches to signaling lymphocyte activation molecule (SLAM or CD150), CD46 (Pfeuffer et al., infra) or poliovirus receptor-like 4 (PVRL4, also known as nectin 4) on a cell. Fusion (F) protein enables virus to enter the cell. On attachment, F undergoes a conformational change that provides a physical mechanism for cell entry. (Plemper et al., PLOS Path 7 (6) e1002058, 2011; Hashiguchi et al., Front Imm 2:247, 2011; and Plattet et al., Viruses 8:112, 2016.)

In embodiments, an mRNA encodes a measles H polypeptide or antigenic portion thereof. Two populations of LNP's are made. A first mRNA is configured to secrete H comprising a sequence encoding a signal peptide. A second mRNA is configured to include a 5' sequence encoding a tetrapeptide Lys domain and a 3' sequence encoding a tetrapeptide Lys domain.

Cotton rats are housed under approved conditions.

A 50 μl inoculum containing 50 μg of an LNP formulation comprising the two LNP populations carrying secreted and intracellular His administered intranasally under anesthesia. Control animals are exposed to an LNP carrying an mRNA encoding an influenza hemagglutinin.

A month after immunization, presence of serum α-MeV antibody from blood collected from retroorbital plexus is detected by ELISA (LSBio, Seattle, WA).

Five weeks post immunization, control and experimental animals are challenged with a 50 μl intranasal bolus of 106 PFU of Edm MeV propagated in Vero cells (ATCC) (Pfeuffer et al., supra) under anesthesia.

After one month, blood is collected for determining level of viremia and animals are sacrificed for lung tissue. Lung is minced and supernatant tested for virus presence using Vero cells or B95a cells (marmoset lymphoblastoid line, ECACC) by assessing cytopathic effect after seven days of incubation.

Control rats present with viremia 1-2 weeks after challenge as detected by ELISA. MeV replicates better in lung tissue in control animals than in animals of the experimental group.

Mumps virus (MuV) capsid contains a hemagglutinin/ neuraminidase (HN) polypeptide and a fusion (F) polypeptide. HN binds to sialic acid residues which are found on many types of cells (Rubin et al., J Path 235 (2) 242-252, 2015).

SH is variable and often used to type mumps strains.

Mumps virus genome (Elango et al., J Gen Virol 69:2893-2900, 1988) has been manipulated, for example, to lack small hydrophobic (SH) polypeptide (Malik et al., J Virol 85:6082-6085, 2011). Cox et al. cloned and ascertained structural and functional characteristics of P (J Virol 87 (13) 7558-7568, 2013).

MuV vaccines generally contain A or B genotypes. Genotype G is circulating in the US and genotype C is circulating in India.

In embodiments, an mRNA encodes a mumps HN polypeptide or antigenic portion thereof; or portion of HN comprising hemagglutinin or antigenic portion thereof, although HN may comprise an immunodominant epitope (Almansar et al., Front Microbiol 11:1999, 2020).

An mRNA encoding an antigenic polypeptide of F is placed in an LNP as provided in Example 1.

Six-eight week female BALB/c mice are housed under approved conditions.

A 50 μl inoculum containing 50 μg of an LNP carrying an F encoding mRNA is administered intranasally under anesthesia. Control animals are exposed to an LNP carrying an mRNA encoding an influenza hemagglutinin.

A month after immunization, presence of serum α-MuV antibody from blood collected from retroorbital plexus is detected by ELISA (LSBio, Seattle, WA).

MuV replication is sensitive to anti-viral activity of interferons α and β. Hence, an (INF-α/βR$^{-/-}$) knockout mouse (Jackson Labs, Bar Harbor, ME) is a usable animal model for MuV replication.

The knockout mouse is on the C57BL/6 background.

A 50 μl inoculum containing 50 μg of an LNP carrying an F encoding mRNA is administered intranasally under anesthesia. Control animals are exposed to an LNP carrying an mRNA encoding an influenza hemagglutinin.

A month after immunization, presence of serum α-MuV antibody from blood collected from retroorbital plexus is detected by ELISA (LSBio, Seattle, WA).

Animals are challenged with 3×10$^6$ PFU of MuV in 100 μl delivered intranasally (Pickar et al., PLOS ONE 12 (3) e0174444, 2017).

A month after challenge, presence of serum MuV from blood collected from retroorbital plexus is detected by ELISA (LSBio, Seattle, WA) in control animals. Vaccinated animals revealed lower or non-existent levels of serum MuV.

Two mRNA's encoding a measles antigenic polypeptide and a mumps polypeptide, respectively, are loaded into LNP's as provided in Example 1, and those two LNP populations are combined 1:1 to form a formulation that can serve as a measles/mumps vaccine.

Rubella virus (RV or RuV) capsid is comprised of C protein. Capsid is covered with a lipid bilayer. Inserted in a lipid bilayer are two glycoproteins, E1 and E2. Hemagglutinin and neutralizing sites based on mAb probes reside on E1 (Yang et al., J Virol 72 (11) 8747-8755, 1998). E2 may be obscured by E1. (Chaye et al., J Clin Microb 30 (9) 2323-2329, 1992; and Prasad et al., PNAS 110 (50) 20105-20110, 2013).

In embodiments, an mRNA encodes a rubella E1 polypeptide or antigenic portion thereof.

Six-eight week female BALB/c mice are housed under approved conditions.

A 50 μl inoculum containing 50 μg of an LNP formulation comprising an E1 encoding mRNA is administered intranasally under anesthesia. Control animals are exposed to an LNP carrying an mRNA encoding an influenza hemagglutinin.

A month after immunization, presence of serum α-RuV antibody from blood collected from retroorbital plexus is detected by ELISA (LSBio, Seattle, WA; Creative Diagnostics, Shirley, NY).

A third LNP comprising an mRNA encoding a rubella E1 polypeptide or antigenic portion thereof can be combined with the measles/mumps vaccine formulation described above in a 1:1:1 relative ratio to provide an MMR vaccine.

All references cited herein are herein incorporated by reference in entirety.

It will be appreciated that various changes and modifications can be made to the teachings herein without departing from the spirit and scope of the disclosure.

What is claimed is:

1. An article of manufacture comprising at least two lipid nanoparticles (LNP), comprising:
   a) a first LNP comprising a first mRNA encoding a first polypeptide of a pathogen; and
   b) a second LNP comprising a second mRNA encoding a second polypeptide of said pathogen, said second polypeptide comprising a cryptic epitope of said pathogen,
   wherein said first and said second polypeptides do not comprise an immunodominant epitope of said pathogen-cell.

2. The article of manufacture of claim 1, wherein said pathogen comprises hepatitis C virus.

3. The article of manufacture of claim 1, wherein said pathogen comprises hepatitis B virus.

4. The article of manufacture of claim 1, further comprising an LNP comprising an mRNA encoding a polypeptide comprising an adjuvant.

5. The article of manufacture of claim 1, wherein said pathogen comprises a measles virus.

6. The article of manufacture of claim 1, wherein said pathogen comprises a mumps virus.

7. The article of manufacture of claim 1, wherein said pathogen comprises an influenza.

8. The article of manufacture of claim 1, where said pathogen comprises a respiratory syncytial virus.

9. The article of manufacture of claim 1, where said pathogen comprises a cytomegalovirus.

10. The article of manufacture of claim 1, where said pathogen comprises a respiratory syncytial virus.

11. The article of manufacture of claim 1, where said pathogen comprises a human immunodeficiency virus.

12. The article of manufacture of claim 1, where said pathogen comprises a rhinovirus.

13. The article of manufacture of claim 1, where said pathogen comprises an agent causing an infectious disease.

* * * * *